US008852621B2

(12) United States Patent
Patel et al.

(10) Patent No.: US 8,852,621 B2
(45) Date of Patent: Oct. 7, 2014

(54) MULTILAYER FIBROUS POLYMER SCAFFOLDS, METHODS OF PRODUCTION AND METHODS OF USE

(75) Inventors: Shyam Patel, Oakland, CA (US); Kyle Kurpinski, Berkeley, CA (US); Yinki Clement Wong, Sunnyvale, CA (US)

(73) Assignee: NanoNerve, Inc., Berkeley, CA (US)

( * ) Notice: Subject to any disclaimer, the term of this patent is extended or adjusted under 35 U.S.C. 154(b) by 601 days.

(21) Appl. No.: 12/575,432

(22) Filed: Oct. 7, 2009

(65) Prior Publication Data
US 2010/0233115 A1 Sep. 16, 2010

Related U.S. Application Data

(60) Provisional application No. 61/103,526, filed on Oct. 7, 2008, provisional application No. 61/145,919, filed on Jan. 20, 2009.

(51) Int. Cl.
*A61F 2/00* (2006.01)
*A61L 15/26* (2006.01)
*A61L 27/18* (2006.01)

(52) U.S. Cl.
CPC *A61L 27/18* (2013.01); *A61L 15/26* (2013.01)
USPC .......................................................... 424/423

(58) Field of Classification Search
None
See application file for complete search history.

(56) References Cited

U.S. PATENT DOCUMENTS

| | | |
|---|---|---|
| 4,323,525 A | 4/1982 | Bornat |
| 5,861,034 A | 1/1999 | Taira et al. |
| RE36,370 E | 11/1999 | Li |
| 6,309,423 B2 | 10/2001 | Hayes |
| 6,347,930 B1 | 2/2002 | Muscat et al. |
| 6,616,435 B2 | 9/2003 | Lee et al. |
| 6,673,285 B2 | 1/2004 | Ma |
| 6,676,675 B2 | 1/2004 | Mallapragada et al. |
| 6,716,225 B2 | 4/2004 | Li et al. |
| 6,790,528 B2 | 9/2004 | Wendorff et al. |
| 7,135,134 B2 | 11/2006 | Tepper et al. |
| 7,163,545 B2 | 1/2007 | Yaszemski et al. |
| 7,172,765 B2 | 2/2007 | Chu et al. |
| 7,209,616 B2 | 4/2007 | Welker et al. |
| 7,214,242 B2 | 5/2007 | Abraham et al. |
| 7,276,271 B2 | 10/2007 | Dubson et al. |
| 7,374,774 B2 | 5/2008 | Bowlin et al. |
| 7,622,299 B2 | 11/2009 | Sanders et al. |
| 2003/0171053 A1 | 9/2003 | Sanders |
| 2006/0226580 A1 | 10/2006 | Xia et al. |
| 2007/0026039 A1 | 2/2007 | Drumheller et al. |
| 2007/0269481 A1 | 11/2007 | Li et al. |
| 2008/0220042 A1* | 9/2008 | Hashi et al. .................. 424/423 |

FOREIGN PATENT DOCUMENTS

| | | |
|---|---|---|
| WO | 02/102432 A1 | 12/2002 |
| WO | 2006/105441 A2 | 10/2006 |
| WO | 2007/089259 A1 | 8/2007 |
| WO | 2007/090102 A2 | 8/2007 |
| WO | 2007/112446 A2 | 10/2007 |
| WO | 2007/146261 A2 | 12/2007 |
| WO | 2008/013713 A2 | 1/2008 |

OTHER PUBLICATIONS

Klopp et al., Spine, 2008, 33(14), pp. 1518-1526.*
Brostrom et al., Biomacromolecules, 2004, 5(3), pp. 1124-1134.*
Barbolt, et al., "Biocompatibility evaluation of dura mater substitutes in an animal model," *Neurol Res* (2001), 23: pp. 813-820.
Bejjani, et al., "Safety and efficacy of the porcine small intestinal submucosa dural substitute: results of a prospective multicenter study and literature review," *J Neurosurg* (2007), 106: pp. 1028-1033.
Bhatia, et al., "A synthetic dural prosthesis constructed from hydroxyethylmethacrylate hydrogels," *J Neurosurg* (1995), 83: pp. 897-902.
Biroli, et al., "Novel Equine Collagen-Only Dural Substitute," *Neurosurg [ONS Suppl 1]* (2008), 62: pp. 273-274.
Brostrom et al., "Biodegradable Films of Partly Branched Poly(L-lactide)-co-poly(ϵ-caprolactone) Copolymer: Modultation of Phase Morphology, Plasticization Properties and Thermal Depolymerization," *Biomacromolecules*, 5:3 (2004) 1124-1134, especially abstract, retrieved on Dec. 22, 2009; url:http://pubs.acs.org/doi/abs/10.1021/ bm049920q.
Castelnuovo, et al., "Endonasal Endoscopic Duraplasty: Our Experience," *Skull Base* (2006), 16(1): pp. 19-23.
Dufrane, et al., "Clinical application of a physically and chemically processed human substitute for dura mater," *J Neurosurg* (2003), 98: 1198-1202.
Haq, et al., "Postoperative fibrosis after surgical treatment of the porcine spinal cord: a comparison of dural substitutes," *J Neurosurg Spine* (2005), 2: pp. 50-54.
Hida, et al., "Nonsuture dural repair using polyglycolic acid mesh and fibrin glue: clinical application to spinal surgery," *Surg Neurol* (2006), 65: pp. 136-143.
Hieb, et al., "Spontaneous Postoperative Cerebrospinal Fluid Leaks Following Application of Anti-Adhesion Barrier Gel," *Spine* (2001), 26(7): pp. 748-751.
Klopp, et al., "Comparison of a Caprolactone/Lactide Film (Mesofol) to Two Polylactide Film Products as a Barrier to Postoperative Peridural Adhesion in an Ovine Dorsal Laminectomy Model," *Spine* (2008), 33(14): pp. 1518-1526.

(Continued)

Primary Examiner — Brian Gulledge
(74) Attorney, Agent, or Firm — Dorsey & Whitney LLP

(57) ABSTRACT

Fibrous polymer scaffolds and methods of manufacture are provided. The scaffolds can be formed of multiple layers and the extent and direction of alignment of each layer can be controlled. Efficient fabrication systems and methods for producing such scaffolds include apparatuses and processes are also provided. Kits including the fibrous polymer scaffolds and methods for implanting such scaffolds are also provided.

14 Claims, 16 Drawing Sheets

(56) References Cited

OTHER PUBLICATIONS

Kurpinski et al., "Dura mater regeneration with a novel synthetic, bilayered nanofibrous dural substitute: an experimental study," *Nanomedicine* (2011), 6(2): pp. 325-337.
Laquerriere, et al., "Experimental evaluation of bilayered human collagen as a dural substitute," *J Neurosurg* (1993), 78: pp. 487-491.
Li, et al. "Electrospinning of Polymeric and Ceramic Fibers as Uniaxially Aligned Arrays," *Nano Lett*. (2003), 3(8): pp. 1167-1171.
Maikos, et al., "Mechanical Properties of Dura Mater from the Rat Brain and Spinal Cord," *J Neurotrauma* (2008), 25: pp. 38-51.
Martin, et al., "Wound Healing—Aiming for Perfect Skin Regeneration," *Science* (1997), 276: pp. 75-81.
McCall, et al., "Use of resorbable collagen dural substitutes in the presence of cranial and spinal infections—report of 3 cases," *Surg Neurol*. (2008), 70(1): pp. 92-96.
Mello, et al., "Duraplasty with biosynthetic cellulose: an experimental study," *J Neurosurg* (1997), 86: pp. 143-150.
Mukai, et al., "Development of Watertight and Bioabsorbable Synthetic Dural Substitutes," *Artif Organs* (2008), 32(6): pp. 473-483.
Narotam, et al., "A clinicopathological study of collagen sponge as a dural graft in neurosurgery," *J Neurosurg* (1995), 82: 406-412.
Narotam, et al., "Collagen Matrix (DuraGen) in Dural Repair: Analysis of a New Modified Technique," *Spine* (2004), 29(24): pp. 2861-2867.
Narotam, et al., "Collagen matrix duraplasty for cranial and spinal surgery: a clinical and imaging study," *J Neurosurg* (2007), 106: pp. 45-51.
Parizek, et al., "Ovine pericardium: a new material for duraplasty," *J Neurosurg* (1996), 84: pp. 508-513.
Preul, et al., "A Unique Dual-Function Device: A Dural Sealant with Adhesion Prevention Properties," *DuraSeal Spine White Paper* (2005), 5 pages.
Preul, et al., "Obtaining Watertight Closures of Duraplasty Onlay Grafts in a Craniotomy Preclinical Model," *DuraSeal Package Insert* (2005), 8 pages.
Rabinowitz, et al., "Growth of rat cortical neurons on DuraGen, a collagen-based dural graft matrix," *Neurol Res* (2005), 27: pp. 887-894.
Rosen, et al., "Artificial Nerve Graft Using Collagen as an Extracellular Matrix for Nerve Repair Compared with Sutured Autograft in a Rat Model," *Ann. Plast. Surg*. (1990), 25(5): pp. 375-387.
Runza, et al., "Lumbar Dura Mater Biomechanics: Experimental Characterization and Scanning Electron Microscopy Observations," *Anesth Analg* (1999). 88: pp. 1317-1321.
Tachibana, et al., "Evaluation of the healing process after dural reconstruction achieved using a free fascial graft," *J Neurosurg* (2002), 96: pp. 280-286.
Tatsui, et al., "Evaluation of DuraGen in preventing peridural fibrosis in rabbits," *J Neurosurg Spine* (2006), 4: pp. 51-59.
Yamada, et al., "Development of a dural substitute from synthetic bioabsorbable polymers," *J Neurosurg* (1997), 86: pp. 1012-1017.
Yamada, et al., "Clinical application of a new bioabsorbable artificial dura mater," *J. Neurosurg* (2002), 96: pp. 731-735.
Zerris, et al., "Repair of the Dura Mater With Processed Collagen Devices", *J Biomed Mater Res Part B: Appl Biomater* (2007), pp. 580-588, DOI: 10.1002/jbm.b.30831.
International Search Report and Written Opinion issued with respect to PCT Application No. PCT/US2009/059890, 10 pages.
"Extended European Search Report", mailed Dec. 11, 2013, for EP 09819836.9.

\* cited by examiner

Steel drum – no arms

2D FFT

Steel drum – arms longitudinal

2D FFT

Multi-sec conveyor belt – no arms

2D FFT

Multi-sec conveyor belt – arms longitudinal

2D FFT

Multi-sec drum – arms long

Multi-section drum – arms circumferential

2D FFT

2D FFT

MULTILAYER FIBROUS POLYMER SCAFFOLDS, METHODS OF PRODUCTION AND METHODS OF USE

CROSS-REFERENCE TO RELATED APPLICATIONS

This application claims the benefit under 35 U.S.C. §119(e) from U.S. Provisional Application Ser. No. 61/103,526, filed Oct. 7, 2008 and U.S. Provisional Application Ser. No. 61/145,919 filed Jan. 20, 2009, both of which are herein incorporated by reference in their entireties.

FIELD

The disclosure relates to fibrous scaffolds finding application as medical devices for the repair of wounds, surgical incisions and/or biopsies and for promoting and/or improving the regeneration of anatomical biological components (i.e., biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc.).

BACKGROUND

Electrospinning is a technique known in the art for producing articles composed of polymer fibers. See U.S. Pat. No. 4,323,525. More recently, U.S. Pat. No. 7,276,271 disclosed a fibrous polymer tubular structure. Substrates with nanoscale aligned geometries are disclosed in U.S. Pat. No. 6,676,675. The use of electrospun fibrous polymer grafts in medical applications is disclosed in U.S. Pat. No. 7,172,765.

Other efforts have focused on tubular grafts made of biologically derived materials. See, for example, U.S. Pat. No. 7,214,242. Modified electrospinning methods for forming directed fibers are also disclosed in U.S. Pat. No. 7,135,134. PCT Publication Nos. WO 2007/146261 and WO 2007/090102 disclose various aspects of polymer fibrous scaffold sheets and tubes.

However, there is a need in the art for fibrous polymer scaffolds having multiple layers that provide flexibility and tensile strength in multiple directions. There is also a need to provide multiple layer fibrous scaffolds in which the layers will not de-laminate during use. There is a further need in the art for compositions that can promote the growth or regrowth of tissue or replace damaged tissue in a subject. Such scaffolds provide stability in a wide range of applications, particularly biomedical applications. Further, there is a need for apparatuses designed to manufacture such scaffolds. The present disclosure addresses these and other needs.

SUMMARY

Fibrous polymer scaffolds having at least a first layer of aligned polymer fibers and a second layer of polymer fibers are disclosed. The first and second layers can include a single continuous polymer fiber or a plurality of continuous polymer fibers. In various aspects, the second layer can include unaligned or randomly oriented fibers, or fibers that are aligned and offset from the average axis of alignment of the first layer. In various aspects, the scaffolds can include a plurality of layers including, without limitation, three, four, five, six, seven, eight, nine, ten or more layers.

The polymer scaffolds of the disclosure can be formed into a variety of shapes. In various aspects, the polymer scaffolds can be in the shape of a conduit. In various aspects, the polymer scaffolds can be in the shape of a membrane. The membrane may take any desired shape including, without limitation, a square, rectangle, circle and other shapes. The shape of the scaffolds may be designed to correspond to a specific tissue.

The second layer can be formed from a different polymer than the first layer, or the same polymer as the first layer. In some embodiments, the polymer fibers of the first layer and the polymer fibers of the second layer comprise a single, unbroken polymer fiber. In some embodiments, the polymer fibers of the first layer and the polymer fibers of the second layer comprise two, unbroken polymer fibers. In some embodiments, at least one polymer fiber in the first layer and at least one polymer fiber in the second layer is the same, continuous polymer fiber. In some embodiments, the fibers of the first layer and the fibers of the second layer comprise two polymers present in two continuous fibers. In some embodiments, the fibers of the first layer and the fibers of the second layer comprise three polymers present in three continuous fibers. In some embodiments, the fibers of the first layer and the fibers of the second layer comprise four polymers present in four continuous fibers. In some embodiments, the fibers of the first layer and the fibers of the second layer comprise five polymers present in five continuous fibers.

In some embodiments, the first layer is formed from aligned polymer fibers. The second layer can be formed from aligned polymer fibers, or from polymer fibers that are substantially unaligned or randomly oriented. In those embodiments where the second layer is formed from aligned polymer fibers, the orientation of the aligned fibers of the second layer can be offset from the axis of alignment of the fibers of the first layer.

In various aspects, the scaffolds ranges from about 100 microns to about 500 microns thick. In some embodiments, the thickness of the first layer is less than the thickness of the second layer. In some embodiments, the thickness of the first layer of aligned fibers is greater than about 1 micron and less than about 70 microns thick. In some embodiments, the thickness of the first layer of aligned fibers is greater than about 70 microns and less than about 150 microns thick. In some embodiments, the thickness of the first layer of aligned fibers is greater than about 150 microns and less than about 300 microns thick. In some embodiments, the thickness of the second layer of fibers is greater than about 150 microns and less than about 330 microns thick. In some embodiments, the total thickness of the scaffold is about 100 to about 200 microns, about 150 to about 250 microns, about 300 to about 400 microns, or about 500 microns. In some embodiments, the total thickness of the scaffold is greater than about 500 microns.

In various aspects, the polymer fibers of the first layer and the polymer fibers of the second layer are comprised of biodegradable polymers.

In various aspects, the polymer fibers of the fibrous polymer scaffolds can further optionally comprise an additive selected from the group consisting of poly(propylene glycol), poly(ethylene oxide), triethyl citrate, glycerol, poly(ethylene glycol), and combinations thereof.

In various aspects, the polymer fibers of the scaffolds can further optionally comprise a salt.

In various aspects, kits for the repair of wounds, surgical incisions or biopsies are provided. In some embodiments, the kits comprise at least one fibrous polymer scaffold and instructions for using the scaffold to repair wounds, surgical incisions and/or biopsies.

In various aspects, methods of implanting fibrous polymer scaffolds are provided. In some embodiments, the methods are directed toward treating an injury or defect in a subject and comprise applying a scaffold to an injury or defect site on or in said subject, in an amount, and under conditions, sufficient to treat the injury.

In other aspects, apparatuses for making fibrous polymer scaffolds are provided.

In some embodiments, an apparatus for making fibrous polymer scaffolds is provided that includes a rotational assembly having first and second conducting outer mandrels rotationally associated along a longitudinal axis of the assembly within an insulating sleeve between the outer mandrels. A charged electrically conducting spinneret configured to release a solution onto the insulating sleeve is positioned normal to the longitudinal axis of the assembly. In various embodiments, the sleeve can be configured to be disconnected from the two conducting mandrels and slid over the third conducting mandrel.

In some embodiments, an apparatus for making fibrous polymer scaffolds is provided wherein first, second, and third conducting mandrels are rotationally aligned along a longitudinal axis of the assembly. A first insulating region is disposed between and rotationally associated with the first and second conducting mandrels. A second insulating region is disposed between and rotationally associated with the second and third conducting mandrels. A charged electrically conducting spinneret is positioned normal to the longitudinal axis of the assembly and configured to release a solution onto the second, or central, conducting mandrel.

The insulating regions can have various dimensions and properties. In some embodiments, at least one insulating region is a hollow tube and connected to mandrels inserted into the lumen of the tube to form an overlap distance of the tube on each mandrel between 1 mm to 5 mm. In some embodiments, at least one insulating region is a hollow tube and connected to mandrels inserted into the lumen of the tube to completely cover at least one, and in some embodiments both, mandrels. The insulating region can be constructed from a non-conductive polymer, such as nylon, polytetrafluoroethylene (PTFE), polyvinylidene fluoride (PVDF), polyaryletheretherketone (PEEK), or polyvinyl chloride (PVC).

The conducting mandrels can have various dimensions and properties and can be constructed from any conducting compound, such as stainless steel and aluminum. In some three-mandrel embodiments, the first and third (outer) conducting mandrels can have equal length and/or the second (inner) conducting mandrel can have a shorter length than each outer mandrel. In some three-mandrel embodiments, the first and third (outer) conducting mandrels can have equal length and/or the second (inner) conducting mandrel can have a longer length than each outer mandrel. In some three-mandrel embodiments, the first and third (outer) conducting mandrels can have equal length and/or the second (inner) conducting mandrel can have the same length as each outer mandrel.

In various aspects, methods of making multilayer fibrous polymer scaffolds are provided. In some embodiments, a polymer solution is electrospun at a first rotation rate onto a rotational assembly to form an aligned first fibrous layer. A second polymer layer is then electrospun onto the rotational assembly without interrupting the flow of the polymer solution to form a non-aligned second fibrous layer. The first fibrous layer and second fibrous layer are thus comprised of a single, unbroken polymer fiber.

In some embodiments, a method of making a fibrous polymer scaffold conduit is disclosed that includes electrospinning a first layer of aligned polymer fibers onto an insulating sleeve, the sleeve being rotationally associated with a first conducting mandrel at a first end of the insulating sleeve and a second conducting mandrel at a second end of the insulating sleeve. The insulating sleeve is then transferred onto a third conducting mandrel, such that the lumen of the sleeve surrounds the third conducting mandrel, and a second layer of non-aligned polymer fibers is electrospun onto the first layer of aligned fibers.

In some embodiments, a method of making a fibrous polymer scaffold conduit is provided using a three mandrel rotational assembly. A rotational assembly is provided that includes first, second, and third conducting mandrels rotationally aligned along a longitudinal axis of the assembly. A first insulating region is disposed between and rotationally associated with the first and second conducting mandrels, and a second insulating region is disposed between and rotationally associate with the second and third conducting mandrels. The rotational assembly is rotated to electrospin a first layer of longitudinally aligned fibers onto a collector substrate comprising at least the second conducting mandrel. The mandrel assembly is further rotated at the same rotation rate for a period of time sufficient to electrospin a second layer of non-longitudinally aligned fibers onto the first layer of fibers.

In various aspects, the rate of revolution of the rotational assemblies of the apparatuses can be varied. In some embodiments, the rotational assemblies are rotated at a rate of 20 revolutions per minute (RPM) during the formation of at least one layer of fibers. In some embodiments, the rotational assemblies are rotated at a rate of greater than 1 RPM, greater than 5 RPM, greater than 20 RPM, greater than 100 RPM, greater than 800 RPM, greater than 1,000 RPM, greater than 2,000 RPM, greater than 3,000 RPM, greater than 4,000 RPM, or greater than 5,000 RPM during the formation of the layers. In some embodiments, the rotational assemblies are rotated at a rate of less than 5,000 RPM, less than 4,000 RPM, less than 3,000 RPM, less than 2,000 RPM, less than 1,000 RPM, less than 800 RPM, less than 100 RPM, less than 20 RPM, less than 5 RPM, or less than 1 RPM during the formation of the layers.

In some embodiments, the apparatuses are configured for the polymer containing spinneret to move parallel to the longitudinal axis of the rotational assemblies during formation of one or more layers.

In various aspects, fibrous polymer scaffolds comprising at least a first layer of aligned polymer fibers and a second layer of polymer fibers, wherein the fibers of the second layer are substantially unaligned, and wherein at least one fiber in the first layer of fibers and at least one fiber in the second layer of fibers is the same continuous fiber are disclosed. The first layer of fibers and the second layer of fibers can comprise a single continuous fiber. The first layer of fibers and the second layer of fibers can comprise two continuous fibers. The fibers of the second layers of the scaffolds can have a random orientation. The fibers of the second layers of the scaffolds can be aligned and offset from the alignment of the fibers of the first layer The fibrous polymer scaffolds can be membranes or conduits. The scaffolds can have a shape selected from a square, a rectangle and a circle.

The first layer can be the innermost layer and the second layer can be the outermost layer.

The thickness of both the first layer and the second layer can ranges from about 100 microns to about 500 microns. The thickness of the first layer can be less than the thickness of the second layer.

The polymer fibers comprising any one or more of the layers can comprise a material selected from an aliphatic polyester, a poly(alkylene) oxide, poly(L-lactic acid), 70/30 L-lactide/e-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, poly(ethyl ene-co-vinyl) alcohol, poly(vinyl) alcohol, poly(ethylene) glycol, poly(propylene) glycol, poly-L-lactide-co-glycolide-co-ε-caprolactone, poly(tetrafluoroethylene), poly(dioxanone), polyglactin 910 and combinations thereof.

The aliphatic polyester can be selected from D-lactide, L-lactide, poly(lactic acid), poly(lactide) glycolic acid, poly(glycolic acid), poly(glycolide), glycolide, poly(lactide-co-glycolide), poly(lactic acid-co-glycolic acid), epsilon-caprolactone, poly(epsilon-caprolactone) and a combination thereof. The poly(alkylene) oxide can be selected from poly(ethylene) oxide and poly(propylene) oxide.

The polymer fibers of the first layer and the polymer fibers of the second layer can comprise poly(L-lactide-co-caprolactone). The polymer fibers of the first layer and the polymer fibers of the second layer can comprise poly(L-lactic acid). The polymer fibers of the first layer and the polymer fibers of the second layer can comprise poly(L-lactide-co-caprolactone) and poly(L-lactic acid). One of a plurality of continuous fibers can comprise poly(L-lactide-co-caprolactone) and another of a plurality of continuous fibers can comprise poly(L-lactic acid).

The fibrous polymer scaffolds can also comprise an additive. The additive can be selected from poly(propylene glycol), poly(ethylene oxide), triethyl citrate, glycerol, poly(ethylene glycol), and combinations thereof. The additive can be poly(propylene glycol). The additive can be present in an amount ranging from about 0.1% to about 10% of the total weight of the polymer. The additive can be present in an amount selected from about 1.0% to about 2.0%, about 2.0% to about 3.0%, about 3.0% to about 4.0%, about 4.0% to about 5.0%, about 5.0% to about 6.0%, about 6.0% to about 7.0%, about 7.0% to about 8.0%, about 8.0% to about 9.0%, and about 9.0% to about 10.0% of the total weight of the polymer.

The fibrous polymer scaffolds can also comprise sodium acetate.

In various aspects, kits for the repair of wounds, surgical incisions or biopsies are disclosed, the kits comprising (i) a fibrous polymer scaffold comprising at least a first layer of aligned polymer fibers and a second layer of polymer fibers, wherein the fibers of the second layer are substantially unaligned, and wherein at least one fiber in the first layer of fibers and at least one fiber in the second layer of fibers is the same continuous fiber; and (ii) instructions for using the scaffold to repair wounds, surgical incisions or biopsies by promoting the regeneration of anatomical biological components. The anatomical biological components can be selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, and tendons. The first layer of fibers of the scaffold and the second layer of fibers of the scaffold can comprise a single continuous fiber. The first layer of fibers of the scaffold and the second layer of fibers of the scaffold can comprise two continuous fibers. The fibers of the second layer of the scaffold can have a random orientation. The fibers of the second layer can be aligned and offset from the alignment of the fibers of the first layer. The first layer of the scaffold can be the innermost layer and the second layer can be the outermost layer. The scaffold can be a membrane or a conduit.

In various aspects, methods of implanting fibrous polymer scaffolds are provided, the methods comprising: contacting a defect in a tissue of a subject with a single layer of a fibrous polymer scaffold, the scaffold comprising at least a first layer of aligned polymer fibers and a second layer of polymer fibers, and wherein at least one fiber in the first layer of fibers and at least one fiber in the second layer of fibers is the same continuous fiber, so that the scaffold at least partially replaces the defect. The first layer of fibers and the second layer of fibers can comprise a single continuous fiber. The first layer of fibers and the second layer of fibers can comprise two continuous fibers. The defect can be selected from wounds, surgical incisions and biopsies. The contacting can comprise placing the scaffold over the defect. The contacting can comprise placing the scaffold completely within the defect. The contacting can comprise placing the scaffold underneath the defect. The scaffold can be secured in place at the defect. The securing can comprise suturing the scaffold and/or gluing the scaffold.

In various aspects, fibrous polymer scaffolds are disclosed comprising at least a first layer of aligned polymer fibers and a second layer of polymer fibers having a different alignment than the fibers in the first layer. At least one fiber in the first layer of fibers and at least one fiber in the second layer of fibers can be the same continuous fiber. The first and second layers of fibers can comprise a single continuous fiber. The scaffold can be a hollow conduit. The scaffold can be a filled conduit. The scaffold can be a membrane. In some embodiments, the first layer is not the outermost layer. In some embodiments, the second layer is not the innermost layer. The outer layer can comprise randomly oriented unaligned fibers. The first layer of aligned fibers can be greater than 1 micron and less than 70 microns thick. The first layer of fibers can be greater than 70 microns and less than 150 microns thick. The first layer of fibers can be greater than 150 microns and less than 300 microns thick. The outer layer of fibers can be greater than 150 microns and less than 330 microns thick. The total thickness of all layers can be greater than 20 microns and less than 150 microns. The total thickness of all layers can be greater than 150 microns and less than 250 microns. The total thickness of all layers can be greater than 250 microns and less than 300 microns. The total thickness of all layers can be greater than 300 microns and less than 400 microns. The outer layer can comprise fibers aligned in a direction perpendicular to a direction of the aligned fibers of the first layer.

The fibers can comprise a material selected from the group consisting of aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof. The aliphatic polyester can be selected from the group consisting of D-lactide, L-lactide, poly(lactic acid), poly(lactide) glycolic acid, poly(glycolic acid), poly(glycolide), glycolide, poly(lactide-co-glycolide) or PLGA, poly(lactic acid-co-glycolic acid), epsilon-caprolactone, poly(epsilon-caprolactone), and combinations thereof. The aliphatic polyester can be poly(L-lactide). The aliphatic polyester can be poly(L-lactide-co-caprolactone.

The scaffolds can further comprise an additive. The additive can be selected from triethyl citrate, glycerol, poly(ethylene glycol), poly(propylene glycol), glycerol, and combinations thereof. The additive can be from 0.01% to 25% of the weight of the polymer.

The fibrous polymer scaffolds can comprise a salt selected from NaCl, $KH_2PO_4$, $K_2HPO_4$, $KIO_3$, KCl, $MgSO_4$, MgCl2, NaHCO3, CaCl2, salt of acetic acid, salt of ascorbic acid, salt of citric acid, salt of lactic acid, salt of glycolic acid, and mixtures thereof.

In various aspects, apparatuses for making a fibrous polymer scaffolds are disclosed, comprising (i) a first conducting outer mandrel rotationally associated along a longitudinal axis of the apparatuses within an insulating sleeve, said insulating sleeve rotationally associated along the longitudinal axis of the apparatuses with a second conducting mandrel; and (ii) a charged electrically conducting spinneret configured to release a solution onto the insulating sleeve, said spinneret disposed at a position normal to a point on the longitudinal axis of the apparatus. The sleeve can be configured to be disconnected from the two conducting mandrels and slid over the third conducting mandrel.

In various aspects, apparatuses for making fibrous polymer scaffolds are disclosed, comprising (i) a first, second, and third conducting mandrel rotationally aligned along a longitudinal axis of the apparatuses; (ii) a first insulating region disposed between and rotationally associated with the first and second conducting mandrels; (iii) a second insulating region disposed between and rotationally associate with the second and third conducting mandrels; and (iv) a charged electrically conducting spinneret configured to release a solution onto the insulating sleeve, normal to the longitudinal axis of the apparatuses.

The length of insulating region can be from 5 cm to 10 cm. At least one insulating region can be a hollow tube and the mandrels can be inserted in the tube to form an overlap distance of the tube on each mandrel between 1 mm to 5 mm.

The mandrels can be constructed from stainless steel or aluminum. The insulating region can be constructed from nylon, polyvinyl chloride (PVC) polyvinylidene fluoride (PVDF), polyaryletheretherketone (PEEK), polytetrafluoroethylene (PTFE) or Teflon™.

The first and third conducting mandrels (outer mandrels) can have equal length and the second mandrel can be shorter than the length of each outer mandrel. The first and third mandrels can be charged or grounded, and the second inner mandrel does not have to be grounded.

In various aspects, methods of making multilayer, fibrous polymer scaffolds are disclosed, comprising: electrospinning a polymer at a first rotation rate onto a rotational assembly to form an aligned first fibrous layer; electrospinning a polymer onto the rotational assembly at a second rotation rate without interrupting the flow of the polymer solution to form a non-aligned second fibrous layer, wherein the first fibrous layer and second fibrous layer are comprised of a single fiber. The first rotation rate can be equal to the second rotation rate.

In various aspects, methods of making fibrous polymer scaffolds are provided, comprising: (i) electrospinning a first layer of aligned fibers on an insulating sleeve that is rotationally associated with a first conducting mandrel at a first end of the insulating sleeve and a second conducting mandrel at a second end of the insulating sleeve; (ii) transferring the insulating sleeve with the first layer of aligned fibers onto a third conducting mandrel, wherein the lumen of the sleeve surrounds the third conducting mandrel; and (iii) electrospinning a second layer of non-aligned fibers onto the first layer of aligned fibers.

In various aspects, methods of making fibrous polymer scaffolds are disclosed, comprising: (i) providing a rotational assembly comprising a first, second, and third conducting mandrel rotationally aligned along a longitudinal axis of the assembly, with a first insulating region disposed between and rotationally associated with the first and second conducting mandrels and a second insulating region disposed between and rotationally associate with the second and third conducting mandrels; (ii) providing a charge to the first and second conducting mandrels, and not providing a charge to the inner mandrel; (iii) rotating the rotational assembly to electrospin a first layer of aligned fibers onto a collector substrate comprising the second conducting mandrel; (iv) and rotating the mandrel assembly at the same rotation rate for a period of time sufficient to electrospin a second layer of non-aligned fibers onto the first layer of fibers.

The rotational assembly can be rotated at a rate of 1 to 5,000 revolutions per minute (RPM) during the formation of at least one layer of fibers. The rotational assembly can be rotated at a rate of 20 revolutions per minute (RPM) during the formation of both layers. The rotational assembly can be rotated at a rate of 100 revolutions per minute (RPM) during the formation of at least one layer. The rotational assembly can be rotated at a rate of at least 800 revolutions per minute (RPM) during the formation of at least one layer. The rotational assembly can be rotated at a rate of at least 2000 revolutions per minute (RPM) during the formation of at least one layer.

The rotational assembly can be positioned a distance of 5 cm to 30 cm from a spinneret from which a polymer solution is released. The spinneret can move parallel to the longitudinal axis of the rotational assembly during formation of at least one layer. The rate at which the spinneret can traverse the length parallel to the longitudinal axis of the electrospinning assembly can vary. In some embodiments, the spinneret traverses the length parallel to the longitudinal axis of the electrospinning assembly at a rate of 0 cm/min. In some embodiments, the spinneret traverses the length parallel to the longitudinal axis of the electrospinning assembly at a rate selected from greater than 1 cm/min, greater than 5 cm/min, greater then 10 cm/min, greater than 20 cm/min, greater than 50 cm/min, greater than 100 cm/min, greater than 150 cm/min, greater than 200 cm/min, greater than 250 cm/min, greater than 300 cm/min, greater than 350 cm/min, greater than 400 cm/min, greater than 450 cm/min, or greater than 500 cm/min. In some embodiments, the spinneret traverses the length parallel to the longitudinal axis of the electrospinning assembly at a rate selected from less than 500 cm/min, less than 450 cm/min, less than 400 cm/min, less than 350 cm/min, less than 300 cm/min, less than 250 cm/min, less than 200 cm/min, less than 150 cm/min, less than 100 cm/min, less than 50 cm/min, less than 20 cm/min, less than 10 cm/min, less than 5 cm/min, or less than 1 cm/min.

DETAILED DESCRIPTION

Definitions

Figure 1:
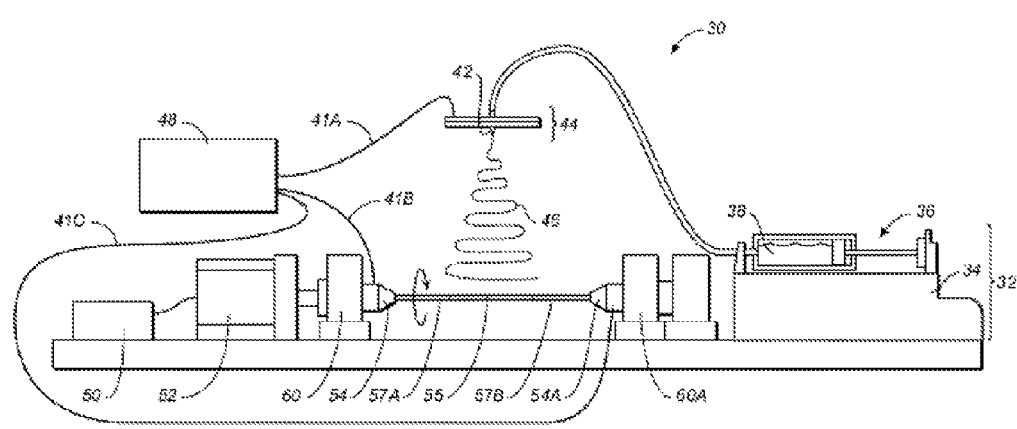
FIG. 1 depicts an electrospinner assembly.

"Aligned" refers to the orientation of fibers in a fibrous polymer scaffold wherein at least 50% of the fibers are oriented in a single direction and their orientation forms an axis of alignment. The orientation of any given fiber can deviate from the average axis of alignment and the deviation can be expressed as the angle formed between the alignment axis and orientation of the fiber. A deviation angle of 0° exhibits perfect alignment and 90° (or −90°) exhibits orthogonal alignment of the fiber with respect to the average axis of alignment. In exemplary embodiments, the standard deviation of the fibers from the average axis of alignment can be an angle selected from between 0° and 1°, between 0° and 3°, between 0° and 5°, between 0° and 10°, between 0° and 20°, or between 0° and 25°. Where the fibers of a layer of a fibrous polymer scaffold are comprised of a single fiber that loops back against itself, the term "aligned" refers to the portion of the fiber inside the terminal end region of the layer where the fiber proceeds back along the axis of alignment.

"Circumferential axis" in the context of a conduit refers to the circumference and/or perimeter of a cross-section of the longitudinal axis of the conduit.

"Conduit" refers to an object that is essentially cylindrical in shape. As used herein, a conduit has an inner wall (lumen) and an outer wall, an interior diameter, an exterior diameter, and an interior space which is defined by the inner diameter of the conduit and its length.

"Filled conduit" refers to a conduit in which at least a portion of the interior space comprises filler material. This filler material can be a fibrous polymer scaffold.

"First axis" in the context of a membrane refers to an axis that is parallel to the longitudinal axis of the collector used to generate the scaffold membrane during electrospinning. The first axis does not necessarily refer to the longest axis of a membrane.

"Longitudinal axis" in the context of a conduit, mandrel or drum refers to an axis that is parallel to the longest axis of the conduit, mandrel or drum, respectively. In the context of a conveyor belt collector, the longitudinal axis is parallel to the long axis of a roller.

"Membrane" refers to an object that is essentially flat, or planar in shape. As used herein, a membrane has at least a first layer of fibers and a second layer of fibers. In varying embodiments, a membrane can have more than two layers of fibers.

"Second axis" in the context of a membrane refers to an axis of the membrane that is perpendicular to the first axis of the membrane. The second axis does not necessarily refer to the shortest axis of a membrane. The second axis does not refer to the thickness of a membrane.

Reference is now made in detail to certain embodiments of scaffolds, methods of use, and methods of making. The disclosed embodiments are not intended to be limiting of the claims. To the contrary, the claims are intended to cover all alternatives, modifications, and equivalents.

Multilayer Fibrous Polymer Scaffolds

The present disclosure relates to multilayer fibrous polymer scaffolds. Scaffolds generally refer to, but are not limited to, hollow conduit or membrane structures formed from polymer microfibers or polymer fibers as described herein. In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of a scaffold is w/w comprised of the polymer fibers as described herein.

Scaffolds can include, without limitation, membrane structures formed from polymer microfibers or nanofibers as described herein. Multilayer polymer scaffolds can be fibrous polymer scaffolds, such as nanofiber polymer scaffolds. The multilayer polymer scaffolds can also be micropatterned polymer scaffolds. The scaffolds of the present disclosure contain at least one layer and can contain a plurality of layers. In some embodiments, the composition has between about 1 and about 10 fibrous layers.

The present disclosure is generally directed to fibrous scaffolds having at least two layers of polymer fibers, apparatuses and methods of their manufacture, methods of use, and kits comprising the scaffolds. Scaffolds of multiple layers of polymer fibers may have multiple differential alignments for each layer, providing tensile strength, suture retention strength, elasticity, flexibility, and rigidity while minimizing delamination of the layers of fibers.

The fibrous scaffolds have specific properties, including the ability to retain a specific shape or geometry, flexibility, and alignment of fiber components in the absence of any non-fiber component. The scaffolds can thus be formed into specific or desired shapes or geometries including, without limitation, conduits, sheets or membranes. The scaffolds may optionally be cut or trimmed into any desired shape or size without any loss of function.

The mechanical integrity of the multilayer polymer scaffolds allow them to be readily suturable, with minimal leak points created from the use of sutures with the scaffolds. Additionally, the multilayer structure of the scaffolds make them sufficiently rigid such that they hold their shape, remain in place at a defect site in a subject, and are not prone to falling apart in the hands of the user, thereby facilitating their use.

The layers of fibers comprising a scaffold can be distinguished by differential alignment of fibers between the layers. For example, in the context of a conduit, the luminal layers of the scaffold may comprise fibers aligned longitudinally, parallel to the longitudinal axis of the scaffold conduit. The outer layers of fibers can be longitudinally aligned, randomly aligned, or circumferentially aligned. For example, in the context of a membrane, the first layers of the scaffold may comprise fibers aligned along a first axis, parallel to the longitudinal axis of the collector used to generate the membranes. The outer layers of fibers can be aligned along a first axis, aligned along a second axis, or unaligned. Different alignment of polymer fibers between different layers can provide additional tensile strength in multiple directions.

In various aspects, a layer of a scaffold can be constructed from a single unbroken polymer fiber, or from a plurality of unbroken polymer fibers. For example, where fibers are aligned longitudinally along a longitudinal axis of a scaffold conduit, the fiber can loop back and forth upon itself during manufacture of the layer. For example, layers of longitudinally aligned fibers in a scaffold conduit traverse a longitudinal axis in the longitudinal direction, and are connected at either end of the scaffold. For example, where fibers are aligned along a first axis of a scaffold membrane, the fiber can loop back and forth upon itself during manufacture of the layer. For example, layers of fibers aligned along a first axis in a scaffold membrane traverse a first axis of the membrane and are connected at either end of the scaffold. As described herein, in certain embodiments, different layers of fibers can be constructed from the same fiber (continuous) or different fibers (discontinuous).

In various aspects, the fibrous scaffolds described herein are produced by electrospinning polymers onto rotational assemblies having two, three, or more mandrels. In some aspects, a two-mandrel device is used to manufacture a polymer scaffold having a first layer of aligned polymer fibers and a second layer that is either unaligned (randomly aligned), circumferentially aligned (in the case of a conduit), or aligned along a second axis (in the case of a membrane).

In various aspects, scaffolds can include more than two layers. In some embodiments, the first and second layers are adjacent, and one or more additional layers can be disposed on the outside of the second layer.

Fibrous layers of polymer fibers may also be aligned in the same direction (or similar unaligned random orientation) continuously or discontinuously. For example, in embodiments with at least two adjacent layers that are formed from discontinuous fibers, each layer can comprise aligned fibers, aligned either along a first axis in the case of a membrane or longitudinally aligned in the case of a conduit, or the second layer can comprise non-aligned fibers. In embodiments where at least two adjacent layers are formed from continuous fibers, the layers can differ in their alignment relative to either the longitudinal axis, in the case of a scaffold conduit, or to a first axis in the case of a scaffold membrane.

In various aspects, the fibrous polymer scaffolds are produced by electrospinning polymers onto rotational assemblies having at least two mandrels, as described below. In some embodiments, a two-mandrel device is used to manufacture polymer scaffolds having a first layer of aligned polymer fibers and a second layer of polymer fibers that is either unaligned (randomly oriented), circumferentially aligned (in the case of a conduit), or aligned along a second axis (in the case of a membrane). In various embodiments, salts may be added to the fibers during electrospinning to facilitate the electrospinning process.

Conduits

In various embodiments, the polymer scaffold has the shape of a conduit. In various embodiments, the polymer scaffold has the shape of a hollow conduit. In various embodiments, the polymer scaffold has the shape of a filled conduit.

A conduit can have a variety of sizes, depending on its length, as well as its inner diameter and outer diameter. In some embodiments, the interior space of the conduit is essentially free of a fibrous polymer scaffold. These parameters can be varied to accommodate, for example, various tissue sizes and applications. In various embodiments, the conduits can have a seam, or can be seamless, as described in PCT Patent Publication WO 2007/146261, the relevant disclosure of which is incorporated herein by this reference. In some embodiments, the first layer (also the inner layer or the luminal layer) of the conduit has longitudinally aligned fibers while the second layer (also the outer layer) of the conduit has unaligned fibers, and at least one fiber between the first and second layers is a single, unbroken fiber. The conduit defined in this instance is designed to display greater structural integrity due to the presence of randomly oriented fibers as an outer sheath.

Multilayer Fibrous Polymer Scaffold Membranes

In some embodiments, the polymer scaffold has the shape of a sheet or membrane. The individual fibers within the membrane can be aligned during electrospinning using a rotating drum as a collector. The individual fibers within a different layer of the membrane can be randomly oriented during electrospinning using a rotating drum as a collector.

In some embodiments, the polymer scaffold has the shape of a "crisscross" sheet. To form a crisscross sheet, first and second layers of aligned polymer sheets or membranes can be arranged in relation to each other, at an angle which is a member selected from greater than 20° but less than 160°, greater than 30° but less than 150°, greater than 40° but less than 140°, greater than 50° but less than 130°, greater than 60° but less than 120°, greater than 70° but less than 110°, and greater than 80° but less than 100°. In various embodiments, two layers share a single, unbroken polymer fiber. In further embodiments, the first and second layers are constructed of a single fiber.

In various aspects, the disclosure relates to multilayer fibrous scaffold membranes. In some embodiments, the scaffolds may comprise at least one biodegradable polymer, one or more salts and, optionally, one or more additives. In some embodiments, the membrane is a shape that is substantially planar or sheet-like, having at least one flat surface. In some embodiments, a scaffold membrane in the shape of a membrane can be of varying thickness, with a homogeneous or a heterogeneous structure and/or composition. In some embodiments, the membrane can be substantially planar or sheet-like with a curvature such that at least one surface is concave or convex.

In various aspects, the scaffold membranes can be used in tissue engineering to improve, regenerate or replace biological tissues. Aligned fibers promote the growth of tissues along the scaffold membranes in the direction of fiber alignment, thereby allowing the scaffold membranes to repair and/or replace a defect in a tissue of a subject. In some embodiments, repairing and/or replacing a defect comprises contacting the scaffold membranes with the defect such that the scaffold membranes patch and/or cover all or any portion of a defect in a patient, thereby taking the place of at least some of the biological tissue that would otherwise be present in the defect. Scaffold membranes of the present disclosure can be used to repair and/or replace a defect when placed on top of a defect, below a defect, or within the physical boundaries of a defect. In some embodiments, scaffold membranes can repair and/or replace a defect when used as an onlay. In some embodiments, scaffold membranes can repair and/or replace a defect when sutured in place. In various embodiments, scaffold membranes of the present disclosure can completely or partially repair and/or replace a defect, at the option of the user.

The scaffold membranes can be configured to resemble the physical tissue structure at the area of treatment, such as dura mater, skin, native collagen fibrils, extracellular matrices, or other tissues as described further herein. By having the scaffold membranes resemble the target tissue in physical properties, growth of that tissue can be enhanced along the average axis of alignment of the polymer fibers of the scaffold membranes. Randomly oriented fibers can provide mechanical integrity to the scaffold membranes by increasing its flexibility, tensility and/or suturability.

Therefore, in several aspects, the fibrous scaffold membranes can be used medically to patch and/or regrow tissue in a subject, particularly in defect areas including, without limitation, surgical wounds, non-surgical wounds, biopsy defects, and areas of tissue damage or trauma.

Multiple Layers; Alignment of Polymer Fibers

Fibrous polymer scaffolds can be made through electrospinning, as described herein. The individual fibers within one or more layers of the scaffolds can be aligned either during electrospinning, as described herein, or after electrospinning by mechanical uniaxial stretching. In several aspects, the individual polymer fibers comprising one or more layers of the scaffolds are aligned during electrospinning.

Each layer can contain fibers in a unique pattern or alignment, wherein each layer of the multilayer polymer scaffolds can optionally be unaligned or aligned. For example, at least one layer may contain aligned fibers and at least one further layer may contain unaligned fibers. In some embodiments, the fibers in a fibrous polymer scaffold are considered aligned when greater than 50%, greater than 60%, greater than 70%, greater than 80%, or greater than 90% of the fibers are oriented in a single direction and their orientation forms an axis of alignment.

In various aspects, a single layer of fibers in a scaffold can be constructed from one, two, three, four, five, or more continuous, unbroken polymer fibers. Similarly, in various aspects a plurality of layers of fibers in a single scaffold can also be constructed from one, two, three, four, five or more continuous, unbroken polymer fibers. Each polymer fiber may be deposited via the use of a spinneret, as described herein. For example, when it is desired for a single layer of a scaffold conduit to have polymer fibers that are aligned longitudinally along a longitudinal axis, the fiber can loop back upon itself. Similarly, when it is desired for a single layer of a scaffold membrane to have polymer fibers that are aligned along a first axis of the membrane, the fiber can loop back upon itself. Where the aligned fibers are comprised of one, two, three or more continuous polymer fibers, each continuous fiber can loop back upon itself to form an aligned layer of fibers. Therefore, conduit layers containing longitudinally aligned fibers contain fibers that traverse a longitudinal axis in the longitudinal direction; the aligned portion of the fibers is located between the terminal end regions of the scaffold, where the fiber proceeds back along the axis of alignment. Similarly, membrane layers containing fibers aligned along a first axis contain fibers that traverse a first axis of the membrane in a direction that is parallel to the longitudinal axis of the collector used to create the scaffold; the aligned portion of the fibers is located between the terminal end regions of the scaffold, where the fiber proceeds back along the axis of alignment.

The layers of fibers in a single scaffold can be distinguished by differential alignment of the fibers composing each of the layers. Each layer of the multilayer polymer scaffolds can have polymer fibers that are aligned or randomly oriented. For example, the first, or innermost, layer of the scaffold conduits may comprise fibers that are aligned longitudinally, parallel to the long axis of the scaffold. A second layer of fibers may comprise fibers that are circumferentially aligned or randomly oriented, thereby providing a difference in the alignment of the fibers between the two exemplary layers. For example, the first layer of the scaffold membranes may comprise fibers that are aligned along a first axis of the membrane, parallel to the long axis of the collector used to generate the membrane. A second layer of fibers may comprise fibers that are aligned along a second axis of the membrane or that are randomly oriented, thereby providing a difference in the alignment of the fibers between the two exemplary layers. The different alignment of polymer fibers between the different layers of the scaffolds provide additional mechanical integrity and tensile strength in multiple directions. In some embodiments, the multilayer scaffolds are designed to display greater structural integrity due to the presence of at least one layer comprising randomly oriented fibers.

The layers of the scaffolds are resistant to delamination, or separation. Each layer of the scaffolds can be comprised of at least one continuous polymer fiber and at least one polymer fiber can also be continuous between the layers of the scaffolds as well, as described herein. The use of continuous fibers between the layers of the scaffolds makes the layers resistant to separation as the polymer chemistry between the layers is similar. The layers thus resist delamination or separation, contributing to the mechanical integrity and strength of the scaffolds. In some embodiments, each layer of the scaffolds comprises two continuous polymer fibers that are also continuous between the layers of the scaffolds. In some embodiments, each layer of the scaffolds comprises continuous fibers of poly(lactide-co-caprolactone) and poly(lactic acid), wherein the fibers are also continuous between the layers of the scaffolds. In some embodiments, each layer of the scaffolds comprises continuous fibers of poly(lactide-co-caprolactone), wherein the fibers are also continuous between the layers of the scaffolds.

Each layer of fibers in a single scaffold may comprise aligned fibers or randomly oriented fibers. For example, in embodiments with at least two adjacent layers that are formed from continuous polymer fibers, each layer can comprise aligned fibers, each layer can comprise non-aligned fibers, each layer can comprise randomly oriented fibers, or the individual layers may comprise differing alignment. The layers of fibers can thus be distinguished by differential alignment of fibers composing the layers. For example, a first layer can comprise aligned fibers and a second layer of fibers can comprise unaligned fibers. In embodiments where at least two adjacent layers are formed from continuous fibers, the layers can differ in their alignment relative to the longitudinal axis of the scaffold conduits, or relative to a first axis of the scaffold membranes. In some embodiments, a first layer of a multilayer polymer scaffold comprises aligned fibers and a second layer of the scaffold comprises randomly oriented fibers, wherein the fibers of the first layer and the fibers of the second layer are formed from at least one continuous polymer fiber.

In various embodiments, a single layer of a scaffold can have an alignment which can be defined relative to at least one axis of the layer. In some embodiments, the scaffold has an asymmetrical shape such as an oval or rectangle. In some embodiments, a single layer of a scaffold having an asymmetrical shape can be defined relative to a long axis of the scaffold. In some embodiments, a single layer of a scaffold having an asymmetrical shape can be defined relative to a short axis of the scaffold. In some embodiments, a scaffold having an asymmetrical shape can have at least one layer of polymer fibers that are aligned essentially parallel to its long axis. In some embodiments, a scaffold having an asymmetrical shape can have at least one layer of polymer fibers that are aligned essentially parallel to its short axis. In some embodiments, fibers can be randomly aligned, or orthogonally aligned, with respect to an axis of the scaffold. In some embodiments, the alignment of fibers in a single layer of a scaffold having an asymmetrical shape may be at an angle relative to either the short axis of the scaffold, or the long axis of the scaffold. In some embodiments, the angle can be from 0° to 90°. In some embodiments, the angle can be from 10° to 80°. In some embodiments, the angle can be from 20° to 70°. In some embodiments, the angle can be from 30° to 60°. In some embodiments, the angle can be from 40° to 50°. In some embodiments, the angle can be 45°.

In some embodiments, a crisscross alignment is present in at least two layers of the scaffolds wherein the fibers of a first layer of a scaffold are aligned in such a manner that the average alignment axis of the first layer is at an angle relative to the average alignment axis of the alignment of the fibers of a second layer of the multilayer polymer scaffold. To form a crisscross arrangement in a multilayer polymer scaffold, first and second layers of aligned polymer fibers can be arranged at an angle relative to each other such that the average axis of alignment of the first layer is offset from the average axis of alignment of a second layer by an angle. In some embodiments, the angle is greater than 20° but less than 160°. In some embodiments, the angle is greater than 30° but less than 150°. In some embodiments, the angle is greater than 40° but less than 140°. In some embodiments, the angle is greater than 50° but less than 130°. In some embodiments, the angle is greater than 60° but less than 120°. In some embodiments, the angle is greater than 70° but less than 110°. In some embodiments, the angle is greater than 80° but less than 100°.

There are a variety of ways to make a crisscross orientation between at least two layers of a multilayer polymer scaffold. In various aspects, a drum is substituted for a mandrel in the various embodiments of the two or three mandrel devices described herein below. In some embodiments, the drum can have a diameter that is greater than or equal to 5 cm, greater than or equal to 6 cm, greater than or equal to 7 cm, greater than or equal to 8 cm, greater than or equal to 9 cm, greater than or equal to 10 cm, greater than or equal to 11, cm, greater than or equal to 12 cm, greater than or equal to 13 cm, greater than or equal to 14 cm or greater than or equal to 15 cm.

In various aspects, scaffolds can include more than two layers. In various aspects, scaffolds can comprise a plurality of layers of fibers. In some embodiments, the first layer of polymer fibers contacts the second layer of polymer fibers, or the first and second layers are adjacent, and one or more additional layers can be disposed on the outside of one of the two layers as a third layer, a fourth layer, a fifth layer, and so on. In other embodiments, one of the plurality of layers in a scaffold can be one or more intervening, non-electrospun, non-polymer and/or non-fibrous layers. In various embodiments, an intervening layer can be an adhesive layer. In some embodiments, the adhesives can be any biocompatible adhesive known in the art. In some embodiments, an intervening layer can provide additional mechanical strength and/or integrity, flexibility, tensility, or other desired properties. In some embodiments, an intervening layer can comprise a molecule or therapeutic compound.

Continuous Fibers in Individual Layers and Between Layers

As described herein, in certain embodiments, different layers of fibers can be constructed from the same fiber (continuous) or different fibers (discontinuous). In various embodiments, all of the layers of the multilayer scaffolds are comprised of a single polymer fiber that is continuous between the layers. In various embodiments, all of the layers of the multilayer scaffolds are comprised of two continuous polymer fibers. It will be understood that the total number of continuous polymer fibers that comprise the layers of the scaffolds can be increased or decreased as may be desired.

In some embodiments, the multilayer fibrous polymer scaffolds are constructed of a plurality of layers that collectively comprise a single, continuous polymer fiber. In other embodiments, the multilayer fibrous polymer scaffolds are constructed of a plurality of layers that collectively comprise at least two, at least three, at least four, or at least five continuous polymer fibers.

In some embodiments, the polymer fibers of a first layer of the scaffolds can be continuous with the polymer fibers of a second layer of the scaffolds. For example, if a two-layer scaffold created from a single polymer is desired, the polymer stream used to create the first layer can be used to create the second layer without stopping the flow of polymer from the spinneret, and thus both layers will be constructed with a single, continuous polymer fiber. In some embodiments, a two-layer scaffold is created from a single polymer, wherein the polymer stream used to create the first layer is used to create the second layer without stopping the flow of polymer from the spinneret, thus both layers are constructed from a single, continuous polymer fiber. In some embodiments, a two-layer scaffold is created from two polymers, wherein the polymer streams used to create the first layer are used to create the second layer without stopping the flow of the polymers from the spinnerets, thus both layers are constructed from two continuous polymer fibers. In some embodiments, a two-layer scaffold is created from three polymers, wherein the polymer streams used to create the first layer are used to create the second layer without stopping the flow of the polymers from the spinnerets, thus both layers are constructed from three continuous polymer fibers. In some embodiments, a two-layer scaffold is created from four polymers, wherein the polymer streams used to create the first layer are used to create the second layer without stopping the flow of the polymers from the spinnerets, thus both layers are constructed from four continuous polymer fibers. In some embodiments, a two-layer scaffold is created from five polymers, wherein the polymer streams used to create the first layer are used to create the second layer without stopping the flow of the polymers from the spinnerets, thus both layers are constructed from five continuous polymer fibers.

In various embodiments, the continuous layers of fibers may be formed of the same polymer solution. In various embodiments, the continuous layers of fibers may be formed of two or more different polymer solutions. A series of different polymer solutions can be sequentially fed through the same tube into the same electrospinner jet to create a continuous flow even while changing the composition of the solution used to spin fibers.

In some embodiments, the layers of fibers may be discontinuous. The discontinuity between fibrous layers may be achieved, for example, by: (i) pausing or stopping the process of fiber formation (i.e., solution flow and/or mandrel rotation) for an amount of time sufficient to break the trajectory of fiber-forming solution and/or cause solvent in the deposited layer to evaporate; and/or (ii) physically cutting or disturbing (i.e., putting objects in the pathway) the jet trajectory of fiber-forming solution with or without stopping the process (i.e., solution flow and/or mandrel rotation).

Non-continuously formed fibrous layers (in addition to continuously formed fibrous layers) may be associated with each other in various degrees depending upon the application desired. The fibrous layers may be randomly intertwined, non-covalently associated, chemically adhered, physically fused, etc. Thus, even though the fibrous layers can be formed in a non-continuous process of more than one electrospinning session, the layers can be made essentially integral.

Polymers, Additives, Salts

A variety of polymers from synthetic and/or natural sources can be used to compose the multilayer fibrous polymer scaffolds. A fiber can be made from a polymer comprising one monomer or subunit or from a polymer comprising a plurality of monomers or subunits. For example, lactic or polylactic acid or glycolic or polyglycolic acid can be utilized to form poly(lactide) (PLA) or poly(L-lactide) (PLLA) nanofibers or poly(glycolide) (PGA) nanofibers. Fibers can also be made from polymers comprising more than one monomer or subunit thus forming a co-polymer, terpolymer, etc. For example, lactic or polylactic acid and be combined with glycolic acid or polyglycolic acid to form the copolymer poly(lactide-co-glycolide) (PLGA). Other copolymers of use in the present disclosure include poly(ethylene-co-vinyl) alcohol.

The polymer(s) may be natural polymers, biological polymers, synthetic polymers, or a combination thereof. In various embodiments, the polymer fibers used to create the scaffolds of the present disclosure are selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In some embodiments, a fiber comprises a single polymer or subunit which is a member selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In some embodiments, a fiber comprises two different polymers or subunits which are members selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In some embodiments, a fiber comprises three different polymers or subunits which are members selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In some embodiments, a fiber comprises four different polymers or subunits which are members selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

In another exemplary embodiment, a fiber comprises five different polymers or subunits which are members selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

The aliphatic polyester can be linear or branched. In some embodiments, the aliphatic polyester is linear and is selected from D-lactic acid, L-lactic acid, lactide, poly(lactic acid), poly(lactide) glycolic acid, poly(glycolic acid), poly(glycolide), glycolide, poly(lactide-co-glycolide), poly(lactic acid-co-glycolic acid), polycaprolactone and combinations thereof. In some embodiments, the aliphatic polyester is branched and is selected from D-lactic acid, L-lactic acid, lactide, poly(lactic acid), poly(lactide) glycolic acid, poly(glycolic acid), poly(glycolide), glycolide, poly(lactide-co-glycolide), poly(lactic acid-co-glycolic acid), polycaprolactone and combinations thereof. In some embodiments, the aliphatic polyester is conjugated to a linker or a biomolecule.

In some embodiments, the polyalkylene oxide is selected from polyethylene oxide, polyethylene glycol, polypropylene oxide, polypropylene glycol and combinations thereof.

The multilayer fibrous polymer scaffolds can comprise a fiber of at least one composition. In some embodiments, the multilayer fibrous polymer scaffolds comprise a number of different types of fibers selected from at least one fiber, at least two fibers, at least three fibers, at least four fibers, at least five fibers, at least six fibers, at least seven fibers, at least eight fibers, at least nine fibers and at least ten fibers.

In some embodiments, the fiber or fibers of the multilayer fibrous polymer scaffolds are biodegradable. In some embodiments, the fibers of the multilayer fibrous polymer scaffolds comprise biodegradable polymers. In some embodiments, the biodegradable polymers comprise a monomer which is a member selected from lactic acid and glycolic acid. In another exemplary embodiment, the biodegradable polymers are poly(lactic acid), poly(glycolic acid) or a copolymer thereof. In some embodiments, the biodegradable polymers are those which are approved by the FDA for clinical use, such as poly(lactic acid) and poly(glycolic acid).

In various aspects, scaffolds comprising biodegradable polymers can be used to guide the morphogenesis of tissue and/or to gradually degrade after the assembly of the tissue. The degradation rate of the polymers can be tailored by one of skill in the art to match the tissue generation rate. For example, if a polymer that biodegrades quickly is desired, a combination of approximately 50:50 polylactic acid to glycolic acid or polyglycolic acid can be selected to form the copolymer poly(lactide-co-glycolide). Additional ways to increase polymer biodegradability can involve selecting a hydrophilic copolymer (for example, polyethylene glycol), decreasing the molecular weight of the polymer, as higher molecular weight often means a slower degradation rate, and decreasing the fiber density in the scaffolds, as lower fiber density can lead to more water absorption and faster degradation.

The tissue can include, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc. In some embodiments, scaffolds comprising biodegradable polymers can be used to guide the morphogenesis of dura mater and gradually degrade after the assembly, repair or replacement of the dura mater. In some embodiments, scaffolds comprising biodegradable polymers can be used to guide the morphogenesis of nerves and gradually degrade after the assembly, repair or replacement of the nerve.

In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of a single layer of a scaffold is w/w comprised of at least one of the polymers described herein.

To improve flexibility and hydrophilic properties of the polymer fibers, an additive may be blended with the polymer. In various embodiments, the additive is present in the scaffold in an amount of from 0.1% to 10% of the total weight of the polymer. In various embodiments, the additive is present in the scaffold in an amount of from 1.0% to 2.0%, from 2.0% to 3.0%, from 3.0% to 4.0%, from 4.0% to 5.0%, from 5.0% to 6.0%, from 6.0% to 7.0%, from 7.0% to 8.0%, from 8.0% to 9.0%, or from 9.0% to 10.0% of the total weight of the polymer. In some embodiments, the additive is 3.1% of the total weight of the polymer. In some embodiments, the additive is 6.2% of the total weight of the polymer.

The additive can be a plasticizer including, but not limited to, triethyl citrate, poly(ethylene glycol), polypropylene glycol), glycerol, and similar materials. In various embodiments, the plasticizer is present in the scaffold in an amount of from 0.1%-25% of the total weight of the polymer.

Poly(propylene glycol) can be used as a plasticizer for certain rigid polymers, including, without limitation, poly(L-lactide-co-caprolactone), it can also be used to increase water uptake into the scaffold and to allow for the formation of a thick layer of unaligned polymer fibers on top of another layer of polymer fibers, such as an aligned fiber layer. In some embodiments, the additive is polypropylene glycol). In some embodiments, the additive is polypropylene glycol) with an average molecular weight between 100-10,000. In some embodiments, the additive is poly(propylene glycol) with an average molecular weight between 100-1,000. In some embodiments, poly(propylene glycol) is blended with the polymer in an amount of from 0.01%-25% of the total weight of the polymer. In some embodiments, poly(propylene glycol) is blended with the polymer in an amount of from 0.01%-10% of the total weight of the polymer.

To improve electrospinning and to decrease the average diameter of the polymer fibers, a dopant may be added to the polymer solution. In various embodiments, the dopant is a salt. Salt produces an excess charge to facilitate the electrospinning process. Salts can include, for example, NaCl, $KH_2PO_4$, $K_2HPO_4$, $KIO_3$, KCl, $MgSO_4$, $MgCl_2$, $NaHCO_3$, $CaCl_2$, $NaCH_3COOH$, as well as salts of organic compounds including, for example, acetic acid, ascorbic acid, citric acid, lactic acid, glycolic acid, and mixtures thereof. In some embodiments, the salt is sodium acetate. In some embodiments, the salt is anhydrous sodium acetate.

In various embodiments, the fibers comprise a copolymer of L-lactide and epsilon-caprolactone, with molar ratios of L-lactide between 40%-90%, and molar ratios of epsilon-caprolactone between 10%-60%. For example, the fibers can comprise a copolymer of L-lactide and epsilon-caprolactone with molar ratios of L-lactide between 50%-80% and molar ratios of epsilon-caprolactone between 20%-50%. In an additional example, the fibers can comprise a copolymer of L-lactide and epsilon-caprolactone with molar ratios of L-lactide between 50%-70% and molar ratios of epsilon-caprolactone between 30%-50%.

In various embodiments, the fibers are formed from polymer solutions, wherein one or more polymers are dissolved in a solvent. In some embodiments, the polymer solution is at least 20% (weight/volume) of poly(L-lactide) dissolved in a solvent. In this embodiment, polymer fibers comprising 100 wt % poly(L-lactide) are formed upon electrospinning.

In some embodiments, the polymer solution is poly(L-lactide), glycerol and sodium acetate dissolved in hexafluoroisopropanol at weight/volume concentrations of 20 wt %, 2 wt % and 0.2 wt %, respectively. In this embodiment, polymer fibers comprising 90 wt % poly(L-lactide are formed), 9 wt % glycerol and 1 wt % sodium acetate are formed upon electrospinning.

In some embodiments, the polymer solution is poly(L-lactide), triethyl citrate, and sodium acetate dissolved in hexafluoroisopropanol at weight/volume concentrations of 25 wt %, 6 wt % and 0.2 wt %, respectively. In this embodiment, polymer fibers comprising 80.1 wt % poly(L-lactide), 19.2 wt % triethyl citrate and 0.7 wt % sodium acetate are formed upon electrospinning.

In some embodiments, the polymer solution is poly(L-lactide-co-caprolactone) (lactide:caprolactone molar ratio: 70:30), poly(propylene glycol) (MW: 425) and sodium acetate dissolved in hexafluoroisopropanol at weight/volume concentrations of 15 wt %, 1 wt % and 0.2 wt %, respectively. In this embodiment, polymer fibers comprising 93 wt % poly(L-lactide-co-caprolactone), 6 wt % poly(propylene glycol) and 1 wt % sodium acetate are formed upon electrospinning.

In some embodiments, the polymer solution is poly(DL-lactide-co-caprolactone)(lactide:caprolactone molar ratio: 85:15) and sodium acetate dissolved in hexafluoroisopropanol at weight/volume concentrations of 20 wt % and 0.2 wt %, respectively. In this embodiment, polymer fibers comprising 99 wt % poly(DL-lactide-co-caprolactone) and 1 wt % sodium acetate are formed upon electrospinning.

In some embodiments, the polymer solution is poly(L-lactide-co-caprolactone) (lactide:caprolactone molar ratio: 70:30) and sodium acetate dissolved in hexafluoroisopropanol at weight/volume concentrations of 15 wt % and 0.2 wt %, respectively. In this embodiment, polymer fibers comprising 99 wt % poly(L-lactide-co-caprolactone) and 1 wt % sodium acetate are formed upon electrospinning.

In some embodiments, the polymer solution is poly(L-lactide), poly(lactide-co-glycolide) and sodium acetate dissolved in hexafluoroisopropanol at weight/volume concentrations of 15 wt %, 15 wt % and 0.2 wt %, respectively. In this embodiment, polymer fibers comprising 49.7 wt % poly(1-lactide), 49.7 wt % poly(lactide-co-glycolide) and 0.6 wt % sodium acetate are formed upon electrospinning.

In some embodiments, the polymer solution is poly(L-lactide) and sodium acetate dissolved in hexafluoroisopropanol at weight/volume concentrations of 28 wt % and 0.2 wt %, respectively. In this embodiment, polymer fibers composed of 99.3 wt % poly(L-lactide) and 0.7 wt % sodium acetate are formed upon electrospinning.

In various embodiments, the polymer fibers of the first layer and the polymer fibers of the second layer of the scaffolds comprise one or more materials selected from an aliphatic polyester, a poly(alkylene) oxide, poly(L-lactic acid), 70/30 poly (L-lactide-co-caprolactone), poly(caprolactone), poly(DL-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, poly (ethylene-co-vinyl) alcohol, poly(vinyl) alcohol, poly(ethylene) glycol, poly(propylene) glycol, poly-L-lactide-co-glycolide-co-ε-caprolactone, poly(tetrafluoroethylene), poly (dioxanone), polyglactin 910 and/or combinations thereof.

In various embodiments, the polymer fibers of the first layer and the polymer fibers of the second layer of the scaffolds comprise one or more materials selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

The aliphatic polyesters can be, for example, lactic acid (D- or L-), lactide, poly(lactic acid), poly(lactide) glycolic acid, poly(glycolic acid), poly(glycolide), glycolide, poly(lactide-co-glycolide), poly(lactic acid-co-glycolic acid), epsilon-caprolactone, poly(epsilon-caprolactone), and/or combinations thereof.

The polyalkylene oxides can be, for example poly(ethylene) oxide, poly(propylene) oxide, and/or combinations thereof.

In some embodiments, the fibers of the first layer and the fibers of the second layer of the scaffolds comprise one or more materials selected from poly(L-lactide-co-caprolactone), poly(L-lactic acid), and/or combinations thereof.

In some embodiments, the first layer of fibers and the second layer of fibers comprise a single continuous polymer fiber comprising poly(L-lactide-co-caprolactone) and poly (propylene glycol). In some embodiments the continuous polymer fiber also comprises sodium acetate. In some embodiments, the continuous fiber comprises 92.6% poly(L-lactide-co-caprolactone), 6.2% poly(propylene glycol) and 1.2% sodium acetate.

Poly (L-lactide-co-caprolactone) is a flexible elastomeric polymer. In various embodiments, poly(propylene glycol) is added to poly (L-lactide-co-caprolactone) as it serves to plasticize poly (L-lactide-co-caprolactone), to increase water uptake into the scaffold membrane, and it allows for the formation of a thicker unaligned fiber layer as a second layer, on top of an aligned fiber layer. Poly (L-lactic acid) is a rigid polymer. In various embodiments, poly(L-lactic acid) is used to provide structural integrity to a scaffold. In some embodiments, a combination of poly (L-lactide-co-caprolactone) polymer fibers and poly(L-lactic acid) polymer fibers is used to generate scaffolds as the use of poly (L-lactic acid) makes the scaffolds more rigid and less elastic than poly (L-lactide-co-caprolactone) with poly(propylene glycol) alone.

In some embodiments, the first layer of fibers and the second layer of fibers comprise two continuous polymer fibers, wherein one of the polymer fibers comprises poly(L-lactide-co-caprolactone), and the other polymer fiber comprises poly(L-lactic acid). In some embodiments, one of the two continuous fibers comprises 100% poly(L-lactide-co-caprolactone). In some embodiments, one of the two continuous fibers comprises 100% poly(L-lactic acid).

In some embodiments, the first layer of fibers and the second layer of fibers comprise a single continuous polymer fiber, wherein continuous fiber comprises poly(L-lactide-co-caprolactone), poly(propylene glycol) and sodium acetate. In some embodiments, the fiber comprises 92.6% poly(L-lactide-co-caprolactone), 6.2% poly(propylene glycol) and 1.2% sodium acetate.

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises poly(L-lactic acid). In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one the two continuous fibers comprises 98.7% poly(L-lactic acid) and 1.3% sodium acetate.

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises poly(glycolic acid). In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one of the two continuous fibers comprises greater than 98% poly(glycolic acid) and less than 2% sodium acetate.

Poly (L-lactide-co-caprolactone) is a flexible elastomeric polymer. In various embodiments, poly(propylene glycol) is added to poly (L-lactide-co-caprolactone) to plasticize poly (L-lactide-co-caprolactone), to increase water uptake into the scaffold membrane, and to generate a thicker unaligned fiber layer as a second layer of the scaffold, on top of an aligned fiber layer.

Poly (glycolic acid) is a rigid polymer. In various embodiments, poly (glycolic acid) is used to provide structural integrity to a scaffold and because it biodegrades quickly.

In some embodiments, a combination of polymer streams of poly (L-lactide-co-caprolactone) with poly(propylene glycol) and poly (glycolic acid) is used to generate scaffolds because the addition of poly (glycolic acid) may operate to make the scaffold more rigid and less elastic than poly (L-lactide-co-caprolactone) with poly(propylene glycol) alone. Additionally, poly(glycolic acid) has a faster rate of biodegradation than poly (L-lactide-co-caprolactone) or poly(L-lactic acid).

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises collagen. In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one of the two continuous fibers comprises greater than 98% collagen and less than 2% sodium acetate.

Collagen is a rigid polymer that is present in a large number of biological tissues. In some embodiments, collagen is used as one of a plurality of polymer fibers comprising the scaffolds to provide structural integrity and because it biodegrades quickly. Collagen also provides cell adhesion regions within the scaffolds.

In some embodiments, a combination of polymer streams of poly(L-lactide-co-caprolactone) with poly(propylene glycol) and collagen is used to generate scaffolds because the addition of collagen may make the scaffolds more rigid and less elastic than poly (L-lactide-co-caprolactone) with poly(propylene glycol) alone. Additionally, because collagen has a faster rate of biodegradation than poly (L-lactide-co-caprolactone), the rate of biodegradation can be tailored to suit several specific uses.

In various embodiments, two polymer streams can be used to generate the multilayer scaffolds. In some embodiments, the two polymer streams comprise a first stream of poly (L-lactide-co-caprolactone) with poly(propylene glycol) and a second stream of poly(L-lactic acid), wherein the relative population of the two polymer fibers may be varied when creating a scaffold. In general, the higher the population of poly(L-lactic acid) fibers, the more rigid the scaffold will be. The higher the population of poly (L-lactide-co-caprolactone) with poly(propylene glycol) fibers, the more elastic the scaffold. In some embodiments, the relative population of the two polymer fibers is selected from: 50% poly (L-lactide-co-caprolactone) with poly(propylene glycol) and 50% poly(L-lactic acid); 90% poly (L-lactide-co-caprolactone) with poly (propylene glycol) and 10% poly(L-lactic acid); 80% poly (L-lactide-co-caprolactone) with poly(propylene glycol) and 20% poly(L-lactic acid); 70% poly (L-lactide-co-caprolactone) with poly(propylene glycol) and 30% poly(L-lactic acid); 60% poly (L-lactide-co-caprolactone) with poly(propylene glycol) and 40% poly(L-lactic acid); 40% poly (L-lactide-co-caprolactone) with poly(propylene glycol) and 60% poly(L-lactic acid); 30% poly (L-lactide-co-caprolactone) with poly(propylene glycol) and 70% poly(L-lactic acid); 20% poly (L-lactide-co-caprolactone) with poly(propylene glycol) and 80% poly(L-lactic acid); and 10% poly (L-lactide-co-caprolactone) with poly(propylene glycol) and 90% poly(L-lactic acid).

In some embodiments, the two polymer streams comprise a first stream of poly (L-lactide-co-caprolactone) with poly (propylene glycol) and a second stream of poly(glycolic acid), wherein the relative population of the two polymer fibers may be varied when creating a scaffold. In general, the higher the population of poly(glycolic acid) fibers, the more rigid the scaffold will be. Additionally, the biodegradation rate increases with an increase in the poly(glycolic acid) population. The higher the population of poly (L-lactide-co-caprolactone) with poly(propylene glycol) fibers, the more elastic the scaffold. In some embodiments, the relative population of the two polymer fibers is selected from: 50% poly (L-lactide-co-caprolactone) with poly(propylene glycol) and 50% poly(glycolic acid); 90% poly (L-lactide-co-caprolactone) with poly(propylene glycol) and 10% poly(glycolic acid); 80% poly (L-lactide-co-caprolactone) with poly(propylene glycol) and 20% poly(glycolic acid); 70% poly (L-lactide-co-caprolactone) with poly(propylene glycol) and 30% poly(glycolic acid); 60% poly (L-lactide-co-caprolactone) with poly(propylene glycol) and 40% poly(glycolic acid); 40% poly (L-lactide-co-caprolactone) with poly(propylene glycol) and 60% poly(glycolic acid), 30% poly (L-lactide-co-caprolactone) with poly(propylene glycol) and 70% poly(glycolic acid); 20% poly (L-lactide-co-caprolactone) with poly(propylene glycol) and 80% poly(glycolic acid); and 10% poly (L-lactide-co-caprolactone) with poly(propylene glycol) and 90% poly(glycolic acid).

In some embodiments, the two polymer streams comprise a first stream of poly (L-lactide-co-caprolactone) with poly (propylene glycol) and a second stream of collagen, wherein the relative population of the two polymer fibers may be varied when creating a scaffold. In general, the higher the population of collagen fibers, the more rigid the scaffold will be. Additionally, the biodegradation rate increases with an increase in the collagen population. The higher the population of poly (L-lactide-co-caprolactone) with poly(propylene glycol) fibers, the more elastic the scaffold. In some embodiments, the relative population of the two polymer fibers is selected from: 50% poly (L-lactide-co-caprolactone) with poly(propylene glycol) and 50% collagen; 90% poly (L-lactide-co-caprolactone) with poly(propylene glycol) and 10% collagen; 80% poly (L-lactide-co-caprolactone) with poly (propylene glycol) and 20% collagen; 70% poly (L-lactide-co-caprolactone) with poly(propylene glycol) and 30% collagen; 60% poly (L-lactide-co-caprolactone) with poly (propylene glycol) and 40% collagen; 40% poly (L-lactide-co-caprolactone) with poly(propylene glycol) and 60% collagen; 30% poly (L-lactide-co-caprolactone) with poly (propylene glycol) and 70% collagen; 20% poly (L-lactideco-caprolactone) with poly(propylene glycol) and 80% collagen; and 10% poly (L-lactide-co-caprolactone) with poly (propylene glycol) and 90% collagen.

Dimensions

The multilayer fibrous polymer scaffolds of the disclosure can have a variety of dimensions which can be varied to suit the needs of a particular application. In various embodiments, the scaffolds are nanofiber polymer scaffolds. Nanofiber polymer scaffolds have submicron-scale features, with each layer comprising polymer fibers having an average fiber diameter of, for example, between 10 nm and 1,000 nm and/or between 50 nm and 1,000 nm. In various embodiments, nanofiber polymer scaffolds can resemble the physical structure at the area of treatment, such as native collagen fibrils or other extracellular matrices.

In various embodiments, the scaffolds are microfiber polymer scaffolds. Microfiber polymer scaffolds have micronscale features, with each layer comprising polymer fibers having an average fiber diameter of, for example, between 1,000 nm and 50,000 nm and/or between 1,000 nm and 20,000 nm. In various embodiments, microfiber polymer scaffolds can resemble the physical structure at the area of treatment, such as native collagen fibrils or other extracellular matrices.

The layers of fibers within a single scaffold may have the same thickness and/or composition with respect to one another. For some embodiments, the thickness and/or composition may be varied within a single layer.

The fiber diameters can vary both between and within layers. In some embodiments, the fiber diameters can vary from 1 nm-10,000 nm. In some embodiments, the fiber diameters can vary from 100 nm-2000 nm. Different fiber diameters may be desirable for different applications. In formulating a desired fiber diameter, one should consider whether any components (i.e., drugs, growth factors, differentiation factors, etc.) will be seeded between fibers and/or the size of any cells expected to be attracted to and deposited along the fibers in vivo.

In some embodiments, the scaffold conduits have a length selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 27 cm, greater than 28 cm, greater than 29 cm, or greater than 30 cm. In some embodiments, the scaffold conduits have a length selected from less than 30 cm, less than 29 cm, less than 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the scaffold conduits have a diameter selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, or greater than 20 cm. In some embodiments, the scaffold conduits have a diameter selected from less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the scaffold membranes have a width selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 27 cm, greater than 28 cm, greater than 29 cm, or greater than 30 cm. In some embodiments, the scaffold membranes have a width selected from less than 30 cm, less than 29 cm, less than 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the scaffold membranes have a length selected from greater than 10 cm, greater than 20 cm, greater than 30 cm, greater than 40 cm, greater than 50 cm, greater than 60 cm, greater than 70 cm, greater than 80 cm, greater than 90 cm, greater than 100 cm, greater than 1 foot, greater than 2 feet, greater than 3 feet, greater than 4 feet, greater than 5 feet, greater than 10 feet, greater than 15 feet, or greater than 20 feet. In some embodiments, the scaffold membranes have a length selected from less than 20 feet, less than 15 feet, less than 10 feet, less than 5 feet, less than 4 feet, less than 3 feet, less than 2 feet, less than 1 foot, less than 100 cm, less than 90 cm, less than 80 cm, less than 70 cm, less than 60 cm, less than 50 cm, less than 40 cm, less than 30 cm, less than 20 cm, or less than 10 cm.

The thickness of the layers of the scaffolds can vary from layer to layer. In various embodiments, the first layer of the scaffolds contains aligned fibers and is thinner than a second layer of the scaffolds, which contains unaligned fibers.

The average wall thickness of the scaffold can also vary. In some embodiments, the thickness of the wall of the scaffolds is from 50-1,000 microns. In some embodiments, the overall wall thickness of the conduit scaffolds is from 100-500 microns.

The thickness or diameter of the polymer fibers can be varied from layer to layer within a single scaffold by controlling several factors. For example, fiber diameter may be decreased by: (i) adding more salt to the polymer solution; (ii) using a more polar solvent in the polymer solution; (iii) increasing the distance between the spinneret(s) and the mandrel; (iv) increasing the voltage; (v) increasing the concentration of the polymer solution; (vi) decreasing the flow rate of the polymer solution; and (vii) increasing the spin rate of the mandrel. See, e.g., U.S. Patent Application Publication No. 2007/0269481 at paragraphs [0027], [0030], [0127], [0139], [0162], [0165], [0176], and [0179]; the entire contents of these paragraphs are incorporated herein by this reference.

In some embodiments, the diameter of the fibers comprising a fibrous polymer scaffold ranges from 1 nm-10,000 nm. In some embodiments, the average diameter of the fibers comprising a fibrous polymer scaffold ranges from 500 nm-1,000 nm. In various embodiments, the average diameter of the fibers is within the range of 10 nm-1,000 nm.

In some embodiments, the average diameter of the fiber or fibers comprising a single layer of a multilayer fibrous polymer scaffold is within a range selected from: 100 nm to 10 microns; 1,000 nm to 20,000 nm; 10 nm to 1,000 nm; 2,000 nm to 10,000 nm; 0.5 nm to 100 nm; 0.5 nm to 50 nm; 1 nm to 35 nm; 2 nm to 25 nm; 90 nm to about 1,000 nm; and 500 nm to 1,000 nm.

In some embodiments, the average diameter of the fiber or fibers comprising a single aligned layer of polymer fibers is within a range selected from: 0.1 microns to 70 microns; 0.1 microns to 60 microns; 0.1 microns to 50 microns; 0.1 microns to 40 microns; 0.1 microns to 30 microns; and 0.1 microns to 25 microns.

In some embodiments, the average diameter of the fiber or fibers comprising a single randomly oriented layer of polymer fibers is within a range selected from: 0.1 microns to 500 microns; 0.1 microns to 400 microns; 0.1 microns to 300 microns; 0.1 microns to 200 microns; and 0.1 microns to 100 microns.

In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of the fibers in a single layer of a scaffold have the same average diameter.

The dimensions of each of the fibrous layers comprising a scaffold can be controlled. In some embodiments, the first layer of a multilayer scaffold comprises aligned polymer fibers and has a thickness ranging from 1 micron to 70 microns. In various embodiments, each layer of a multilayer polymer scaffold has a thickness selected from: greater than 20 microns; greater than 30 microns; greater than 40 microns; greater than 50 microns; greater than 60 microns; greater than 70 microns; greater than 80 microns; greater than 90 microns; greater than 100 microns; greater than 120 microns; greater than 140 microns; greater than 160 microns; greater than 180 microns; greater than 200 microns; greater than 220 microns; greater than 240 microns; greater than 260 microns; greater than 280 microns; and greater than 300 microns.

In various embodiments, the first layer of a multilayer polymer scaffold comprises aligned fibers and has an average thickness selected from: less than 600 microns; less than 580 microns; less than 560 microns; less than 540 microns; less than 520 microns; less than 500 microns; less than 480 microns; less than 460 microns; less than 440 microns; less than 420 microns; less than 400 microns; less than 380 microns; less than 360 microns; less than 340 microns; less than 330 microns; less than 320 microns; less than 300 microns; less than 280 microns; less than 260 microns; less than 240 microns; less than 220 microns; less than 200 microns; less than 180 microns; less than 160 microns; less than 140 microns; less than 120 microns; less than 100 microns; less than 90 microns; less than 80 microns; less than 70 microns; less than 60 microns; less than 50 microns; less than 40 microns; less than 30 microns; and less than 20 microns.

In various embodiments, the total thickness of the entire multilayer polymer scaffold is selected from: greater than 20 microns; greater than 40 microns; greater than 60 microns; greater than 80 microns; greater than 100 microns; greater than 120 microns; greater than 140 microns; greater than 160 microns; greater than 180 microns; greater than 200 microns; greater than 220 microns; greater than 240 microns; greater than 260 microns; greater than 280 microns; greater than 300 microns; greater than 320 microns; greater than 340 microns; greater than 360 microns; greater than 380 microns; greater than 400 microns; greater than 420 microns; greater than 440 microns; greater than 460 microns; greater than 480 microns; greater than 500 microns; greater than 520 microns; greater than 540 microns; greater than 560 microns; greater than 580 microns; and greater than 600 microns.

Therapeutic Uses

The fibrous polymer scaffolds can be used in any manner known in the art. These uses can include, without limitation, uses as tissue substitutes and/or tissue regeneration matrices for wounds and/or defects in biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc., uses in combination with cells, uses in combination with biomolecules, and uses in combination with pharmaceutically acceptable excipients, as described in PCT Publication No. WO 2007/090102, the relevant disclosure of which is incorporated herein by reference in its entirety. Similarly, uses in compositions, and as grafts for nerves, skin, vascular tissue, and muscle may be used as described in PCT Publication No. WO 2007/090102, the relevant disclosure of which is incorporated herein by reference in its entirety.

An aligned layer of polymer fibers can affect cell alignment, cell migration and cellular function. Aligned polymer fibers can induce and direct cell migration along the direction of the average axis of alignment of a layer of a scaffold, thus enhancing tissue regeneration in such a direction.

The aligned polymer fibers function by first promoting directed outgrowth of tissue in contact with the aligned fibers and second by continuously guiding the regenerating tissue in the direction of the axis of alignment of the aligned fibers. Therefore, when placed in contact with a wound or defect, a layer of aligned polymer fibers promotes healing by promoting directed outgrowth of tissue in contact with the aligned fibers at the periphery of the wound or defect and by continuously guiding the regenerating tissue across the wound or defect gap along the direction of the axis of alignment of the aligned fibers.

Therefore, aligned layers of polymer fibers can be used to help regenerate a variety of tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc. For example, an aligned layer of a multilayer fibrous polymer scaffold can enhance and specifically direct the growth of biological tissues across an injury gap, along the average axis of alignment of the polymer fibers. In some embodiments, the scaffolds can be used in this manner to affect rapid cell and/or tissue coverage within a wound or defect area.

The scaffolds can be sized to completely cover, or to partially cover, a wound or defect gap in a tissue. In some embodiments, the scaffolds are cut or trimmed into a desired shape and sized to completely cover, or to partially cover, a wound or defect. In various embodiments, the scaffolds are used to bridge long injury gaps. In some embodiments, defect gaps to be bridged can have a length selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm, greater than 35 cm, greater than 40 cm, greater than 45 cm, or greater than 50 cm. In some embodiments, defect gaps to be bridged can have a length selected from less than 50 cm, less than 45 cm, less than 40 cm, less than 35 cm, less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, defect gaps to be bridged can have a width selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm, greater than 35 cm, greater than 40 cm, greater than 45 cm, or greater than 50 cm. In some embodiments, defect gaps to be bridged can have a width selected from less than 50 cm, less than 45 cm, less than 40 cm, less than 35 cm, less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

The wound or defect area can be asymmetrical, having a long axis and a short axis. In various embodiments, the scaffolds can be contacted with an asymmetrical wound or defect such that the average axis of alignment in a layer of aligned fibers in the scaffold is oriented parallel to the short axis of the wound or defect, to promote rapid cell ingrowth and coverage of the defect or wound.

The direction in which a layer comprising aligned polymer fibers is situated relative to a wound or defect area in a subject can affect the biological function that the aligned polymer fibers are replacing or improving. For instance, when a wound is contacted with an aligned layer of a multilayer polymer scaffold, it is believed that the rate of healing is increased when the aligned layer of the polymer scaffold is perpendicular, rather than parallel, to the long axis of the wound.

In some embodiments, the central long axis of an aligned layer of a multilayer fibrous polymer scaffold is situated parallel to the direction of the material which the aligned polymer scaffold is improving or replacing. In another exemplary embodiment, the central long axis of an aligned layer of a multilayer fibrous polymer scaffold is situated perpendicular to the direction of the material which the aligned polymer scaffold is improving or replacing. In some embodiments, wound healing occurs as the tissue interfaces with the aligned fibers of a layer of the scaffold and grows along the average axis of alignment.

In various embodiments, the tissue in which a wound or defect exists has an inherent alignment. Tissues with an inherent alignment include, without limitation, nerves, spinal cord, brain, tendons, ligaments, blood vessels, muscles, and other tissues. In some embodiments, the scaffolds can be contacted with a defect or wound in a tissue having an inherent alignment such that the average axis of alignment in a layer of aligned fibers in the scaffolds is oriented parallel to the tissue's axis of alignment to promote cell or tissue ingrowth along the alignment of the native tissue.

In several aspects, multilayer fibrous polymer scaffolds can be contacted with a subject to replace, regenerate or improve a biological function and/or a biological tissue. In some embodiments, the scaffolds replace, regenerate or improve the structure and/or function of a biological tissue, wherein the biological tissue is selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, and other biological tissues in a subject.

In several aspects, the present disclosure provides methods of treating an injury or defect in a subject, the methods comprising contacting the subject with a therapeutically effective amount of the scaffolds of the disclosure, sufficient to treat the injury or defect. A therapeutically effective amount is an amount of contact between a scaffold and a subject sufficient to provide the desired local or systemic effect or to effect the desired therapeutic result. In some embodiments, the subject is contacted with one or more scaffolds at the site of the injury or defect. In some embodiments, the defect or injury is selected from wounds, defects arising due to disease, defects arising due to infection, surgical incisions and/or biopsies; the foregoing can include, without limitation, a severed meninx, a damaged meninx, severed fascia, damaged fascia, a severed nerve, a damaged nerve, a severed muscle, a damaged muscle, a severed blood vessel, a damaged blood vessel, a skin wound and bruised skin.

In several aspects, the present disclosure provides methods of growing tissue in a subject, the methods comprising contacting the subject with a therapeutically effective amount of a scaffold disclosed herein, sufficient to facilitate growth of the tissue. In some embodiments, the tissue is a biologically-simple connective tissue having a sheet-like architecture. In some embodiments, the tissue is a member selected from meninx tissue, fascia, skin tissue, cardiac tissue, gastrointestinal tissue, stomach tissue, tissue of the abdominal wall, muscle tissue, vascular tissue, nerve tissue, and similar tissues. In some embodiments, the tissue is a biological tissue selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, and other biological tissues. The tissue interfaces with the aligned fibers of a layer of the scaffold and grows along the average axis of alignment.

In several aspects, the present disclosure provides methods of treating an injury or defect in a subject, the methods comprising contacting the defect or injury in a subject with a fibrous polymer scaffold such that the scaffold at least partially replaces the defect or injury. The scaffolds of the present disclosure can be used in vitro or in vivo to test for their efficacy.

Scaffolds are suitable for use with a variety of subjects. In some embodiments, the subject is an animal. In some embodiments, the animal is selected from a human, a dog, a cat, a horse, a rat and a mouse.

In several aspects, aligned layers of polymer fibers comprise biodegradable polymers. These layers can be used to guide the morphogenesis of tissue types having anisotropic structure, e.g., biological tissues such as nerve, skin, blood vessel, skeletal muscle, cardiac muscle, tendon and ligament. These aligned layers can also be used in the development of three-dimensional tissue constructs. Using the scaffolds described herein, three-dimensional constructs of nerve tissue, spinal cord tissue, skin tissue, vascular tissue, muscle tissue, and many other tissues can be created.

Multilayer fibrous polymer scaffolds of the present disclosure have numerous characteristics that are useful in wound healing. For example, the scaffolds can be both nano-porous and breathable, thus preventing microbes and infectious particles from crossing through to the wound or defect, while allowing air flow and moisture penetration, which are important to natural wound healing. Additionally, in some embodiments the polymer fibers comprising the scaffolds are biodegradable, which allows for temporary wound coverage followed by eventual ingrowth of new tissue.

The materials comprising the scaffolds can be varied to approximate the characteristics of natural tissue including, for example, mechanical strength, rate of degradation, and rate of tissue regeneration.

The scaffolds of the present disclosure are useful for clinical and personal wound care and soft tissue regeneration. In some embodiments, a multilayer polymer scaffold can be used as a wound dressing or as a graft to treat external skin wounds. In a clinical setting, the scaffolds can be used to treat wounds resulting from trauma, burns, ulcers, abrasions, lacerations, surgery, or other damage or trauma. A user can use the scaffolds to cover and protect the wound area, to temporarily replace lost or damaged skin tissue, and to guide new tissue generation and wound healing into the damaged area. The scaffolds can be used as an onlay, or may be secured to the wound area using sutures, adhesives, or overlaying bandages. The scaffolds may be cut to match the size of the wound, or may overlap the wound edges.

The scaffolds may be tailored for personal/home care by combining the scaffold with an adhesive to create a multilayer polymer scaffold bandage. The adhesive can serve to hold the scaffold in place on a wound or defect area and can be removed when the fibers degrade or fuse with the tissue. The scaffolds may be secured with any suitable adhesive including, for example, liquid or gel adhesives.

Large sized scaffolds can be used as gauze to absorb fluid and protect large wounds or defects. When used in this manner, the scaffolds can be wrapped around a wounded area, secured with tape, or with secondary bandages.

The scaffolds can be used to treat internal soft tissue wounds or defects in biological tissues including, without limitation, the amniotic sac, ulcers in the gastrointestinal tract or mucous membranes, gingival damage or recession, internal surgical incisions or biopsies, etc. The scaffolds can be used as an onlay or may be sutured or adhered into place to fill or cover the damaged tissue area. The nano-scale architecture of nanofibrous scaffolds closely mimics the architecture of the extracellular matrix of many common soft tissues. For example, nano-scale polymer fibers are structurally similar to collagen fibrils found in skin and other tissues. This architecture may prevent scar formation in a wound or defect by providing an organized, aligned layer of a scaffold for cells to migrate into a wound.

Aligned polymer fibers in the scaffolds can be used to keep cells aligned and organized during regrowth into the defect or wound area, rather than allowing them to arrange randomly. Random arrangement of cells typically results in the formation of scar tissue and thus the scaffolds may be used to minimize the formation of scar tissue.

Aligned polymer fibers may be oriented with respect to a given axis of the wound, or with respect to the inherent alignment of a type of tissue, to allow faster tissue ingrowth and wound coverage.

Polymer scaffold alignment can also be used to closely match the architecture of natural tissue extracellular matrix.

In several embodiments, a molecule is covalently attached, either directly or through a linker, to the fibrous polymer scaffolds, and the molecule is capable of either covalently or non-covalently attaching to a member selected from an extracellular matrix component, a growth factor, a differentiation factor and combinations thereof. In some embodiments, the molecule is covalently attached to the scaffold through a linker, and the linker is selected from di-amino poly(ethylene glycol), poly(ethylene glycol) and combinations thereof. The molecule can be structural or alternatively can be related to a tissue. In some embodiments, the extracellular matrix component is selected from laminin, collagen, fibronectin, elastin, vitronectin, fibrinogen, polylysine and combinations thereof. In some embodiments, the growth factor is selected from acidic fibroblast growth factor, basic fibroblast growth factor, nerve growth factor, brain-derived neurotrophic factor, insulin-like growth factor, platelet derived growth factor, transforming growth factor beta, vascular endothelial growth factor, epidermal growth factor, keratinocyte growth factor and combinations thereof. In some embodiments, the differentiation factor is selected from stromal cell derived factor, sonic hedgehog, bone morphogenic proteins, notch ligands, Wnt and combinations thereof. Molecules can also be incorporated with the scaffolds either during electrospinning or post-fabrication. The molecules can be incorporated via blending, direct covalent attachment, attachment through various linkers, or by adsorption. In some embodiments, the molecules are organic molecules typically made by living organisms. In some embodiments, the molecules are selected from nucleotides, amino acids, sugars, fatty acids, steroids, nucleic acids, polypeptides, peptides, peptide fragments, carbohydrates, lipids, and combinations thereof (e.g., glycoproteins, ribonucleoproteins, lipoproteins, or the like). In some embodiments, the molecules are selected from receptor molecules, extracellular matrix components or biochemical factors. Biochemical factors can include, for example, growth factors or differentiation factors. In some embodiments, the molecule is selected from glycosaminoglycans and proteoglycans.

The following are examples of certain specific uses of the scaffolds of the disclosure and are not intended to be limiting. Rather, the present disclosure is intended to include uses of the disclosed polymer scaffolds with a plurality of biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc.

Uses Involving Meninges

In some embodiments, the scaffolds are used to repair a severed or damaged meninx, or one or more severed or damaged meninges. One use is for the regeneration of damaged dura mater. The dura mater is a membrane that surrounds the brain and spinal cord. It is the outermost of the three meninges, which help protect the brain and spinal cord and provide a retention barrier for the cerebrospinal fluid. In a normal subject, the dura mater is attached directly to the skull, or to the bones of the vertebral canal in the spinal cord. Damage to the dura mater can be caused by trauma, surgical incisions, subdural hematoma, epidural hematoma, meningitis, meningiomas, tumor involvement, etc. The tissue of the dura mater is capable of repair and/or regeneration but it is unable to do so efficiently over large gaps or defects.

The scaffolds described herein can serve as replacements for all known dural graft matrices, such as xenogeneic collagen-based dural graft substitutes, which are currently a popular form of treatment for dura mater defects.

In some embodiments, the scaffolds may be used to repair the dura mater at one or more locations where it is damaged or otherwise contains a defect and is no longer in continuity. The scaffolds may be used in all situations involving discontinuous and/or damaged dura mater. In some embodiments, the scaffolds are used where the defect gap is large enough to either greatly hinder or prevent direct regeneration of the dura mater. In some embodiments, the scaffolds are contacted with a defect gap in the dura mater and at least partially bridge the defect gap to enhance and direct the regeneration of dura mater across the defect gap.

In some embodiments, the scaffolds are placed and/or contacted with a defect gap such that a single layer of a scaffold, comprising aligned polymer fibers, contacts the defect site and the remaining layers of the scaffold do not contact the defect. In some embodiments, the aligned fibers in contact with the defect are essentially parallel to the tissue fibers of the dura mater to allow the aligned fibers to provide specific guidance cues that direct the regenerating dura mater efficiently along the aligned layer and across the defect gap.

In various embodiments, the scaffolds are used as an onlay either on top of, or underneath, the dura mater to bridge the wound or defect. In some embodiments, the scaffolds are inserted directly into the wound or defect. In some embodiments, the scaffolds are put in contact with a wound or defect so that a layer of aligned fibers contacts the wound or defect. In some embodiments, the scaffolds are sutured in place.

In various embodiments, the polymer content of the scaffolds is adjusted to match the architecture and physical properties of the dura mater. Dura mater is composed mainly of collagen and elastic fibers embedded in an amorphous extracellular substance. Various studies have observed the tensile strength of human cranial and spinal dura mater as being between 6-20 MPa (see, e.g., J. Neurosurg. 86:1012-1017 (1997); J. Biomech. Eng. 4:541-544 (1998); and Anesth. Analg. 88:1317-21 (1999)). The dura mater is also characterized as being tough, inelastic and flexible. In some embodiments, the scaffolds are created to have the tensile strength, elasticity and flexibility similar to that of human dura mater by comprising at least two continuous polymer fibers, wherein the first of the two continuous fibers comprises poly(L-lactide-co-caprolactone) plus polypropylene glycol) the second of the two continuous fibers comprises poly(L-lactic acid), and both fibers further comprise sodium acetate. In some embodiments, the scaffolds are created to have the tensile strength, elasticity and flexibility similar to that of human dura mater by comprising at least two continuous polymer fibers, wherein both of the continuous fibers comprise poly(L-lactide-co-caprolactone) plus poly(propylene glycol) and sodium acetate.

Uses Involving Fascia

In some embodiments, the scaffolds are used to replace severed or damaged fascia. One use is for the regeneration of damaged fascia. Fascia comprises both superficial fascia and deep fascia. In a normal subject, superficial fascia surrounds organs, glands and neurovascular bundles, fills otherwise unoccupied space in the subject's body and can serve to store fat and water, can serve as a passageway for lymph, nerve and blood vessels, and can act as a protective padding. In a normal subject, deep fascia interpenetrates and surrounds the muscles, bones, nerves and blood vessels of the body where it serves to protect and insulate these structures. Damage to the fascia can be caused by trauma, surgical incisions, tumor involvement, etc. The tissue of fascia is capable of repair and/or regeneration but it is unable to do so efficiently over large gaps or defects.

The scaffolds described herein can serve as a replacement for all known means of fascia repair including surgical sutures, which are currently a popular form of treatment for fascia defects but are far from perfect.

In some embodiments, the scaffolds may be used to repair fascia at one or more locations where it is damaged or otherwise contains a defect and is no longer in continuity. The scaffolds may be used in all situations involving discontinuous and/or damaged fascia. In some embodiments, the scaffolds are used where the defect gap is large enough to either greatly hinder or prevent direct regeneration of fascia. In some embodiments, the scaffolds are contacted with a defect gap in fascia and at least partially bridge the defect gap to enhance and direct the regeneration of fascia across the defect gap.

In some embodiments, the scaffolds are placed and/or contacted with a defect gap such that a single layer of a scaffold, comprising aligned polymer fibers, contacts the defect site and the remaining layers of the scaffold do not contact the defect. In some embodiments, the aligned fibers in contact with the defect are essentially parallel to the tissue fibers of the fascia to allow the aligned fibers to provide specific guidance cues that direct the regenerating fascia efficiently along the aligned layer and across the defect gap.

In various embodiments, the scaffolds are used as an onlay either on top of, or underneath, the fascia in order to bridge the wound or defect. In some embodiments, the scaffolds are inserted directly into the wound or defect. In some embodiments, the scaffolds are put in contact with a wound or defect so that a layer of aligned fibers contacts the wound or defect. In some embodiments, the scaffolds are sutured in place.

In various embodiments, the polymer content of the scaffolds is adjusted to match the architecture and physical properties of fascia. Fascia is composed mainly of collagen and the amount of elastin fibers included in the fascia determines the level of extensibility and resilience the fascia will have. Other collagen-rich soft tissues, such as tendons, ligaments, and skin, display mechanical properties that strongly depend on the collagen fiber quantity and orientation. Accordingly, the mechanical properties of fascia can correlate to the underlying dense collagen structure. The observed elastic spring constant for collagen in humans is generally about 3.7 GPa-about 4.0 GPa. In some embodiments, the polymer content of the scaffolds is adjusted to closely match an elastic spring constant of about 3.7 GPa-about 4.0 GPa. In some embodiments, the polymer content of the scaffolds is adjusted to closely match the physical properties of collagen. In some embodiments, the physical properties of collagen may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the physical properties of collagen may be matched in a scaffold that comprises at least one continuous polymer fiber, wherein the continuous fiber comprises poly(L-lactide-co-caprolactone) plus poly(propylene glycol) and sodium acetate.

Uses Involving Skin

In some embodiments, the scaffolds are used to replace damaged skin. One use is for the regeneration of damaged skin. The skin is the outer covering of the body of an animal and is also known as the epidermis. The skin is the largest organ of the integumentary system and is made up of multiple layers of epithelial tissues. Damage to the skin can be caused by trauma, surgical incisions, tumor involvement, etc. The skin is capable of repair and/or regeneration but it is unable to do so efficiently over large gaps or defects without creating scar tissue.

The scaffolds described herein can serve as a replacement for all known means of skin repair including, without limitation, surgical sutures or stitches, adhesive bandages, gauze bandages, and synthetic skin replacements, each of which are currently popular forms of treatment for skin defects but are far from perfect.

In some embodiments, the scaffolds may be used to repair skin at one or more locations where it is damaged or otherwise contains a defect and is no longer in continuity. The scaffolds may be used in all situations involving discontinuous and/or damaged skin. In some embodiments, the scaffolds are used where the defect gap is large enough to either greatly hinder or prevent direct regeneration of skin without the generation of scar tissue. In some embodiments, the scaffolds are contacted with a defect gap in skin and at least partially bridge the defect gap to enhance and direct the regeneration of the skin across the defect gap.

In some embodiments, the scaffolds are placed and/or contacted with a defect gap such that a single layer of a scaffold, comprising aligned polymer fibers, contacts the defect site and the remaining layers of the scaffold do not contact the defect. In some embodiments, the aligned fibers in contact with the defect are essentially parallel to the tissue fibers of the skin to allow the aligned fibers to provide specific guidance cues that direct the regenerating skin efficiently along the aligned layer and across the defect gap.

In various embodiments, the scaffolds are used as an onlay either on top of, or underneath, the skin in order to bridge the wound or defect. In some embodiments, the scaffolds are inserted directly into the wound or defect. In some embodiments, the scaffolds are put in contact with a wound or defect so that a layer of aligned fibers contacts the wound or defect. In some embodiments, the scaffolds are sutured in place. In some embodiments, the scaffolds are held in place via the use of secondary bandages. In some embodiments, the scaffolds are held in place by adhesives.

In various embodiments, the polymer content of the scaffolds is adjusted to match the architecture and physical properties of the skin. The underlying structure of skin is composed primarily of collagen. Other collagen-rich soft tissues, such as tendons and ligaments, display mechanical properties that strongly depend on the collagen fiber quantity and orientation. Accordingly, the mechanical properties of skin can correlate to the underlying collagen structure. The observed elastic spring constant for collagen in humans is generally about 3.7 GPa-about 4.0 GPa. In some embodiments, the polymer content of the scaffolds is adjusted to closely match an elastic spring constant of about 3.7 GPa-about 4.0 GPa. In some embodiments, the polymer content of the scaffolds is adjusted to closely match the physical properties of skin. In some embodiments, the physical properties of skin may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the physical properties of skin may be matched in a scaffold that comprises at least one continuous polymer fiber, wherein the continuous fiber comprises poly(L-lactide-co-caprolactone) plus poly(propylene glycol) and sodium acetate.

Uses Involving Cardiac Tissue

In some embodiments, the scaffolds are used to replace damaged cardiac tissue. One use is for the regeneration of damaged cardiac tissue. Cardiac tissue is primarily a highly oxidative, striated muscle tissue composed of cardiac myocytes. Damage to cardiac tissue can be caused by trauma, surgical incisions, tumor involvement, myocardial infarction, coronary heart disease, cardiomyopathy, ischemic heart disease, etc. Cardiac tissue is capable of repair and/or regeneration but it is unable to do so efficiently over large gaps or defects.

The scaffolds described herein can serve as a replacement for known means of cardiac tissue repair including surgical sutures, which are currently a popular form of treatment for defects of cardiac tissue but are far from perfect.

In some embodiments, the scaffolds may be used to repair cardiac tissue at one or more locations where it is damaged or otherwise contains a defect and is no longer in continuity. The scaffolds may be used in all situations involving discontinuous and/or damaged cardiac tissue. In some embodiments, the scaffolds are used where the defect gap is large enough to either greatly hinder or prevent direct regeneration of cardiac tissue. In some embodiments, the scaffolds are contacted with a defect gap in cardiac tissue and at least partially bridge the defect gap and enhance and direct the regeneration of cardiac tissue across the defect gap.

In some embodiments, the scaffolds are placed and/or contacted with a defect gap such that a single layer of a scaffold, comprising aligned polymer fibers, contacts the defect site and the remaining layers of the scaffold do not contact the defect. In some embodiments, the aligned fibers in contact with the defect are essentially parallel to the tissue fibers of the cardiac tissue to allow the aligned fibers to provide specific guidance cues that direct the regenerating cardiac tissue efficiently along the aligned layer and across the defect gap.

In various embodiments, the scaffolds are used as an onlay either on top of, or underneath, the cardiac tissue in order to bridge the wound or defect. In some embodiments, the scaffolds are inserted directly into the wound or defect. In some embodiments, the scaffolds are put in contact with a wound or defect so that a layer of aligned fibers contacts the wound or defect. In some embodiments, the scaffolds are sutured in place.

In various embodiments, the polymer content of the scaffolds is adjusted to match the architecture and physical properties of cardiac tissue. Cardiac tissue is composed mainly of the proteins actin and myosin. Accordingly, the mechanical properties of cardiac tissue can correlate to the average properties of both actin and myosin. The observed elastic modulus of the lateral wall of the myocardium has been shown to be about 3.40 kPa-3.78 kPa. In some embodiments, the polymer content of the scaffolds can be adjusted to closely match an elastic modulus of about 3.40 kPa-3.78 kPa. In some embodiments, the polymer content of the scaffolds can be adjusted to closely match the physical properties of cardiac tissue. In some embodiments, the physical properties of cardiac tissue may be matched in a scaffold that comprises at least two continuous polymer fibers, wherein the first of the two continuous fibers comprises poly(L-lactide-co-caprolactone) plus polypropylene glycol) the second of the two continuous fibers comprises poly(L-lactic acid), and both fibers further comprise sodium acetate. In some embodiments, the physical properties of cardiac tissue may be matched in a scaffold that comprises at least one continuous polymer fiber, wherein the continuous fiber comprises poly(L-lactide-co-caprolactone) plus polypropylene glycol) and sodium acetate.

Uses Involving Nerves

In various embodiments, the polymer content of the fibrous polymer scaffolds can be adjusted to mimic the architecture and physical properties of nerves. Most mammalian nerves are bundles of individual neural cells surrounded by one or more sheaths of dense, protective connective tissue. The protective connective tissue can include, for example, the endoneurium, the perineurium and the epineurium. The perineurium comprises fascia-like connective tissue and has a distinctly lamellar arrangement consisting of approximately 7-8 concentric layers. Fascia is composed mainly of collagen, together with a varying amount of elastin that determines the level of extensibility and resilience the fascia will have. Most collagen-rich soft tissues, such as tendons, ligaments, and skin, display mechanical properties that strongly depend on the collagen fiber quantity and orientation. Accordingly, the mechanical properties of fascia can be directly correlated to the underlying dense collagen structure. The observed elastic spring constant for collagen in humans is from about 3.7 GPa to about 4.0 GPa, though this value can change with various factors, such as the age of the body the collagen was harvested from, and pH. In some embodiments, the polymer content of the scaffolds can be adjusted to closely match an elastic spring constant of from about 3.7 GPa to about 4.0 GPa. In some embodiments, the polymer content of the scaffolds can be adjusted to closely match the physical properties of nerves.

In some embodiments, the physical properties of nerves may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, at least one of the continuous polymer fibers comprises about 92.6% poly(L-lactide-co-caprolactone), about 6.2% poly(propylene glycol) and about 1.2% sodium acetate and at least another of the two continuous polymers fibers comprises about 98.7% poly(L-lactic acid) and about 1.3% sodium acetate. In various embodiments, the at least two continuous polymer fibers comprise any one or more of the polymers disclosed herein and can optionally include an additive and/or a salt.

In some embodiments, the physical properties of nerves may be matched in a scaffold that comprises at least one continuous polymer fiber, wherein the continuous fiber comprises poly(L-lactide-co-caprolactone) plus poly(propylene glycol) and sodium acetate. In some embodiments, at least one of the continuous polymer fibers comprises about 92.6% poly(L-lactide-co-caprolactone), about 6.2% poly(propylene glycol) and about 1.2% sodium acetate. In various embodiments, the at least two continuous polymer fibers comprise any one or more of the polymers disclosed herein and can optionally include an additive and/or a salt.

Implantation of the Scaffolds

In various aspects, methods of implanting fibrous polymer scaffolds are provided. The scaffolds may be implanted into a subject according to any method known in the art. These methods include, without limitation, implantation by topical application (e.g. non-invasive implantation such as by placing a scaffold on the surface of the skin), onlay implantation, sutured implantation, and other methods. In various embodiments, the scaffolds can be implanted using the methods described in Zerris, et al., "Repair of the Dura Mater With Processed Collagen Devices", *Journal of Biomedical Materials Research Part B: Applied Biomaterials*, published online 26 Apr. 2007 in Wiley InterScience (www.interscience.wiley.com). DOI: 10.1002/jbm.b.30831, which is incorporated herein by reference in its entirety. In various embodiments, the scaffolds can be implanted using the methods described in Mello et al., "Duraplasty with biosynthetic cellulose: An experimental study", *J. Neurosurg.*, 86: 143-150 (1997), which is incorporated herein by reference in its entirety.

In some embodiments, methods of implanting scaffolds comprise contacting a wound, injury or defect in a tissue of a subject with a scaffold. In some embodiments, methods of implanting scaffolds comprise contacting a wound, injury or defect in a tissue of a subject with a single layer of a fibrous polymer scaffold. In some embodiments, the polymer fibers comprising the layer in contact with the wound, injury or defect are aligned. In some embodiments, the scaffold in contact with the wound, injury or defect at least partially replaces the defect. In some embodiments, the scaffold in contact with the wound, injury or defect completely replaces the defect.

In various embodiments, methods of implanting scaffolds comprise contacting a wound, injury or defect with one or more scaffolds in an amount, and under conditions, sufficient to treat the injury. In some embodiments, the amount of scaffolds is the amount necessary to at least partially replace the wound, injury or defect. In some embodiments, the amount of scaffolds is the amount necessary to completely replace the wound, injury or defect. In some embodiments, the conditions comprise contacting at least one layer of aligned fibers with the wound, injury or defect in order to allow the aligned fibers to provide specific guidance cues that direct regenerating tissue efficiently along the aligned layer and across the wound, injury or defect.

In various embodiments, the layer that contacts the wound, injury or defect comprises aligned polymer fibers. In some embodiments, the layer that contacts the wound, injury or defect is the first layer of a scaffold membrane. In some aspects, the layer that contacts the wound, injury or defect is the innermost layer of a scaffold conduit.

The wound, injury or defect can be wounds of any type, injuries of any type, surgical incisions, biopsies, etc.

In some embodiments, contacting a wound, injury or defect with a scaffold comprises placing the scaffolds over the defect. In some embodiments, contacting a wound, injury or defect with a scaffold comprises placing the scaffolds completely within the boundaries of the wound, injury or defect. In some embodiments, contacting a wound, injury or defect with a scaffold comprises placing the scaffolds underneath the defect wound, injury or defect.

In various embodiments, the method also comprises securing the scaffolds in place. In some embodiments, securing the scaffolds in place comprises suturing the scaffolds in place. In some embodiments, the scaffolds are placed on top of the wound, injury or defect and sutured into place. In some embodiments, the scaffolds are placed underneath the wound, injury or defect and sutured into place. In some embodiments, the scaffolds are placed within the boundaries of the wound, injury or defect and sutured into place.

In some embodiments, methods of implanting the scaffolds to repair or replace a defect in a meninx are provided. In some embodiments, the scaffolds are implanted into a subject to repair a defect in the dura mater. In some embodiments, the defect in the dura mater is surgically created. In some embodiments, the method comprises exposing the dura mater by performing any number of standard surgical methods including, without limitation, frontotemporoparietal craniotomy. In some embodiments, a portion of the exposed dura mater is excised and removed to surgically create a defect in the dura mater.

In some embodiments, the methods comprise contacting the defect in the dura mater with one or more scaffolds. In some embodiments, the contacting comprises contacting the defect with a layer of aligned polymer fibers. In some embodiments, the contacting comprises using the scaffold to completely cover the dural defect. In some embodiments, the contacting comprises using the scaffold to partially cover the dural defect.

In some embodiments, the methods comprise contacting the dural defect with a scaffold, wherein the scaffold is placed on top of the defect, superficial to the dura mater. In some embodiments, the methods comprise contacting the dural defect with a scaffold, wherein the scaffold is placed underneath the defect, deep to the dura mater. In some embodiments, the methods comprise contacting the dural defect with a scaffold, wherein the scaffold is placed within the boundaries of the defect, on the same plane as the dura mater.

In some embodiments, the methods comprise completely covering the dural defect with a scaffold and suturing the scaffold in place. In some embodiments, the methods comprise partially covering the dural defect with a scaffold and suturing the scaffold in place. In some embodiments, the methods comprise placing the scaffold within the boundaries of the dural defect and suturing the scaffold in place. In some embodiments, the methods comprise placing the scaffold underneath the dural defect and suturing the scaffold in place.

Kits Including the Scaffolds

In various embodiments, the multilayer fibrous polymer scaffolds described herein can be included as part of a kit. These kits can comprise, inter alia, instructions, such as in the form of an instruction manual, that teach methods of the disclosure and/or that describe the use of the scaffolds as components of the kit. In some embodiments, the kits comprise at least one scaffold and instructions for using the scaffold. In some embodiments, the kits comprise at least one scaffold and instructions for implanting the scaffold in the brain of a subject. In some embodiments, the kit comprise at least one scaffold and instructions for implanting the scaffold in the spinal cord of a subject. In some embodiments, the kits comprise at least one scaffold and instructions for using the scaffold to repair or replace a damaged nerve. In some embodiments, the kits comprise at least one scaffold membrane and instructions for using the scaffold membrane. In some embodiments, the kits comprise at least one scaffold conduit and instructions for using the scaffold conduit.

In some embodiments, the kits indicate that the aligned fibers of a layer of the scaffolds can function by promoting directed outgrowth of tissue located at the periphery of a damaged or defective area and in contact with the aligned layer of the scaffolds, and by continuously guiding regenerating tissue across the damaged or defective area in the direction of the aligned fibers of the first layer until the damage or defect is healed.

In some embodiments, the kits comprise at least one scaffold and instructions for using the scaffold to repair wounds, injuries or defects by promoting the regeneration of anatomical biological components. The anatomical biological components can include, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach and tendons.

The kits can include instructions for using the scaffolds in situations where one or more biological components or tissues are damaged or otherwise contain a defect and are no longer in continuity. In some embodiments, the kits indicate that the scaffolds can be used where the damage or defect is large enough to either greatly hinder or prevent direct regeneration of a biological component or tissue. In some embodiments, the kit indicates that the scaffolds can at least partially bridge the damage or defect and enhance and direct the regeneration of the biological component or tissue across the damage or defect.

In some embodiments, the kits indicate that a damaged or defective area of a biological component or tissue can be contacted with the scaffolds such that a layer of the scaffolds containing aligned polymer fibers contacts the damaged or defective site and the remaining layers of the scaffolds do not contact the damaged or defective area. In some embodiments, the kits indicate that the aligned fibers of the layer that contacts the damaged or defective area can be aligned essentially parallel to the natural alignment of the biological component or tissue to allow the aligned fibers to provide specific guidance cues that direct the regenerating component or tissue efficiently along the aligned layer and across the damaged or defective area.

In some embodiments, the kit comprises at least one scaffold membrane and indications that the scaffold membrane is sided, in that the scaffold has one side comprising aligned fibers and another side comprising randomly oriented fibers. In some embodiments, the instructions include directions for placing an aligned layer of fibers present in the scaffold membrane in contact with a tissue. In some embodiments, the instructions include directions for placing an aligned layer of fibers present in a scaffold membrane in contact with a tissue and parallel to the natural alignment of the tissue. In some embodiments, the tissue is a nerve or nerve fibers. In some embodiments, the tissue is meningeal tissue.

In some embodiments, the kit comprises at least one scaffold conduit and indications that the luminal side of the scaffold conduit comprises aligned fibers and the outer side comprises randomly oriented fibers. In some embodiments, the instructions include directions for placing the luminal layer of aligned fibers present in the scaffold conduit in contact with a tissue. In some embodiments, the instructions include directions for placing the luminal layer of aligned fibers present in a scaffold conduit in contact with a tissue and parallel to the natural alignment of the tissue. In some embodiments, the tissue is a nerve or nerve fibers. In some embodiments, the tissue is a blood vessel.

In various embodiments, the kits indicate that the scaffolds can be shaped and sized by the user to match the specific requirements of the subject's wound, injury or defect. In some embodiments, the kit includes scaffold membranes that are largely square or rectangular in shape and indicates that the scaffolds may be sized to completely cover, or to partially cover, the subject's wound, injury or defect. In some embodiments, the kit includes scaffold conduits and indicates that the scaffolds may be sized to an appropriate length to completely bridge, or to partially bridge, the subject's wound, injury or defect. In various embodiments, the kit indicates that the scaffolds can be used to bridge large wounds, injuries or defects.

In some embodiments, the kit indicates that the wounds, injuries or defects to be bridged can have a length selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm, greater than 35 cm, greater than 40 cm, greater than 45 cm, or greater than 50 cm. In some embodiments, the kit indicates that the wounds, injuries or defects to be bridged can have a length selected from less than 50 cm, less than 45 cm, less than 40 cm, less than 35 cm, less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the kit indicates that the wounds, injuries or defects to be bridged can have a width selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm, greater than 35 cm, greater than 40 cm, greater than 45 cm, or greater than 50 cm. In some embodiments, the kit indicates that the wounds, injuries or defects to be bridged can have a width selected from less than 50 cm, less than 45 cm, less than 40 cm, less than 35 cm, less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In various embodiments, the kits indicate that the scaffolds described herein can be used as an onlay either on top of, or underneath, a wound, injury or defect. In some embodiments, the kits indicate that the scaffolds can be placed within the boundaries of a wound, injury or defect. In some embodiments, the kits indicate that the scaffolds can be placed within the boundaries of discontinuous tissue to bridge a wound, injury or defect gap. In some embodiments, the kits indicate that the scaffolds can be sutured in place.

In some embodiments, the scaffolds in the kits are marked so as to allow a user to differentiate between a side comprising aligned polymer fibers and a side comprising unaligned polymer fibers.

In some embodiments, the scaffolds described herein are included as a component of a kit to be used to replace or repair a severed or damaged meninx, or one or more severed or damaged meninges. In some embodiments, the kit is for use in the regeneration of damaged dura mater in the brain of a subject. The kits can comprise, inter alia, an instruction manual that teaches the use of the scaffolds of the disclosure in the regeneration of the dura mater of the brain.

In some embodiments, the kit is for use in the regeneration of damaged dura mater in the spine or spinal cord of a subject. The kits can comprise, inter alia, an instruction manual that teaches the use of the scaffolds of the disclosure in the regeneration of the dura mater of the spine or spinal cord.

In some embodiments, the scaffolds described herein are included as a component of a kit to be used to replace or repair severed or damaged fascia. In some embodiments, the kit is for use in the regeneration of damaged fascia in a subject. These kits can comprise, inter alia, an instruction manual that teaches the use of the scaffolds of the disclosure in the regeneration of the fascia.

In some embodiments, the scaffolds described herein are included as a component of a kit to be used to replace or repair severed or damaged skin. In some embodiments, the kit is for use in the regeneration of damaged skin in a subject. These kits can comprise, inter alia, an instruction manual that teaches the use of the scaffolds of the disclosure in the regeneration of the skin.

In some embodiments, the scaffolds described herein are included as a component of a kit to be used to replace or repair severed or damaged cardiac tissue. In some embodiments, the kit is for use in the regeneration of damaged cardiac tissue in a subject. These kits can comprise, inter alia, an instruction manual that teaches the use of the scaffolds of the disclosure in the regeneration of the cardiac tissue.

In some embodiments, the scaffolds described herein are included as a component of a kit to be used to replace or repair severed or damaged nerves. In some embodiments, the kit is for use in the regeneration of damaged nerves in a subject. These kits can comprise, inter alia, an instruction manual that teaches the use of the scaffolds of the disclosure in the regeneration of nerves.

In some embodiments, the scaffolds described herein are included as a component of a kit to be used to replace or repair severed or damaged blood vessel. In some embodiments, the kit is for use in the regeneration of damaged blood vessels in a subject. These kits can comprise, inter alia, an instruction manual that teaches the use of the scaffolds of the disclosure in the regeneration of blood vessels.

Creation of the Scaffolds—Rotational Assemblies

The present disclosure provides technology that adapts the electrospinning process to directly fabricate multilayer scaffolds composed of polymer fibers with differential layers of alignment. In various embodiments, the fibers can be formed using the electrospinning apparatus and motor assemblies as described in International Patent Publication No. WO 2007/090102, incorporated herein by reference in its entirety. In various embodiments, the fibers can be formed using the electrospinning apparatus and assemblies described in U.S. Provisional Patent Application No. 61/103,526, the entire contents of which are incorporated herein by this reference.

The fibers of the scaffolds are constructed using an electrospinning apparatus. Several embodiments of such apparatuses are provided in International Patent Publication No. WO 2007/146261, incorporated herein by reference in its entirety.

An exemplary electrospinning apparatus is shown in FIG. 1, which depicts an electrospinning apparatus 30 capable of producing the multilayer fibrous polymer scaffolds described herein. The polymer solution 38, which contains polymer dissolved in a solvent, is contained within the syringe assembly 36. The syringe assembly 36 is part of a syringe pump assembly 32 in which a computer 34 controls the rate at which the polymer solution exits the syringe by controlling pressure or flow rate. Optionally, different flow rates can be provided and controlled to selected spinnerets. The flow rate can be changed to suit the desired physical characteristics of the polymer scaffolds, i.e., membrane thickness, layer thickness, fiber diameter, etc. The syringe pump assembly 32 feeds the polymer solution 38 to a spinneret 42, also referred to as a spinneret, that sits on a platform 44. The spinneret 42 has a tip geometry which allows for jet formation and transportation, without interference. A charge of from about 10 kV to about 30 kV is applied to the spinneret 42 by a high voltage power supply 48 through wire 41A.

Two mandrels 57A and 57B are positioned below the spinneret 42. The mandrels 57A and 57B are electrically charged opposite to the spinneret 42 such that an electric field is created between the charged spinneret 42 and the mandrels 57A and 57B. The electric field causes a jet of the polymer solution to be ejected from the spinneret 42 and spray toward region 55 disposed between the mandrels 57A and 57B, forming micro- or nanometer diameter polymer fibers 46. The drill chucks are grounded using ground wires 41B and 41C.

The first mandrel 57A is attached to a first drill chuck 54, and the first drill chuck 54 is attached to a non-conducting bearing 60. The second mandrel 57B is attached to a second drill chuck 54A, which is attached to a non-conducting bearing 60A. This entire mandrel assembly (non-conducting bearing 60, first drill chuck 54, first mandrel 57A, region 55, second mandrel 57B, second drill chuck 54A and non-conducting bearing 60A) is connected to a motor 52. The motor 52 is linked to a speed control 50 which controls the rate at which the motor 52 spins the mandrels 57A and 57B. Optionally, different spin rates can be provided. The spin rate may be changed to suit the desired physical characteristics of the polymer scaffolds, i.e., membrane thickness, layer thickness, fiber diameter, etc.

Two Mandrel Rotational Assemblies and Fibrous Scaffolds

In certain aspects, the electrospinning assemblies disclosed herein include a rotational assembly having two conducting mandrels.

In one such apparatus, the rotational assembly has first and second conducting outer mandrels rotationally associated along a longitudinal axis of the apparatus within an insulating sleeve between the outer mandrels. A charged electrically conducting spinneret configured to release a solution onto the insulating sleeve is positioned normal to the longitudinal axis of the apparatus above the insulating sleeve. During the electrospinning process, the mandrel assembly is rotated along its longitudinal axis. In various aspects described herein, the sleeve can be configured to be disconnected from the two conducting mandrels and slid over the third conducting mandrel.

Tube Connector Two Mandrel Rotational Assembly

An exemplary two-mandrel device 100 is depicted in FIGS. 2A-2D.

The tube connector embodiment of the two mandrel device 100 includes two short, electrically conducting mandrels 102 and 104 aligned end-to-end along a longitudinal axis 106 and separated by a distance 108. A non-conductive material 110 is used to bridge distance 108 between the electrically conducting mandrels 102 and 104. In an exemplary embodiment, the non-conductive material 110 is non-conductive tubing.

In various embodiments, the electrically conducting mandrels 102 and 104 can be constructed of any conductive material. Exemplary conductive materials include metals such as, for example, aluminum, copper, silver, gold, iron, nickel, titanium and alloys including, without limitation, steels, bronze, brass and conductive polymers such as polyaniline, polypyrrole, polyacetylene, polythiopene.

Figure 2:
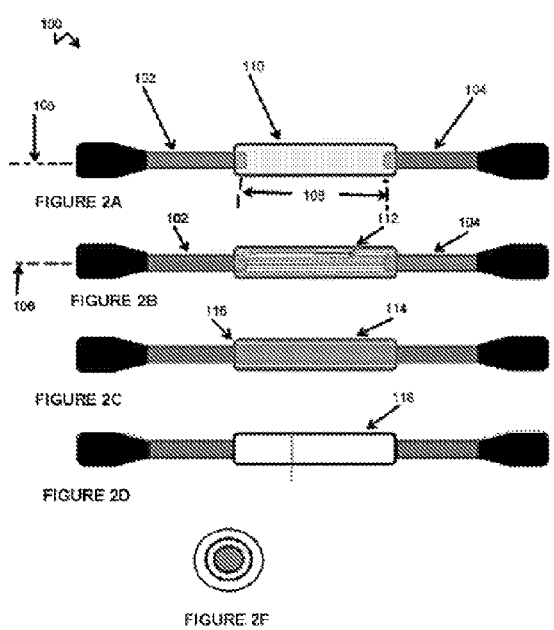
FIG. 2A is a side view of a two mandrel rotational assembly for collecting a first layer of polymer fibers produced by an electrospinning process.
FIG. 2B depicts a side view of the apparatus of FIG. 2A, after a first layer of longitudinally aligned polymer fibers has been deposited.
FIG. 2C depicts a side view of FIG. 2A after a second mandrel has been inserted into the lumen of a hollow tube onto which longitudinally aligned polymer fibers have been disposed.
FIG. 2D depicts a side view of the apparatus of FIG. 2C after a second layer of unaligned fibers has been deposited upon the surface of the first layer of longitudinally aligned polymer fibers.
FIG. 2F depicts a cross-sectional view of the apparatus of FIG. 2D showing the relative positioning of: (i) a conductive mandrel base, (ii) a non-conductive tube positioned upon the mandrel, (iii) a first layer of longitudinally aligned fibers, and (iv) a second layer of non-longitudinally aligned polymer fibers.

The non-conductive material 110 can be hollow, such as a tube that is hollow along the longitudinal axis between the electrically conducting mandrels 102 and 104, or solid i.e. made of material that is not hollow between the electrically conducting mandrels 102 and 104. In embodiments where the non-conductive material 110 is a hollow tube, the tube can have an inner diameter identical to the outer diameters of the electrically conducting mandrels 102 and 104. in this embodiment, the non-conductive material tube 110 bridges the distance 108 between the electrically conducting mandrels 102 and 104 by inserting one end of each mandrel a specific distance inside the lumen of the tube (FIG. 2A). In general, the insertion distance of each electrically conducting mandrel 102 and 104 within the non-conductive material tube 110 is designed to be sufficient to ensure that the two mandrel device 100 is straight and that the stability and strength of the device 100 is maintained. In an alternative embodiment, the non-conductive material 110 has the same outer diameter as the electrically conducting mandrels 102 and 104, whether the material is hollow tube or solid.

In use, the two mandrel device 100 can be used to generate a first layer of polymer fibers that are aligned parallel to the longitudinal axis 106 and that are parallel to the longitudinal axis of the scaffold conduit (e.g. for the luminal wall of a tubular scaffold) by rotating the mandrel assembly 100 about its longitudinal axis 106. Both conducting mandrels 102 and 104 are attached to a power supply (not shown) and charged oppositely to the polymer solution (not shown).

A two mandrel device 100 having a first layer of aligned polymer fibers 112 disposed along the non-conductive material 110 is depicted in FIG. 2B. Once a droplet of polymer solution forms at the tip of the spinneret, the polymer solution is charged with a positive potential. Alternatively, the spinneret is given a negative charge and the mandrels are given a positive charge. The potential can be incrementally increased until a polymer solution has formed and a Taylor cone has stabilized. Electrospinning deposition of the polymer onto the non-conductive material 110, also known as the insulating region, can be allowed to proceed for an appropriate amount of time until a first aligned layer of polymer fibers 112 of a desired thickness is formed.

During electrospinning, the polymer fibers are deposited parallel to the longitudinal axis 106 of the device 100. The aligned fibrous layer 112 is deposited on the non-conductive material 110 which, in the depicted embodiment, is a tube. After electrospinning, the non-conductive tube material 110 and the fibrous layer 112 can be separated from the electrically conductive mandrels 102 and 104. Upon removal, the electrospun fibers formed a tubular polymer scaffold composed of longitudinally aligned fibers.

Tube Sleeve Configured to Form a Second Layer of Fibers

A two mandrel device 100 having a first layer of aligned polymer fibers 112 disposed along the non-conductive material 110 is depicted in FIG. 2B. This device 100 can also be used to create a second layer of differentially aligned fibers disposed on top of the first layer of aligned fibers 112. The second layer of differentially aligned fibers can be arranged in a direction or multiple directions that are different from the alignment direction of the first layer of fibers 112.

The first layer of fibers 112 is electrospun onto the non-conductive material 110 as discussed above.

In various embodiments, a second layer of differentially aligned polymer fibers 118 (as compared to the first layer) can be deposited on the first layer of fibers 112. With reference to FIGS. 2C and 2D, the second layer of fibers 118 provides strength and support in different directions to the generated scaffold which, in the depicted embodiment, is a hollow conduit structure. For example, the second layer of fibers 118 can be randomly aligned, or can be circumferentially aligned. The different alignments can provide additional strength in multiple directions.

In an exemplary embodiment, following the deposition of the first layer of aligned fibers 112 on the non-conducting tube material 110, the non-conducting tube material 110, with the longitudinally aligned polymer fibers 112 deposited thereon, is removed from the electrically conducting mandrels 102 and 104. A tube sleeve having a long electrically conducting mandrel 116 (FIG. 2C) can be inserted through the lumen of the non-conducting tube material 110 upon which the first layer of aligned fibers 112 has been deposited, such that the non-conducting tube material 110 forms a sleeve on the long electrically conducting mandrel 116. In various embodiments, the long electrically conducting mandrel 116 is made of stainless steel (i.e., stainless steel 316) and the non-conducting tube material 110 (as described in the "Tube Connector Embodiment" discussed above) is made of polymers including nylon, polyurethane, polyvinylidene fluoride (PVDF), polyaryletheretherketone (PEEK), polytetrafluoroethylene (PTFE) or Teflon™ (various fluoropolymers), or poly(vinyl chloride) (PVC). In some embodiments, the non-conducting tube material 110 has an inner diameter that is identical to the outer diameter of the long electrically conducting mandrel 116.

In various embodiments, the long electrically conducting mandrel 116 can have an inner diameter that is equal to, or that is smaller than, the inner diameter of the non-conductive tube material 110. In various embodiments, the long electrically conducting mandrel 116 can have a length that is as long as, or that is longer than, the non-conductive tube material 110. Once the long electrically conducting mandrel 116 is inserted through the lumen of the non-conducting tube material 110 such that the tube material 110 forms a sleeve over the mandrel 116, the device 100, and thus the tube material 110 and the mandrel 116, is rotated along its longitudinal axis 106. The first layer of aligned fibers 112 serves as collector substrate for the second layer of deposited fibers 118 via the electrospinning process.

With reference to FIG. 2D, the second layer of deposited fibers 118 may be of the same or different composition as the first layer of longitudinally aligned fibers 112. The second layer of unaligned or circumferentially aligned fibers 118 can be formed without stopping the electrospinning process.

The alignment of the second layer of deposited fibers 118 is dependent upon several factors. A conducting material (e.g. the long electrically conducting mandrel 116) extending along the lumen of the non-conductive tube material 110 results in a second layer of deposited fibers 118 that are not aligned. Rather, once a conducting material is inserted through the lumen of the tube material 110, the subsequent deposition of fibers can be either random or circumferential, depending on the rotation rate of the mandrel assembly 100. At a rotation speed below a transitional rotation speed, the fibers composing the second layer of deposited fibers 118 are randomly aligned. Above the transitional rotation speed, the fibers composing the second layer of deposited fibers 118 are circumferentially aligned.

In various embodiments, the transitional rotation speed depends on the size of collector and surface rotation speed. For example, a large drum has faster surface rotation speed than a smaller mandrel at the same number of rotations per minute. In various embodiments, the circumferential alignment depends on whether the fiber deposition speed is slower or faster than the surface rotation speed of the collector.

In certain embodiments, the electrically conducting mandrels 102 and 104 are hollow (i.e., metal tubes). A metal rod may then be inserted entirely through the hollow conducting regions of mandrels 102 and 104 and through the lumen of the non-conductive tube material 110. In an alternative embodiment, the outer and inner diameters of the first and second mandrels 102 and 104 and the inner diameter of the non-conductive tube material 110 are the same, and each are aligned end to end along the longitudinal axis 106. The non-conductive tube material 110 can be fused to the hollow mandrels 102 and 104 at each end. A conductive material with an outer diameter the same as the inner diameters of each of hollow mandrels 102 and 104, and the non-conductive tube 110, can be passed through the components. In some embodiments, one or both of the mandrels 102 and 104 can be spring loaded such that, after deposition of the first layer of aligned polymer fibers 112, one or both of the mandrels 102 and 104 can be released into the lumen of the non-conductive tube material 100. This way, one or both of the conductive mandrels 102 and 104 can be released to bridge across the non-conductive tube material 110, to cause the subsequent deposition of fibers to be unaligned (e.g. to have a random orientation) or circumferential. The resulting fibrous tubular scaffold has at least two layers of a fibers with different alignments. The inner layer 112 has longitudinally aligned fibers that traverse the longitudinal axis of the scaffold. The second layer 118 has either unaligned layers, or circumferentially aligned layers. The fibers in each layer are a single, continuous polymer fiber.

The stacking density of fibers can be controlled by varying inputs in the two mandrel rotational apparatus 100. For example, increasing the length of the non-conductive material 110, also known as the insulating region increases distance across which the polymer fibers are deposited, which results in less dense fibrous layers. Increasing the collection time results in the formation of more dense fibrous layers because the polymer solution jetting from the spinneret spends more time on any given surface of the collector substrate (the non-conducting material 110). When the collection time is shorter, the fibers are also less dense because residual charges in the fibers create repulsive forces between them and there is space for the fibers to separate and become less dense. See also Li, et al. "Electrospinning of Polymeric and Ceramic Fibers as Uniaxially Aligned Arrays" *Nano Lett.*, Vol. 3, No. 8, 2003, which is incorporated herein by reference in its entirety.

Three Component Rotational Assemblies and Fibrous Scaffolds

In various embodiments, a three component mandrel or drum assembly device can provide critical density and differential alignment of fibers.

An exemplary three mandrel assembly 200 is depicted in FIGS. 3A-3C. The three mandrel assembly 200 includes first and second outer mandrels 202 and 206, and inner mandrel 204, aligned end-to-end longitudinally along the longitudinal axis 208 of the assembly 200. Outer mandrel 202 and inner mandrel 204 are separated by an insulating region 210. Likewise, inner mandrel 204 and outer mandrel 206 are separated by an insulating region 212. The outer mandrels 202 and 206 are attached to a rotation assembly and a power supply (not shown). The inner mandrel 204 is not attached to a rotational assembly, and is at a floating potential.

The three mandrel assembly 200 can be used to create both a first layer of aligned fibers and one or more subsequent layers of differentially (i.e., unaligned) fibers without changing any electrospinning conditions. After electrospinning a first layer of aligned fibers, a time delay can be used in which a critical density of the aligned fibers covers the insulating regions 210 and 212 that connect the conducting mandrels 202 and 206.

In various embodiments, the two outer electrically conducting mandrels 202 and 206 can be constructed of any conductive material, such as stainless steel. The two outer mandrels 202 and 206 can be grounded or charged. The inner mandrel 204 is not grounded, but instead is a floating potential. An electrically insulating material is used to fill the insulating regions 210 and 212, and such material may either be a tube or a solid material. For example, in embodiments where the electrically insulating material is a tube, the tube may be constructed of nylon, polyurethane, polyvinylidene fluoride (PVDF), polyaryletheretherketone (PEEK), polytetrafluoroethylene (PTFE) or Teflon™ (various fluoropolymers), or poly(vinyl chloride) (PVC). If polymer material is used for the insulating regions, it can have an inner diameter identical to the outer diameter of the mandrels.

The lengths of the mandrels 202, 204, 206 may vary. In certain embodiments, the outer mandrels 202 and 206, whether grounded or charged, can be longer than the inner mandrel 204 that remains ungrounded.

Non-conductive polymer material can be used to bridge the insulating regions 210 and 212, between outer mandrel 202 and inner mandrel 204, and between outer mandrel 206 and inner mandrel 204, respectively. In various embodiments, each end of a non-conductive tube material can be used to bridge insulating regions 210 and 212 by inserting and end of the tube material over each end of each mandrel 202, 204, 206. The distance that the mandrels 202, 204, 206 are inserted into the tube material can be sufficient to maintain the structure, strength, and stability of the device 200.

The mandrel assembly 200 is rotated around its longitudinal axis 208 and the outer mandrels 202 and 206 are electrically charged oppositely to the polymer solution (not shown). For example, the polymer solution may be positively charged, and the outer mandrels 202 and 206 negatively charged. Alternatively, the outer mandrels 202 and 206 may be grounded.

With reference to FIG. 3B, longitudinally aligned fibers deposit across the lengths of each non-conductive region 210 and 212 and across the inner mandrel 204. Aligned fibers form an arc from the outer edges of each of the two non-conductive regions 210 and 212. The fibers initially contact the edge of the overlap region at the border between outer mandrel 202 and non-conductive region 210, and at the border between outer mandrel 206 and non-conductive region 212. The arcing fibers have the opposite charge to outer mandrels 202 and 206. The arcing fibers lose their charge shortly after deposition and settle onto the center mandrel in a longitudinally aligned manner. There is thus a constant deposition of arcing fibers and a constant settling of fibers onto non-conductive regions 210 and 212 and onto the inner mandrel 204 during electrospinning. The region of deposition on the non-conductive regions 210 and 212 and on the inner mandrel 204 moves closer and closer to the inner mandrel 204 as the process continues. Eventually, the fibers no longer arc between the two non-conducting regions 210 and 212. The longitudinally aligned fibers thus form over each insulating regions 210 and 212 and the inner mandrel 204.

With reference to FIG. 3C, upon the longitudinally aligned fibers reaching a critical density through the electrospinning process, the subsequent deposition of fibers through the same rotation rate and potential applied to the inner mandrel 204 and spinnerets results in the formation of a second layer of fibers having a different orientation from the first longitudinally aligned fibers deposited on the inner mandrel 204.

In certain embodiments, the second layer of fibers is randomly aligned, with no prevalent alignment axis (i.e., no net alignment or direction). When the rotation speed of the mandrel assembly 200 is below the critical speed, depositing fibers will be randomly oriented. Alternatively if, after the aligned layer has deposited, the speed of rotation of the mandrel assembly 200 is increased above a transitional rotation speed, as described herein, the depositing fibers will be circumferentially aligned. By varying the mandrel rotation speed, alignment can be differentiated between random and circumferential.

The resulting fibrous polymer scaffolds have similar characteristics to those produced using the two mandrel embodiment described above. However, both layers can be produced from a single, unbroken polymer fiber. Because of the attachment via the unbroken polymer fiber, the different layers cannot be delaminated (i.e. separated completely), or shift along their axis without breaking the single fiber. Accordingly, a two layer scaffold can be constructed that does not readily allow delamination of the layers.

In one embodiment the continuous layers of fibers may be formed of the same polymer solution. In another embodiment, the continuous layers of fibers may be formed of two or more different polymer solutions. A series of different polymer solutions can be sequentially fed through the same tube into the same electrospinner jet to create a continuous flow even while changing the composition of the solution used to spin fibers.

Figure 4:
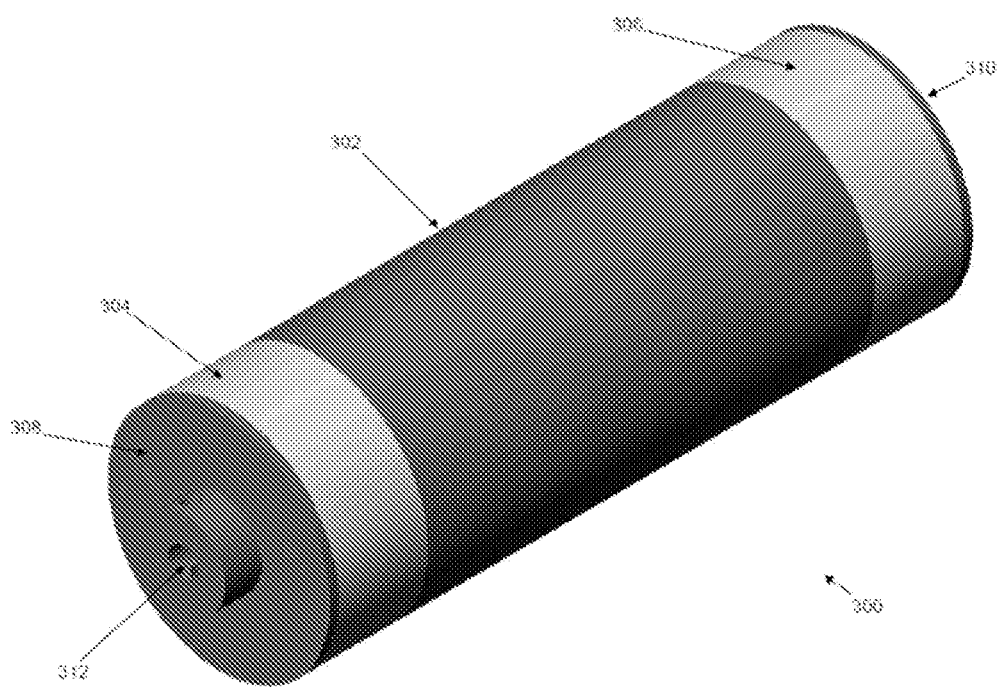
FIG. 4 depicts a multi-section drum collector.

An exemplary drum assembly 300 is depicted in FIG. 4. The drum assembly 300 includes a central conductive drum 302 and electrically insulating drums 304, 306 flanking the central drum at each end. The drum assembly is capped by thin conductive discs 308, 310 at each end. A conductive mandrel (not shown) is inserted through the drum 300 at opening 312 and makes contact with the conductive end caps 308 and 310. The mandrel is attached to a rotation assembly (not shown) and is charged by a high voltage power supply. The end caps 308 and 310 of the drum assembly are also charged via their contact points with the mandrel. The central conductive drum 302 is not charged or grounded.

The drum embodiment 300 can be used to create both a first layer of fibers that are aligned along a first axis, parallel to the longitudinal axis of the drum collector, and one or more subsequent layers of differentially (i.e., unaligned or aligned along a second axis of the membrane) fibers, without changing any electrospinning conditions.

In various embodiments, the central drum 302, end capping discs 308 and 310 and mandrel (not shown) can be constructed of any electrically conductive material, such as stainless steel. The mandrel and the end capping discs 308 and 310 can be grounded or charged. The central conductive drum 302 is not grounded, but instead is a floating potential. The electrically insulating regions 304 and 306 may be constructed of appropriate material such as nylon, polyurethane, polyvinylidene fluoride (PVDF), polyaryletheretherketone (PEEK), polytetrafluoroethylene (PTFE) or Teflon™ (various fluoropolymers), or poly(vinyl chloride) (PVC).

The length and diameter of the drum assembly 300 may vary.

The drum assembly 300 is rotated around its longitudinal axis and the mandrel and end caps 308 and 310 are electrically charged oppositely to the polymer solution. For example, the polymer solution may be positively charged, and the mandrel and end caps 308 and 310 are negatively charged. Alternatively, the mandrel and end caps 308 and 310 may be grounded.

With reference to FIG. 4, polymer fibers that are aligned along a first axis of the scaffold, and parallel to the longitudinally axis of the drum collector, deposit across the lengths of each non-conductive region 304 and 306 and across the central conductive drum 302. Aligned fibers form an arc from the edges of each of the two non-conductive regions 304 and 306. The fibers initially contact the edge of the end capping discs 308 and 310 and arc over the drum assembly 300. The arcing fibers have the opposite charge to the end capping discs 308 and 310. The arcing fibers lose their charge shortly after deposition and settle on the center conductive drum 302 in a manner that is aligned along a first axis of the scaffold and parallel to the longitudinal axis of the drum collector. There is thus a constant deposition of arcing fibers and a constant settling of fibers on the central conductive drum 302 during electrospinning. The contact points of the arcing fibers begin at the end capping discs 308 and 310 and proceed across the surfaces of the two electrically insulating regions 304 and 306 until the arc contact points reach the central conductive drum 302. During this process, layers of polymer fibers that are aligned along a first axis of the scaffold, and parallel to the longitudinal axis of the drum collector, form over each of the two insulating regions 304 and 306 and the central conductive drum 302.

During electrospinning, when the arc contact points of the fibers that are aligned along a first axis of the scaffold reach the edges of the central conductive drum 302, the subsequent deposition of fibers, through the same rotation rate and potential applied to the mandrel and spinneret(s), results in the formation of a second layer of fibers having a different orientation from the first layer.

In certain embodiments, the second layer of fibers is randomly aligned, with no prevalent axis of alignment (i.e., no net alignment or direction). When the rotation speed of the drum assembly 300 is below the critical speed, depositing fibers will be randomly oriented. Alternatively, after the aligned layer has deposited, the rotation speed of the drum assembly 300 can be increased above a transitional rotation speed as described herein and the depositing fibers of the nascent second layer will be aligned along a second axis of the scaffold. By varying the rotation speed, alignment of the polymer fibers of the second layer can be differentiated between random and aligned along a second axis of the scaffold.

It will be understood that additional drum regions can be used so long as insulating regions are used to separate adjacent drum regions formed of conductive materials. For example, in certain embodiments, some of the conductive drum regions in a multi mandrel embodiment are neither grounded nor charged.

The resulting fibrous polymer scaffolds have similar characteristics to those produced using the two mandrel embodiment, described above. However, both layers can be produced from a single unbroken polymer fiber, from two unbroken fibers, from three unbroken fibers, and so on. Because of the attachment, the different layers cannot be delaminated (i.e. separated completely), or shift along their axis without breaking the continuous fiber(s). Accordingly, a multiple layer scaffold can be constructed that does not readily allow delamination of the layers.

In an alternative process, in a single electrospinning session the polymer solution never stops flowing between layers, but rather flows from the spinneret continuously between the layers. The spinneret that dispenses the solution moves laterally, parallel to the longitudinal axis of the mandrel. The spinneret can move in any direction depending upon the desired fiber alignment pattern. The spinneret may also encircle the scaffold and spray upward from the bottom of the scaffold. The spinneret and mandrel keep the polymer solution moving to ensure substantially even layers of fibers deposited throughout the shape of the scaffold. However, depending upon the specific application, in some embodiments it may be desirable for parts of the scaffold to be thicker than others and the spinneret movement or mandrel rotation can be adjusted accordingly to accommodate a scaffold (i.e., hollow conduit, filled conduit, membrane/sheet, etc.) of differential thickness.

Figure 5:
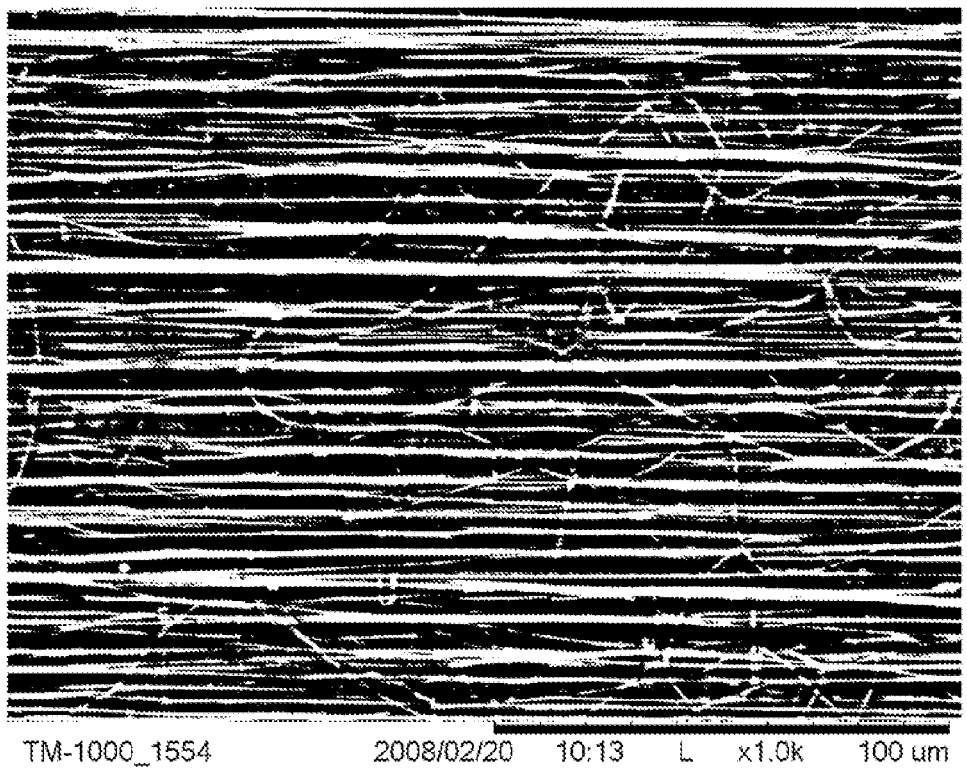
FIG. 5 is an electron micrograph of the first layer of a two-layer fibrous scaffold having aligned fibers in the first layer and unaligned fibers in the second layer.
Figure 6:
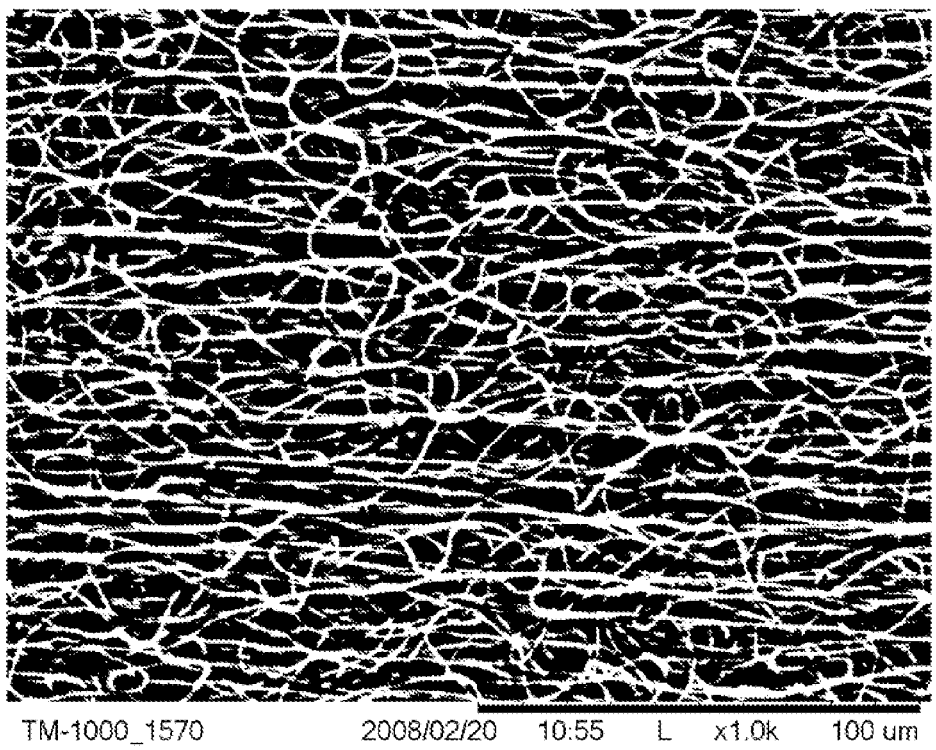
FIG. 6 is an electron micrograph of the second layer of the two-layer fibrous scaffold of FIG. 5.

An exemplary first layer of aligned polymer fibers in a fibrous polymer scaffold, which can be produced using any of the electrospinning apparatuses and techniques described herein, is depicted in FIG. 5. An exemplary second layer of unaligned or randomly oriented polymer fibers in a fibrous polymer scaffold, which can be produced using any of the electrospinning apparatuses and techniques described herein, is depicted in FIG. 6.

Rotational Assemblies with Conductive Arms

In various embodiments, a rotational assembly device includes one or more conductive arms.

The conductive arms are electrically conductive components that can be attached to any of the electrospinning apparatuses disclosed herein. When electrically charged, the conductive arms can be used to repel an electrospinning polymer fiber. Therefore, the direction of polymer fiber deposition can be controlled via the use of one or more conductive arms.

Under typical electrospinning conditions, a positively charged polymer fiber is ejected from a spinneret away from a positively charged spinneret-holder plate, and toward a negatively charged collector (e.g. a mandrel or drum). This is typically done at a distance away from the collector such that there is an air gap between the tip of the spinneret and the collector, through which the polymer fiber must travel (see, e.g., FIG. 1). In the air gap between the spinneret and the collector, the nascent polymer fiber is free to move as it proceeds through the air gap to the collector. It is typical for the polymer fiber to move erratically, in several directions, as it is guided generally by the electric field from the spinneret to the collector.

By introducing additional, positively charged elements such as the conductive arms into the vicinity of the electrospinning fiber, the direction of deposition of the polymer fiber can be controlled. The positively charged polymer fiber is repelled from the positive charge of the conducting arms and will thus tend to move in a direction away from the positively charged conducting arms toward a negatively charged element.

Figure 7:
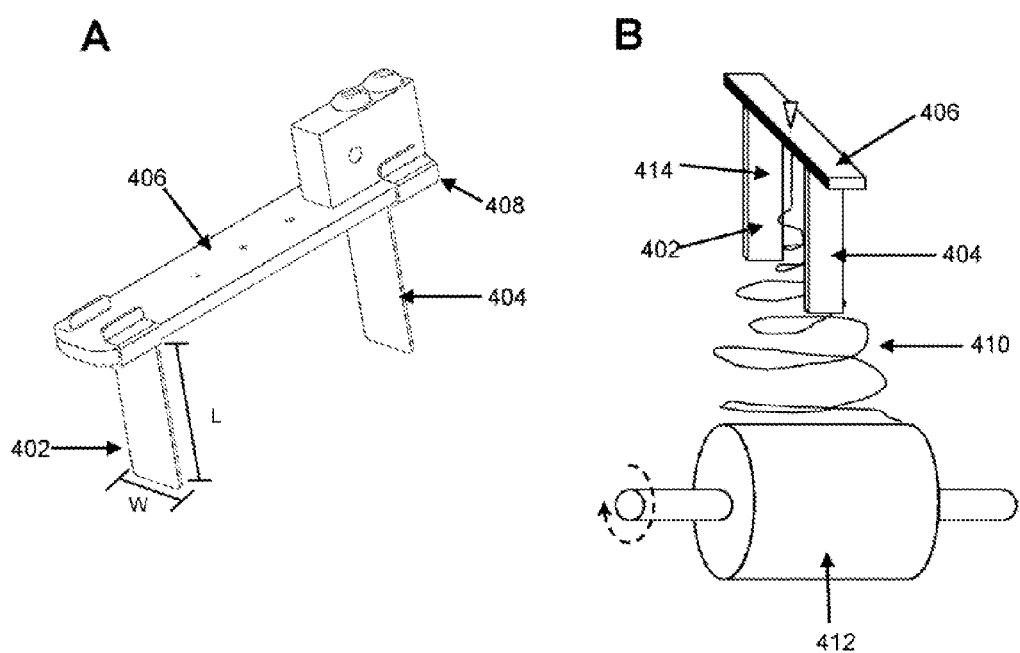
FIG. 7A depicts an electrospinning apparatus with a pair of conducting arms.
FIG. 7B depicts an exemplary method of using a pair of conducting arms to direct the deposition of polymer fibers onto a collector.

An exemplary apparatus 400 with a pair of positively charged conducting arms 402 and 404 is shown in FIG. 7A. In the depicted embodiment, the conductive arms 402 and 404 are attached to a spinneret platform 406, also known as a spinneret holder plate. Each of the conductive arms 402 and 404 have a length L and a width W. In various embodiments, the conductive arms 402 and 404 may be attached to the spinneret-holder plate 406 itself, or may be free-standing elements, existing apart from the spinneret-holder plate 406. In the embodiment depicted in FIG. 7A, each of the conductive arms 402 and 404 are attached directly to the spinneret-holder plate 46 by way of a clip 408. In the depicted embodiment, the clip 408 is an extension of each of the conductive arms 402 and 404, and is thus an integral part of each of the conductive arms 402 and 404. Clip 408 is designed to slide over an end of the spinneret-holder plate 406, securing the conductive arm in place at the plate 406.

As shown in FIG. 7B, the conductive arms 402 and 404 extend downward from the spinneret-holder plate 406, toward the desired collector, which in the depicted embodiment is a drum 412. The conductive arms 402 and 404 thus extend into the air gap between the spinneret-holder plate 406 and the drum 412. During electrospinning, a positive charge is applied to the spinneret-holder plate 406. Because the conductive arms 402 and 404 are in direct contact with the spinneret-holder plate 406, the positive charge is also imparted to the conductive arms 402 and 404. A positively charged polymer fiber 410 is ejected from a spinneret tip 414 as described previously. The polymer fiber proceeds through the air gap between the conductive arms 402 and 404, toward the drum 412, which is negatively charged. Because the conductive arms 402 and 404 are positively charged, the positively charged polymer fiber 410 will be repelled by the charge of the conductive arms 402 and 404 as it travels from the spinneret tip 414 to the drum 412.

The means of attaching the conductive arms 402 and 404 to the spinneret holder plate 406 can be varied. In the embodiment depicted in FIG. 7A, the conductive arms 402 and 404 are attached to the plate 408 via a clip 408. In some embodiments, the conductive arms 402 and 404 can be attached to the plate 406 by any other mechanical means including, for example, by welding them to the plate 406, by screwing them into place at the plate 406, or by other means of attachment. In an alternate embodiment, the conductive plates 402 and 406 are not attached to the plate 406 itself, but are rather present in the air gap by some other means including, for example, by a stand that holds each of the conductive plates 402 and 406 in place at the air gap (not shown).

Any number of conductive arms can be employed. In some embodiments, a single conductive arm 402 is attached to a spinneret-holder plate 406 in an electrospinning apparatus. In some embodiments, two conductive arms 402 and 404 are attached to a spinneret-holder plate 406 in an electrospinning apparatus. In some embodiments, three conductive arms are attached to a spinneret-holder plate 406 in an electrospinning apparatus. In some embodiments, four conductive arms are attached to a spinneret-holder plate 406 in an electrospinning apparatus. In some embodiments, five or more conductive arms are attached to a spinneret-holder plate 406 in an electrospinning apparatus. In some embodiments, a single conductive arm 402 is introduced into the air gap in the vicinity of a spinneret-holder plate 406 in an electrospinning apparatus, but is not connected to the plate 406. In some embodiments, two conductive arms 402 and 404 are introduced into the air gap in the vicinity of a spinneret-holder plate 406 in an electrospinning apparatus, but are not connected to the plate 406. In some embodiments, three conductive arms are introduced into the air gap in the vicinity of a spinneret-holder plate 406 in an electrospinning apparatus, but are not connected to the plate 406. In some embodiments, four conductive arms are introduced into the air gap in the vicinity of a spinneret-holder plate 406 in an electrospinning apparatus, but are not connected to the plate 406. In some embodiments, five or more conductive arms are introduced into the air gap in the vicinity of a spinneret-holder plate 406 in an electrospinning apparatus, but are not connected to the plate 406.

The position and/or orientation of the conductive arms can be altered to prevent the polymer fiber from moving in one or more specific directions and to encourage the polymer fiber to move in one or more other directions. In some embodiments, the conductive arms are oriented such that they direct the polymer fiber to move and/or deposit along the longitudinal axis of a collector. In some embodiments, the conductive arms are oriented such that they direct the polymer fiber to move and/or deposit along the circumferential axis of a collector. In some embodiments, the conductive arms are oriented such that they direct the polymer fiber to move and/or deposit at an angle relative to any axis of a collector.

The shape and size of the conductive arms can be altered. In some embodiments, the conductive arms are rectangular in shape. In some embodiments, the conductive arms are oval in shape. In some embodiments, the conductive arms are square in shape. In some embodiments, more than one conductive arm is used and each arm is independently a shape selected from rectangular, square and oval.

In some embodiments, the conductive arms have a length (L) of greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, or greater than 20 cm. In some embodiments, the conductive arms have a length (L) of less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the conductive arms have a width (W) of greater than 0.1 cm, greater than 0.2 cm, greater than 0.3 cm, greater than 0.4 cm, greater than 0.5 cm, greater than 0.6 cm, greater than 0.7 cm, greater than 0.8 cm, greater than 0.9 cm, greater than 1 cm, greater than 2 cm, greater than 3 cm, greater than 4 cm, greater than 5 cm, greater than 6 cm, greater than 7 cm, greater than 8 cm, greater than 9 cm, or greater than 10 cm. In some embodiments, the conductive arms have a width (W) of less than 10 cm, less than 9 cm, less than 8 cm, less than 7 cm, less than 6 cm, less than 5 cm, less than 4 cm, less than 3 cm, less than 2 cm, less than 1 cm, less than 0.9 cm, less than 0.8 cm, less than 0.7 cm, less than 0.6 cm, less than 0.5 cm, less than 0.4 cm, less than 0.3 cm, less than 0.2 cm, or less than 0.1 cm.

In some embodiments, the conductive arms have a thickness of greater than 0.1 cm, greater than 0.2 cm, greater than 0.3 cm, greater than 0.4 cm, greater than 0.5 cm, greater than 0.6 cm, greater than 0.7 cm, greater than 0.8 cm, greater than 0.9 cm, greater than 100 cm, greater than 1.1 cm, greater than 1.2 cm, greater than 1.3 cm, greater than 1.4 cm, greater than 1.5 cm, greater than 1.6 cm, greater than 1.7 cm, greater than 1.8 cm, greater than 1.9 cm, or greater than 2.0 cm. In some embodiments, the conductive arms have a thickness of less than 2.0 cm, less than 1.9 cm, less than 1.8 cm, less than 1.7 cm, less than 1.6 cm, less than 1.5 cm, less than 1.4 cm, less than 1.3 cm, less than 1.2 cm, less than 1.1 cm, less than 1.0 cm, less than 0.9 cm, less than 0.8 cm, less than 0.7 cm, less than 0.6 cm, less than 0.5 cm, less than 0.4 cm, less than 0.3 cm, less than 0.2 cm, or less than 0.1 cm.

In various embodiments, the electrically conducting arms can be constructed of any conductive material. Exemplary conductive materials include metals such as, for example, aluminum, copper, silver, gold, iron, nickel, titanium and alloys including, without limitation, steels, bronze, brass and conductive polymers such as polyaniline, polypyrrole, polyacetylene, polythiopene. In some embodiments, the conducting arms are constructed of the same material as the collector used in the electrospinning apparatus.

By deliberately placing the conductive arms within the electrospinning area, the overall electric field within the electrospinning area in any electrospinning apparatus, inclusive of those disclosed herein, can be altered. The conducting arms can thus be used to guide the movement of a polymer fiber during electrospinning. In various embodiments, the conductive arms can be used to improve the overall alignment of the polymer fibers deposited in a scaffold. In some embodiments, two rectangular shaped conductive arms are employed in an electrospinning apparatus such that a flat face of each of the conductive arms is oriented opposite the other, as depicted in FIG. 7A. As shown in the embodiment depicted in FIG. 7B, the direction of polymer fiber movement, and this the direction of polymer fiber deposition along a collector, can be controlled.

Differences in spinneret height can be used to help control the degree of polymer fiber alignment when conductive arms are employed. As noted herein, the distance between the spinneret tip and the top surface of the collector can have an effect on the resulting deposition of the polymer fibers along a collector. In various aspects, conductive arms can be employed with an electrospinning apparatus when the spinneret tip is positioned at any height above the collector. In some embodiments, the conductive arms can be employed when the spinneret tip is positioned at lower heights. In some embodiments, conductive arms can be used to direct polymer fiber alignment and deposition when the spinneret tip is positioned greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 28 cm, greater than 29 cm, or greater than 30 cm above the collector. In some embodiments, conductive arms can be used to direct polymer fiber alignment and deposition when the spinneret tip is positioned less than 30 cm, less than 29 cm, less then 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, or less than 5 cm above the collector. In some embodiments, conductive arms can be used to direct polymer fiber alignment and deposition when the spinneret tip is positioned 12 cm above the collector. During a typical electrospinning process, at lower spinneret heights alignment of polymer fibers is more difficult because the fibers do not have sufficient time to arch in advance of deposition and thus the fibers tend to deposit in a more random orientation. While not wishing to be limited to any particular theory or embodiment, it is believed that, at lower spinneret heights, the conductive arms make up for a lack of arching fibers in terms of overall alignment by controlling the direction of fiber alignment for a greater distance across the air gap between the spinneret tip and the collector. In some embodiments, the conductive arms can be employed to contain the movement of the polymer fiber for a larger fraction of its travel across the air gap from the spinneret tip to the collector.

The conductive arms alter the overall electric field in the electrospinning area to manipulate fiber movement and deposition. However, differences in the electric field in the electrospinning area also cause differences in the minimum required voltage to achieve an electrospinning fiber. The electrospinning process and required voltages can be specifically controlled by varying the size and geometry of the conductive arms, and thus, manipulating the induced electric field. In some embodiments, two conducting arms having a width of from 0.25 cm-2.0 cm are used during electrospinning. In some embodiments, two conductive arms of 1.5 cm width are used during electrospinning. In some embodiments, two conductive arms of 0.5 cm width are used during electrospinning. In some embodiments, the voltage required for electrospinning can be reduced by using conductive arms with a narrow width.

Fiber alignment can be altered within the various layers of a single scaffold by altering the orientation of the conductive arms for each layer accordingly. For example, during a single electrospinning run, the orientation of the conductive arms can be changed. In some embodiments, the orientation of the conductive arms is parallel to the longitudinal axis of the collector during electrospinning. In some embodiments, the orientation of the conductive arms is perpendicular to the longitudinal axis of the collector during electrospinning. In some embodiments, the orientation of the conductive arms is changed during electrospinning. In some embodiments, the orientation of the conductive arms is parallel to the longitudinal axis of the collector during electrospinning of a first layer of a scaffold. In some embodiments, the orientation of the conductive arms is perpendicular to the longitudinal axis of the collector during electrospinning of a second layer of a scaffold. In some embodiments, the orientation of the conductive arms is parallel to the longitudinal axis of the collector during electrospinning of a first layer of a scaffold and the orientation of the conductive arms is perpendicular to the longitudinal axis of the collector during electrospinning of a second layer of the scaffold.

Polymer fiber alignment is dependent on the orientation of the conductive arms during electrospinning. In some embodiments, the conductive arms are oriented parallel to the longitudinal axis of the collector during electrospinning and the polymer fibers in the resulting layer of the scaffold are also aligned parallel to the longitudinal axis of the collector. In some embodiments, the conductive arms are oriented perpendicular to the longitudinal axis of the collector during electrospinning and the polymer fibers in the resulting layer of the scaffold are unaligned or randomly oriented.

Figure 15:
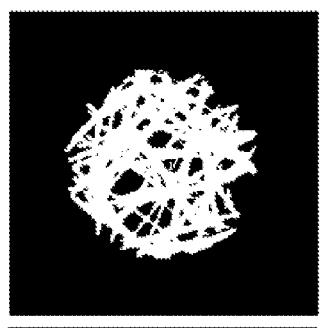
FIG. 15 is a histogram depicting the difference in polymer fiber alignment between polymer fibers electrospun onto a drum collector with and without the use of conductive arms.
Figure 15:
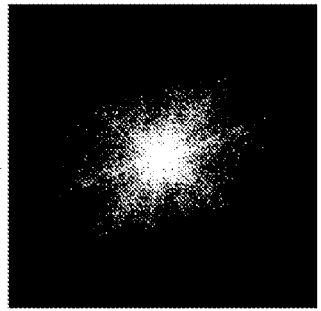
Figure 15:
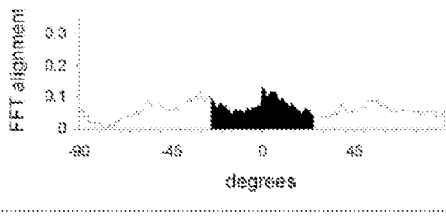
Figure 15:
Figure 15:
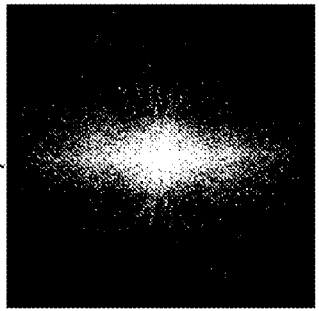
Figure 15:
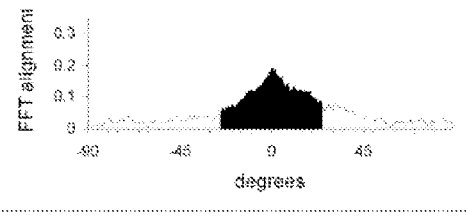

In various aspects, the conductive arms can be used during electrospinning to control and/or improve polymer fiber alignment in a scaffold. In some embodiments, conductive arms can be used in an electrospinning apparatus having a steel drum collector to improve fiber alignment by orienting the conductive arms parallel to the longitudinal axis of the collector. FIG. 15 shows the difference between aligned polymer fibers electrospun onto a drum collector (onto the single, electrically conductive section only) with the use of conductive arms, and without the use of conductive arms. The images of the fibers shown in FIG. 15 were converted using 2D Fourier Fast Transform (2D FFT) and these transformed images were then converted into histograms representing the approximate degree of fiber alignment within each sample. As shown in FIG. 15, when the conductive arms were employed, the histogram shows a single, large, primary peak corresponding to the main axis of fiber alignment within the sample, indicating that the fibers are aligned. When the conductive arms were not employed, many small peaks are observed in the histogram, with no obvious prominent peak, indicating that the fibers in the sample had no primary axis of alignment—that the fibers are unaligned.

Figure 16:
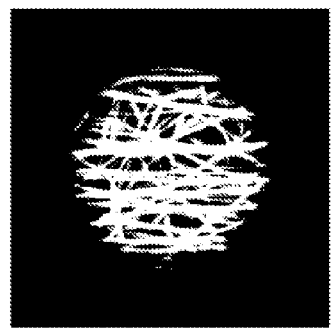
FIG. 16 is a histogram depicting the difference in polymer fiber alignment between polymer fibers electrospun onto a conveyor belt collector with and without the use of conductive arms.
Figure 16:
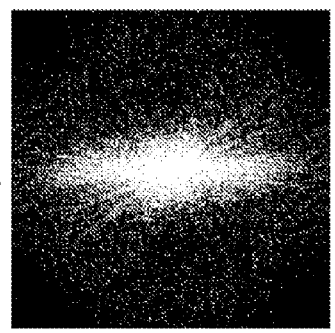
Figure 16:
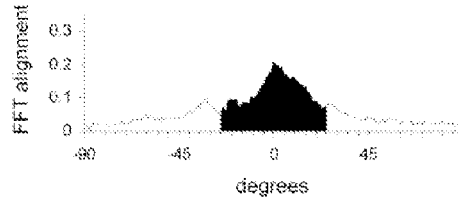
Figure 16:
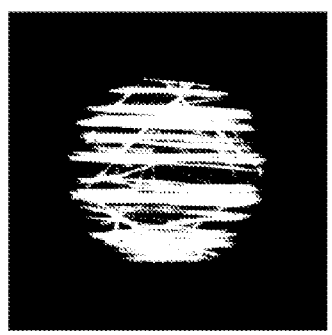
Figure 16:
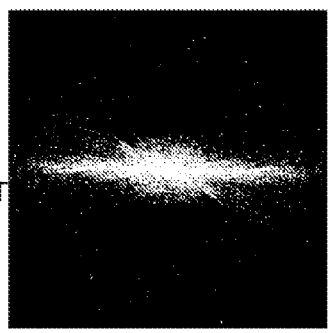
Figure 16:
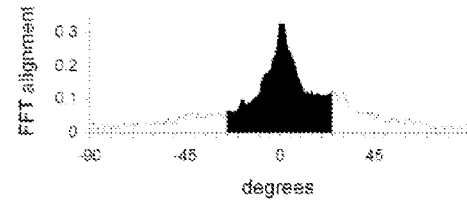

In some embodiments, conductive arms can be used in an electrospinning apparatus having a conveyor belt collector to improve fiber alignment by orienting the conductive arms parallel to the longitudinal axis of the conveyor belt collector. FIG. 16 shows the difference between polymer fibers electrospun onto a conveyor belt collector with the use of conductive arms, and without the use of conductive arms. The images of the fibers shown in FIG. 16 were also converted using 2D Fourier Fast Transform (2D FFT) and the transformed images were converted into histograms representing the approximate degree of fiber alignment within each sample. As shown in FIG. 16, the primary histogram peak corresponding to the main axis of fiber alignment is much taller and skinnier when the conductive arms are employed than when the conductive arms are not employed, indicating that the alignment of the polymer fibers is improved when the fibers are deposited on the conveyor belt collector when the conductive arms are employed.

Figure 17:
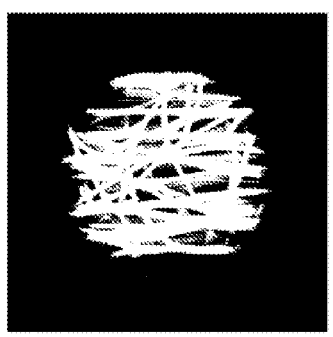
FIG. 17 is a histogram depicting the difference in polymer fiber alignment between polymer fibers electrospun onto a multi-sectioned drum collector with and without the use of conductive arms.
Figure 17:
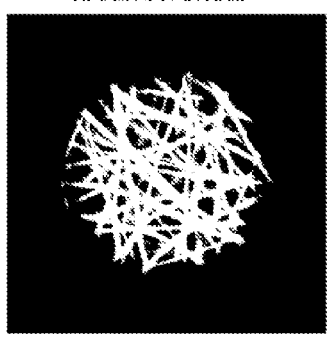
Figure 17:
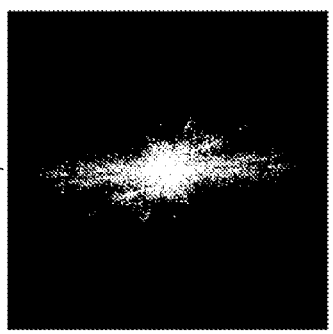
Figure 17:
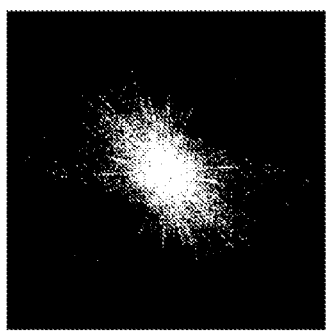
Figure 17:
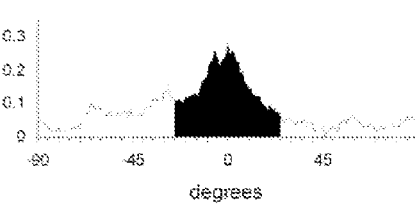
Figure 17:
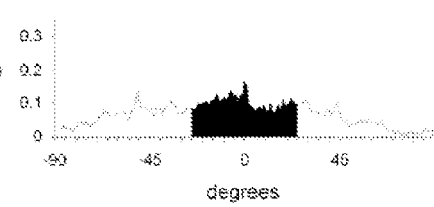

In various aspects, the conductive arms can be used during electrospinning to improve the deposition of unaligned polymer fibers in a scaffold. In some embodiments, conductive arms can be used in an electrospinning apparatus having a multi-sectioned drum collector to improve the deposition of unaligned polymer fibers by orienting the conductive arms perpendicular to the longitudinal axis of the collector. FIG. 17 shows the difference in fiber alignment between polymer fibers electrospun onto a multi-sectioned drum collector when the conductive arms are oriented along a longitudinal axis and a circumferential axis. The images of the fibers shown in FIG. 17 were also converted using 2D Fourier Fast Transform (2D FFT) and the transformed images were converted into histograms representing the approximate degree of fiber alignment within each sample. As shown in FIG. 17, the histogram shows a single prominent peak when the conductive arms are aligned parallel to the longitudinal axis of the collector, indicating that the fibers are well aligned within the sample, but shows no primary peak when the conductive arms are aligned parallel to the circumferential axis of the collector, indicating that the polymer fibers are unaligned.

Conveyer-Belt Assemblies

In various embodiments, a rotational conveyer-belt like assembly device can provide differential alignment of fibers.

During electrospinning, polymer fiber alignment depends, at least in part, on the size and geometry of the collector used. As disclosed herein, in various embodiments small-diameter, multi-mandrel electrospinning collectors can be used to create fibrous polymer scaffolds having aligned fibers in a first deposited layer of polymer fibers. Smaller-diameter mandrel collectors have a small circumference, which may serve to minimize the movement of the nascent polymer fiber during electrospinning and also minimize fiber deposition in the circumferential direction of the collector. Therefore, a smaller diameter collector may serve to enhance polymer movement and deposition in an aligned manner, thereby generating improved alignment.

In various aspects, multi-sectioned conveyor belt collectors are disclosed. In various embodiments, the conveyor belts have a large longitudinal axis/radial axis ratio at their curved edges, but also have large overall surface areas for generating large scaffold membranes. In various embodiments, the conveyor belt collectors have a reduced radius of curvature at both ends and have a large collecting surface area. In various embodiments, the conveyor-belt assembly can be used to create a large fibrous polymer scaffold membrane with aligned fibers. Multi-section conveyor belt collectors can be used to make fibrous polymer scaffold membranes having both large surface area and a high degree of fiber alignment. Additionally, conductive arms can be incorporated into the electrospinning procedure to further enhance fiber alignment in the resulting membranes.

Figure 8:
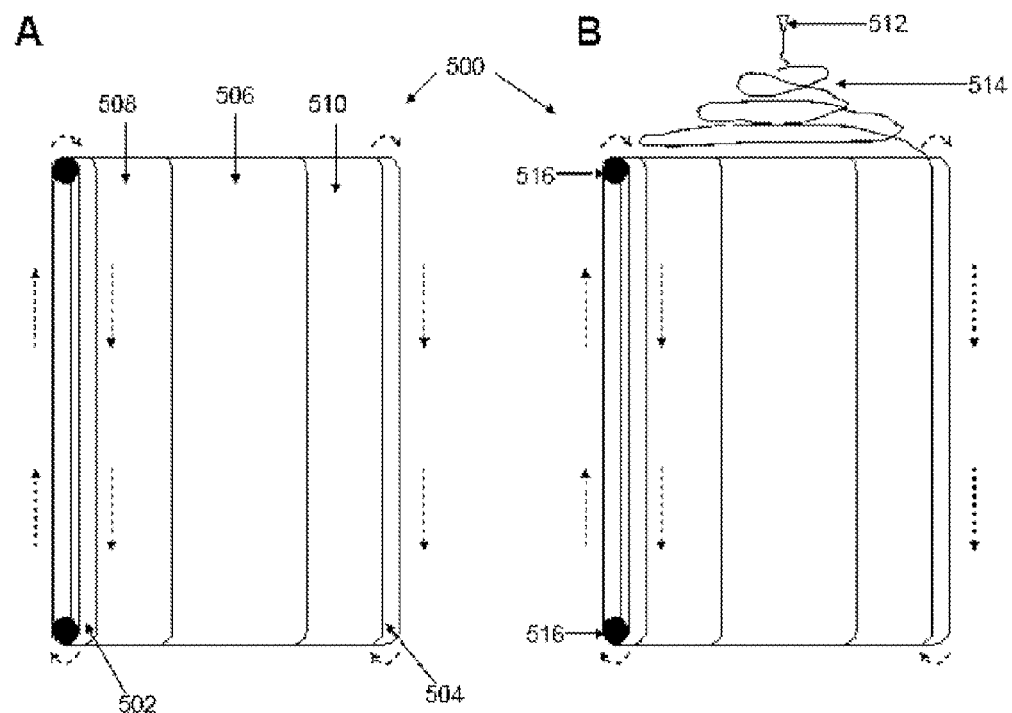
FIG. 8A depicts a conveyor-belt electrospinning apparatus.
FIG. 8B depicts an exemplary method of using a conveyor-belt assembly as a collector for polymer fibers during electrospinning.

An exemplary conveyor-belt assembly is depicted in FIG. 8A. In the depicted embodiment, the conveyer-belt assembly 500 comprises two electrically conductive edges 502 and 504 and an electrically conductive center region 506 separated by two electrically insulative regions 508 and 510. The assembly 500 rotates about two longitudinal axes by rollers 516 that are attached to rotational machinery (not shown). Each roller 516 has its own longitudinal axis that allows for improved fiber alignment during electrospinning.

An exemplary method of electrospinning a polymer fiber onto a conveyor belt assembly 500 is depicted in FIG. 8B. In the depicted embodiment, a spinneret 512 is aimed at one end of the conveyor belt assembly 500, at the top roller 516. The spinneret 512 is therefore aimed at the small-radius curvature of the roller 516, not at the flat portion of the assembly 500. Polymer fibers 514 that are aligned along the longitudinal axis of the roller 516 deposit across the lengths of non-conducting regions 508 and 510 and across the inner conducting region 506. An initial halo of highly-aligned arching fibers 514 is formed between the two conductive edges 502 and 504 of the multi-section conveyor belt assembly 500, analogous to the arching fibers seen when using the multi-mandrel collector or a multi-section drum collector (see embodiments disclosed above). The arcing fibers 514 have the opposite charge to the outer conducting regions 502 and 504. The arcing fibers 514 lose their charge shortly after deposition and settle onto the non-conducting regions 508 and 510 and the inner conducting region 506 in a manner that is aligned along a first axis of the scaffold and that is parallel to the longitudinal axis of the roller 516. There is thus a constant deposition of arcing fibers 514 and a constant settling of fibers onto the inner conducting region 506 during electrospinning. The region of deposition moves closer and closer to the inner conducting region 506 as electrospinning continues. Eventually, the fibers 514 no longer arc between the two non-conducting regions 508 and 510. Polymer fibers 514 that are aligned along a first axis of the scaffold and parallel to the longitudinal axis of the roller 516 thus form over each non-conducting region 508 and 510 and the inner conducting region 506. After the initial fiber layer is deposited on the conveyor belt assembly 500, the halo disappears and the polymer fibers 514 continue to deposit onto the assembly 500.

Once the aligned fibers reach a critical density and length through the electrospinning process, electrospinning may be stopped or it may continue. If electrospinning is stopped, a single-layer scaffold membrane comprising aligned polymer fibers is generated. If continued, the subsequent deposition of fibers through the same rotation rate and electrical potential applied to the conveyor belt and spinnerets results in the formation of a second layer of fibers, on top of the first layer, having a different orientation from the first aligned fibers deposited on the inner conducting region 506.

In various embodiments, the two outer electrically conducting regions 502 and 504 and the inner conducting region 506 can be constructed of any conductive material, such as stainless steel. The two outer regions 502 and 504 can be grounded or charged. The inner conductive region 506 is not grounded, but instead is a floating potential. An electrically insulating material is used to fill the insulating regions 508 and 510 as solid material. The insulating regions may be constructed of nylon, polyurethane, polyvinylidene fluoride (PVDF), polyaryletheretherketone (PEEK), polytetrafluoroethylene (PTFE) or Teflon™ (various fluoropolymers), or poly(vinyl chloride) (PVC).

The width of each of the conductive regions 502, 504, 506 and insulating regions 508, 510 may vary. In certain embodiments, the outer conducting regions 502 and 504, whether grounded or charged, can be shorter than the inner conducting region 506 that remains ungrounded.

The conveyor belt assembly 500 is rotated around the longitudinal axes of two rollers 516, as shown in FIGS. 8A and 8B. The outer conducting regions 502 and 504 are electrically charged oppositely to the polymer solution. For example, the polymer solution may be positively charged, and the outer conducting regions 502 and 504 negatively charged. Alternatively, the outer conducting regions 502 and 504 may be grounded.

The shape and size of the conveyor belt collectors can be altered. In some embodiments, the width of the conveyor belt assembly can be greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 28 cm, greater than 29 cm, or greater than 30 cm. In some embodiments, the width of the conveyor belt assembly can be less than 30 cm, less than 29 cm, less than 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, or less than 5 cm.

In some embodiments, the width of the inner conducting region can be greater than 0.5 cm, greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, or greater than 25 cm. In some embodiments, the width of the inner conducting region can be less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, less than 1 cm, or less than 0.5 cm.

In some embodiments, the total width of the two non-conducting regions and the inner conducting region can be greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 28 cm, greater than 29 cm, or greater than 30 cm. In some embodiments, the total width of the two non-conducting regions and the inner conducting region can be less than 30 cm, less than 29 cm, less than 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

Conveyer belt assemblies may find application in commercial scale preparation of scaffolds. It is believed that the conveyer belt assemblies can be scaled-up to commercial scale for production of scaffolds having very long lengths. In some embodiments, conveyer belt assemblies can be used to produce scaffolds having a length of greater than 25 feet. It is presently believed that conveyer belt assemblies can be used to produce scaffolds of any desired length.

EXAMPLES

The following examples describe in detail the preparation and properties of certain exemplary fibrous polymer scaffolds, and apparatuses and methods used for their preparation. It will be apparent to those skilled in the art that many modifications, both to materials and methods, may be practiced without departing from the scope of the disclosure.

Although the electrospinning apparatus, and differentially aligned fibrous scaffold fabrication method may be performed with other electrospinning systems, designs and techniques, a description of various functional systems is provided below.

Example 1

Production of a Layer of Aligned Polymer Fibers

Figure 3:
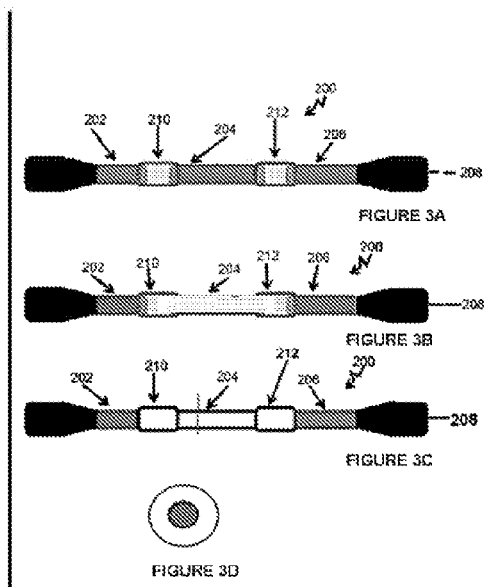
FIG. 3A depicts a side view of a three mandrel rotational assembly having two outer mandrels and an inner mandrel, the mandrels separated one from the other by insulating regions.
FIG. 3B depicts a side view of the three mandrel rotational assembly of FIG. 3A after longitudinally aligned polymer fibers have been deposited onto the inner mandrel.
FIG. 3C depicts a side view of the three mandrel assembly of FIG. 3A after a second layer of randomly or circumferentially aligned polymer fibers have been deposited on the first layer of longitudinally aligned polymer fibers.
FIG. 3D depicts a cross-sectional view of the apparatus of FIG. 3C showing (i) a conductive mandrel base, (ii) a non-conductive tube positioned upon the mandrel, and (iii) first and second layers of polymer fibers.

With respect to the assembly depicted in FIG. 3, a polymer solution used to form the fibers was loaded into a syringe and bubbles were eliminated. The polymer solution was prepared within a chemical hood and the solution source and loaded syringe were stored upright to reduce bubbles. An appropriate length of polytetrafluoroethylene (PTFE) (i.e., Teflon™) tube was cut a sufficient length to connect the syringe pump 38 and the spinneret platform 44, while minimizing the distance between them.

Male and female luer-lock connectors were attached to the tube. A 25 g stainless steel needle was attached to the female luer-lock connector on the tube. The syringe 38 was attached to the male connector on the tube. All luer-lock connections were tightly sealed.

The syringe assembly 32 was attached to the syringe pump 36. The syringe pump 32 modulated the pressure and flow of the polymer solution to the spinneret 42 while preventing blockage. The spinneret 42 was attached to a slot in the needle platform 44. The syringe plunger 36 was pushed manually until the polymer solution reached the needle reservoir. The syringe pump panel was pushed and locked to contact the syringe plunger. The flow rate, syringe size and total solution volume were adjusted via the pump digital display.

The spinneret platform 44 was adjusted to the appropriate height to optimize the distance between the tip of the spinneret and the top of the collector substrate. The spinneret assembly was stationary and centered during the fiber deposition process as polymer solution was allowed to pass through the spinneret tip. Longitudinally aligned fibers were deposited on the surface of the collector.

Example 2

Production of a Multiple Layer Scaffold

A three mandrel assembly was designed as described herein. A first layer of aligned fibers was allowed to form. The spinneret assembly was stationary and centered during the fiber deposition process as polymer solution was allowed to pass through the spinneret tip and aligned fibers formed.

The spinneret assembly was moved along the longitudinal axis of the first insulating region, inner mandrel, and second insulating region during the fiber deposition process. A layer of unaligned fibers was deposited along the surface of the first layer of longitudinally aligned fibers. The unaligned fibers were deposited evenly across the length of the scaffold.

Example 3

Production of a Multiple layer Scaffold

A three mandrel assembly was designed as described herein. The rotation of the mandrel assembly was started. The negative polarity power supply was turned on, set to 6 V, and connected to the outer mandrels to impart a negative charge to them.

The syringe pump was activated to allow the flow of the polymer solution. When a droplet of the polymer solution had formed at the tip of the spinneret, the tube region of the three mandrel assembly was removed, a positive polarity power supply was connected to the spinneret, and turned on in order to impart a positive charge to the polymer solution. The positive voltage was incrementally increased until a jet of polymer solution formed and a Taylor cone stabilized. Once the Taylor cone stabilized, the shield was removed.

The positive and negative voltages were adjusted as necessary to ensure even fiber deposition across the central electrically conducting (ungrounded) mandrel. The Taylor cone was stabilized at the tip of the spinneret so that the cone where the fiber jet extended out toward collector substrate did not change in size. The voltage was decreased if the cone was observed to decrease in size. The voltage was increased if the cone was observed to increase in size.

A first layer of aligned fibers was allowed to form. The spinneret assembly was stationary and centered during formation of the aligned layer of fibers as the polymer solution was allowed to pass through the spinneret tip and aligned fibers formed.

The time at which a halo of fibers between the two insulating regions disappeared was noted. From the time at which the halo of fibers disappeared, electrospinning continued until a desired thickness of the outer unaligned layer(s) was achieved.

During production of the unaligned layer of fibers, the spinneret assembly was allowed to move along the longitudinal axis of the first insulating region, inner mandrel, and second insulating region. The traversing spinneret provided for the formation of unaligned fibers along the surface of the first layer of longitudinally aligned fibers. The unaligned fibers were deposited evenly across the length of the scaffold.

After electrospinning was complete, a shield was placed beneath the spinneret tip to prevent dripping solution from damaging the electrospun fibers on the collector substrate. The positive and negative power supplies, mandrel rotation motor, and syringe pump were stopped simultaneously.

Example 4

Production of a Scaffold Using Poly (L-lactide-co-caprolactone) with Poly(propylene glycol)

Poly (L-lactide-co-caprolactone) is a flexible, elastomeric polymer that will lend desirable physical and mechanical traits to a scaffold including, without limitation, elasticity, improved fiber alignment, and minimal delamination. A polymer stream of poly (L-lactide-co-caprolactone), having a molar weight ratio of 70:30 lactide:caprolactone (PURAC Biomaterials, Lincolnshire, Ill.) at a concentration of 15% w/v, was used to fabricate scaffolds by electrospinning, as previously described (Rosen et al., *Ann. Plast. Surg.*, 25:375-87 (1990)). A dopant of sodium acetate, at a concentration of 0.2% w/v, was added to the polymer prior to electrospinning, as was an additive of poly(propylene glycol), at a concentration of 1% w/v.

Electrospinning proceeded normally as observed by the formation of a stable, electrically-charged polymer jet extending from the spinneret tip as a Taylor cone. A single layer polymer membrane having aligned fibers was successfully generated.

Example 5

Production of a Scaffold Using Poly (L-lactide-co-caprolactone)

A polymer stream of poly (L-lactide-co-caprolactone), having a molar weight ratio of 70:30 lactide:caprolactone (PURAC Biomaterials, Lincolnshire, Ill.) at a concentration of 15% w/v, was used to fabricate scaffolds by electrospinning as described herein. A dopant of sodium acetate at a concentration of 0.2% w/v was added to the polymer prior to electrospinning. No poly(propylene glycol) was added.

Electrospinning proceeded normally. Deposition of the polymer fibers was heterogeneous; fiber deposition was more concentrated at the edges of the scaffold membrane than the center. Polypropylene glycol) thus facilitates the homogeneous or even deposition of poly (L-lactide-co-caprolactone) fibers.

Example 6

Production of a Scaffold Using Poly (L-lactic acid)

Poly(L-lactic acid) is a rigid polymer that will lend increased structural and mechanical integrity to a scaffold. A polymer stream of poly (L-lactic acid) (Fluka Chemie AG, Switzerland) at a concentration of 15% w/v was used to fabricate scaffolds by electrospinning, as described herein. A dopant of sodium acetate was added to the polymer prior to electrospinning, at a concentration of 0.2% w/v.

Electrospinning proceeded normally as observed by the formation of a stable, electrically-charged polymer jet extending from the spinneret tip as a Taylor cone. A single layer polymer membrane having aligned fibers was successfully generated. The polymer membrane was approximately 20 μM thick.

Example 7

Production of a Scaffold Using Poly (L-lactic acid) with Poly(propylene glycol)

A polymer stream of poly (L-lactic acid) (Fluka Chemie AG, Switzerland) was used at a concentration of 15% w/v to fabricate scaffolds by electrospinning, as described herein. A dopant of sodium acetate, at a concentration of 0.2% w/v, was added to the polymer prior to electrospinning as was an additive of polypropylene glycol), at a concentration of 1% w/v.

At the initiation of electrospinning, an over-sized polymer droplet formed at the spinneret tip and dripped onto the collector. To decrease the size of the polymer droplet, the voltage was increased. The resulting polymer droplet formed slowly and the fibers deposited onto the collector at an atypical rate. Dripping continued throughout electrospinning and the polymer jet appeared atypical. Fibers were deposited in a random orientation and the scaffold was thinner at the center than at the edges.

Example 8

Production of a Two-Fiber Scaffold Using Poly (L-lactide-co-caprolactone) with Poly(propylene glycol) and Poly (L-lactic acid)

A polymer stream of poly(L-lactic acid) (Fluka Chemie AG, Switzerland) at a concentration of 15% w/v, and a polymer stream of poly (L-lactide-co-caprolactone), having a molar weight ratio of 70:30 lactide:caprolactone (PURAC Biomaterials, Lincolnshire, Ill.) at a concentration of 15% w/v, were used to fabricate scaffolds by electrospinning, as described herein. A dopant of sodium acetate, at a concentration of 0.2% w/v, was added to each polymer prior to electrospinning. An additive of polypropylene glycol), at a concentration of 1% w/v, was added to the poly (L-lactide-co-caprolactone) polymer solution prior to electrospinning. Both polymer solutions were dispensed at a rate of 1 mL/hr.

Electrospinning proceeded normally with no apparent interference between the two polymer streams. Electrospinning proceeded for 1 hour. Deposition of the polymers occurred via the use of two spinnerets, with the spinneret height of both spinnerets approximately 12 cm above the collector. The two spinnerets were arranged in an orthogonal alignment with respect to the long axis of the rotating mandrel/collector such that the two fibers would be evenly distributed throughout the final scaffold. The collector was rotated at a rate of approximately 20 revolutions per minute. A scaffold membrane was generated. An initial layer of highly aligned polymer fibers was first generated, followed by a second layer with random alignment. The polymer streams were continuous (unbroken) between the two layers. No deformation (curling or shrinking) of the scaffold membrane was observed upon removal from the mandrel.

Example 9

Production of a Two-Fiber Scaffold Using Poly (L-lactide-co-caprolactone) with Poly(propylene glycol) and Poly (L-lactic acid)

A polymer stream of poly(L-lactic acid) (Fluka Chemie AG, Switzerland) at a concentration of 15% w/v and a polymer stream of poly (L-lactide-co-caprolactone), having a molar weight ratio of 70:30 lactide:caprolactone (PURAC Biomaterials, Lincolnshire, Ill.) at a concentration of 15% w/v, were used to fabricate scaffolds by electrospinning, as described herein. A dopant of sodium acetate, at a concentration of 0.2% w/v, was added to each polymer solution prior to electrospinning. An additive of polypropylene glycol), at a concentration of 1% w/v, was added to the poly (L-lactide-co-caprolactone) polymer solution prior to electrospinning. Both polymer solutions were dispensed at a rate of 1 mL/hr for the first 15 minutes of electrospinning; the rate for each was increased to 3 mL/hr for the balance of electrospinning.

Electrospinning proceeded normally for a period of 1 hour and 20 minutes. Deposition of the polymers occurred via the use of two spinnerets, with the spinneret height of both spinnerets approximately 10 cm above the collector. The two spinnerets were arranged in an orthogonal alignment with respect to the long axis of the rotating mandrel/collector such that the two fibers would be evenly distributed throughout the scaffold. The collector was rotated at a rate of approximately 20 revolutions per minute. A scaffold membrane was generated. An initial layer of highly aligned polymer fibers was first generated, followed by a second layer with random alignment.

No deformation (shrinking or curling) of the scaffold membrane was observed upon removal from the collector. The resulting scaffold membrane was approximately 240 μM-450 μM thick and was mechanically stable. Increasing the flow rate to 3 mL per hour did not result in any adverse effects. Electrospinning can thus occur at faster or slower rates without impacting the desired characteristics of the scaffolds produced.

Example 10

Production of a Two-Fiber Scaffold Using Poly (L-lactide-co-caprolactone) with Poly(propylene glycol) and Poly (L-lactic acid)

A polymer stream of poly(L-lactic acid) (Fluka Chemie AG, Switzerland) at a concentration of 15% w/v, and a polymer stream of poly (L-lactide-co-caprolactone), having a molar weight ratio of 70:30 lactide:caprolactone (PURAC Biomaterials, Lincolnshire, Ill.) at a concentration of 15% w/v, were used to fabricate scaffolds by electrospinning, as described herein. A dopant of sodium acetate, at a concentration of 0.2% w/v, was added to each polymer prior to electrospinning. An additive of poly(propylene glycol), at a concentration of 0.5% w/v, was added to the poly (L-lactide-co-caprolactone) polymer solution prior to electrospinning. Both polymer solutions were dispensed at a rate of 1 mL/hr.

Electrospinning proceeded normally for a period of 1 hour. Deposition of the polymers occurred via the use of two spinnerets, with the spinneret height of both spinnerets approximately 10 cm above the collector. The two spinnerets were arranged in an orthogonal alignment with respect to the long axis of the rotating mandrel/collector such that the two fibers would be evenly distributed throughout the final scaffold. The collector was rotated at a rate of approximately 20 revolutions per minute. A scaffold membrane was generated. An initial layer of aligned polymer fibers was first generated, followed by a second layer with random alignment.

Example 11

Production of a Multilayer Scaffold Using Poly (L-lactide-co-caprolactone) with Poly(propylene glycol) and Poly (L-lactic acid)

A polymer stream of poly(L-lactic acid) (Fluka Chemie AG, Switzerland) and a polymer stream of poly (L-lactide-co-caprolactone), having a molar weight ratio of 70:30 lactide:caprolactone (PURAC Biomaterials, Lincolnshire, Ill.), were used to fabricate nanofibrous scaffolds by electrospinning, as described herein. A dopant of sodium acetate was added to each polymer prior to electrospinning at a concentration of 0.2% w/v. Additionally, poly(propylene glycol) was added to the poly (L-lactide-co-caprolactone) polymer solution at a concentration of 1% w/v. Both polymer solutions were dispensed at a rate of 1 mL/hr for the first 8 minutes of electrospinning, and then at 3 mL/hr for the balance of electrospinning.

Electrospinning proceeded normally for a period of 80 minutes. Deposition of the polymers occurred via the use of two spinnerets, with the spinneret height of both spinnerets approximately 10 cm above the collector. The two spinnerets were arranged in an orthogonal alignment with respect to the long axis of the rotating mandrel/collector such that the two fibers would be evenly distributed throughout the final scaffold. The mandrel was rotated at a rate of approximately 20 revolutions per minute.

A two-layer scaffold membrane was generated, the first layer having aligned fibers and the second layer having randomly oriented fibers. The two polymer fibers were continuous (unbroken) between the two layers of the scaffold membrane. The scaffold membrane was 270 µM-300 µM thick.

Example 12

Production of a Multilayer Scaffold Using Poly (L-lactide-co-caprolactone) with Poly(propylene glycol) and Poly (L-lactic acid)

Two separate polymer streams were used to fabricate multilayer nanofibrous scaffolds by electrospinning, as described herein. The first polymer stream consisted of poly (L-lactide-co-caprolactone), having a molar weight ratio of 70:30 lactide:caprolactone (PURAC Biomaterials, Lincolnshire, Ill.), poly(propylene glycol) and sodium acetate such that the fiber composition of this polymer stream was 92.6% poly (L-lactide-co-caprolactone), 6.2% poly(propylene glycol), and 1.2% sodium acetate. The second polymer stream consisted of poly (L-lactic acid) (Fluka Chemie AG, Switzerland) and sodium acetate such that the fiber composition of this polymer stream was 98.7% poly (L-lactic acid) and 1.3% sodium acetate.

A two-layer scaffold membrane was generated, the first layer having aligned fibers and the second layer having randomly oriented fibers. The two polymer fibers were continuous (unbroken) between the two layers of the scaffold membrane. The scaffold displayed a rigidity and an elasticity that was between scaffolds generated by pure poly (L-lactide-co-caprolactone) alone and pure poly (L-lactic acid) alone. The scaffold displayed fast hydration, flexibility, and was readily conformable to a number of surfaces.

Example 13

Production of a Multilayer Scaffold Using Poly (L-lactide-co-caprolactone) with Poly(propylene glycol)

A polymer stream of poly (L-lactide-co-caprolactone), having a molar weight ratio of 70:30 lactide:caprolactone (PURAC Biomaterials, Lincolnshire, Ill.), was used to fabricate scaffolds, as described herein. Sodium acetate and poly (propylene glycol) were also added to the polymer stream such that the final polymer fiber composition was 92.6% poly (L-lactide-co-caprolactone), 6.2% poly(propylene glycol), and 1.2% sodium acetate.

A two-layer scaffold membrane was generated, the first layer having aligned fibers and the second layer having randomly oriented fibers. The polymer fiber was continuous between the two layers of the scaffold membrane. The scaffold membrane was quite flexible, readily conformable to a number of surfaces and very elastic.

Example 14

Production of a Multilayer Scaffold Using Poly (L-lactide-co-caprolactone) with Poly(propylene glycol) and Poly (glycolic acid)

Two separate polymer streams are used to fabricate multilayer scaffolds by electrospinning, as described herein. The first polymer stream is poly (L-lactide-co-caprolactone), having a molar weight ratio of 70:30 lactide:caprolactone (PURAC Biomaterials, Lincolnshire, Ill.), poly(propylene glycol) and sodium acetate such that the fiber composition of this polymer stream is 92.6% poly (L-lactide-co-caprolactone), 6.2% poly(propylene glycol), and 1.2% sodium acetate. The second polymer stream is poly (glycolic acid) (Sigma-Aldrich, St. Louis, Mo.) and sodium acetate such that the fiber composition of this polymer stream is greater than 98% poly (glycolic acid) and less than 2% sodium acetate.

A two-layer scaffold membrane was generated, the first layer having aligned fibers and the second layer having randomly oriented fibers. The polymer fibers are continuous between the two layers of the scaffold membrane.

Example 15

Production of a Multilayer Scaffold Using Poly (L-lactide-co-caprolactone) with Poly(propylene glycol) and Collagen Two separate polymer streams are used to fabricate multilayer scaffolds by electrospinning, as described herein. The first polymer stream is poly (L-lactide-co-caprolactone), having a molar weight ratio of 70:30 lactide:caprolactone (PURAC Biomaterials, Lincolnshire, Ill.), poly(propylene glycol) and sodium acetate such that the fiber composition of this polymer stream will be 92.6% poly (L-lactide-co-caprolactone), 6.2% poly(propylene glycol), and 1.2% sodium acetate. The second polymer stream is collagen (Sigma-Aldrich, St. Louis, Mo.) and sodium acetate such that the fiber composition of this polymer stream is greater than 98% collagen and less than 2% sodium acetate.

A two-layer scaffold membrane was generated, the first layer having aligned fibers and the second layer having randomly oriented fibers. The polymer fibers are continuous between the two layers of the scaffold membrane.

Example 16

Production of a Scaffold Using Poly(L-lactide)

A conduit scaffold composed of polymer fibers was fabricated using the technique of electrospinning. To form the polymer solution, poly(L-lactide), glycerol and sodium acetate were dissolved in hexafluoroisopropanol at weight/volume concentrations of 20 wt %, 2 wt % and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 19 cm from the top of a mandrel assembly. An electrode from a positive polarity high voltage supply was attached to the stainless steel spinneret.

The mandrel assembly included two stainless steel outer mandrels, each having a 2.38 mm outer diameter (OD), aligned end to end along a longitudinal axis and separated by a 9 cm gap (see also the "Tube Connector" embodiment described above). A length of nylon tube (10 cm length (L), 2.38 mm inner diameter (ID), 3.18 mm OD) was used to bridge the gap between the two stainless steel mandrels by inserting one end of each mandrel a distance of 5 mm within the lumen of the nylon tube. The stainless steel mandrels were attached to a rotation assembly and to an electrode from a negative polarity high voltage power supply. The rotation assembly was used to rotate the mandrels and tube around their long axes.

The spinneret platform from which the polymer solution flows was positioned to allow for even deposition of the electrospun fibers across the tube region.

To generate a layer of longitudinally aligned fibers, the mandrel rotation speed was set to 20 RPM. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution.

Electrospinning was allowed to proceed for 10 minutes, until a first aligned layer of polymer fibers was formed. After 10 minutes, a 40 micron layer of longitudinally aligned polymer fibers had formed on the nylon tube. Upon removal, the electrospun fibers formed a conduit shaped polymer scaffold, composed of longitudinally aligned fibers.

Example 17

Production of a Scaffold Using Poly(L-lactide)

A scaffold conduit composed of a single polymer fiber was fabricated using the technique of electrospinning as described herein. To form the polymer solution, poly(L-lactide), triethyl citrate and sodium acetate were dissolved in hexafluoroisopropanol at weight/volume concentrations of 25 wt %, 6 wt % and 0.2 wt %, respectively. The polymer solution was loaded into a syringe and the syringe was attached to a syringe pump. The polymer solution was delivered to the tip of a stainless steel spinneret via PTFE tube. The stainless steel spinneret was positioned a distance of 19 cm from the top of a mandrel assembly. An electrode from a positive polarity high voltage supply was attached to the stainless steel spinneret.

The mandrel assembly included stainless steel outer mandrels (2.38 mm OD) (see also the "Tube Sleeve" embodiment described above). Nylon flexible tube (10 cm L, 2.38 mm ID, 3.18 mm OD) was used as a sleeve on each steel mandrel. The stainless steel mandrel was attached to a rotation assembly and an electrode from a negative polarity high voltage power supply. The rotation assembly was used to rotate the mandrel and tube around their longitudinal axes.

In the fibers that were formed, the direction of alignment and the degree or extent of alignment (or lack of alignment) were controlled by adjusting the rotation rate of the mandrel. The mandrel was rotated at 800 RPM in order to produce a layer of randomly aligned polymer fibers on the nylon tube. Electrospinning proceeded normally for a period of 30 minutes to form a layer of randomly oriented polymer fibers. Upon removal from the nylon tube and mandrel assembly, a 10 cm long polymer scaffold conduit was formed composed of randomly oriented fibers and having a wall thickness of 300 microns.

Example 18

Production of a Multilayer Scaffold Using Poly (L-lactide)

A tubular scaffold composed of polymer fibers was fabricated using the technique of electrospinning. To form the polymer solution, poly(L-lactide), triethyl citrate and sodium acetate were dissolved in hexafluoroisopropanol at weight/volume concentrations of 25 wt %, 6 wt % and 0.2 wt %, respectively. The polymer solution was loaded into a syringe and the syringe was attached to a syringe pump. The polymer solution was delivered to the tip of a stainless steel spinneret via PTFE tube. The stainless steel spinneret was positioned a distance of 16 cm from the top of a mandrel assembly. A positive polarity high voltage supply was attached to the stainless steel spinneret.

The mandrel assembly included two stainless steel mandrels (2.38 mm OD) aligned end to end and separated by a 9 cm region that serves as an insulating region (see also the "Tube Connector" embodiment described above). Nylon flexible tube (10 cm L, 2.38 mm ID, 3.18 mm OD) was used to bridge the gap between the two stainless steel mandrels by inserting one end of each mandrel a distance of 5 mm within the lumen of the nylon tube. The stainless steel mandrels were attached to a rotation assembly and to a negative polarity high voltage power supply. The rotation assembly was used to rotate the mandrels and tube around their long axes.

In the fibers that were formed, the direction of alignment and the degree or extent of alignment (or lack of alignment) were controlled by adjusting the rotation rate of the mandrel. To produce an initial layer of longitudinally aligned fibers, the mandrel rotation speed was set to 20 RPM. The "RUN" button was pressed to begin rotation of the mandrel. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution. Electrospinning was allowed to proceed for 10 minutes until a first aligned layer of longitudinally aligned polymer fibers was formed on the nylon tube. Upon the formation of a sufficiently thick first layer of aligned fibers, a power strip was used to simultaneously turn off all power supplies, the motor for mandrel rotation, and the syringe pump. A shield was then positioned beneath the spinneret to catch dripping polymer solution and to prevent damage to the electrospun sample.

The nylon tube was then separated from the steel mandrels and a stainless steel mandrel (2.38 mm OD) was inserted through the lumen of the nylon tube. The nylon tube was positioned centrally on the stainless steel mandrel. The stainless steel mandrel was attached to the rotation assembly and to the electrode from the negative polarity high voltage power supply. The electrospinning process was commenced as described above.

The direction and extent of fiber alignment (or lack of alignment) were controlled by adjusting the rotation rate of the mandrel. To produce a layer of randomly aligned fibers, the mandrel rotation speed was set to 20 RPM. Polymer fibers were electrospun on the mandrel assembly for 30 minutes to form a layer of randomly oriented fibers.

Upon removal from the nylon tube, the electrospun polymer fibers formed a scaffold conduit that was 10 cm long and had a wall thickness of 400 microns. The scaffold had a thin luminal layer of longitudinally aligned fibers and a thick layer of unaligned polymer fibers.

Example 19

Production of a Multilayer Scaffold Using Poly(DL-lactide-co-caprolactone)

A tubular scaffold composed of polymer fibers was fabricated using the technique of electrospinning. To form the polymer solution, poly(DL-lactide-co-caprolactone), having a lactide:caprolactone molar ratio of 85:15, and sodium acetate were dissolved in hexafluoroisopropanol at weight/volume concentrations of 20 wt % and 0.2 wt %, respectively. The polymer solution was loaded into a syringe and the syringe was attached to a syringe pump. The polymer solution was delivered to the tip of a stainless steel spinneret via PTFE tube. The stainless steel spinneret was positioned a distance of 19 cm from the top of a mandrel assembly. A positive polarity high voltage supply was attached to the stainless steel spinneret.

The mandrel assembly comprised two stainless steel mandrels (2.38 mm OD) aligned end to end and separated by a 9 cm insulating region (see also the "Tube Connector" embodiment described above). Nylon flexible tube (10 cm L, 2.38 mm ID, 3.18 mm OD) was used to bridge the two stainless steel mandrels by inserting one end of each mandrel a distance of 5 mm within the lumen of the nylon tube. The stainless steel mandrels were attached to a rotation assembly and a negative polarity high voltage power supply. The rotation assembly was used to rotate the mandrels and tube around their long axes.

In the fibers that were formed, the direction of alignment and the degree or extent of alignment (or lack of alignment) were controlled by adjusting the rotation rate of the mandrel. To produce an initial layer of longitudinally aligned fibers, the mandrel rotation speed was set to 20 RPM. The "RUN" button was pressed to begin rotation of the mandrel. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution.

Electrospinning proceeded for 10 minutes until a first aligned layer of longitudinally aligned polymer fibers was formed on the nylon tube. Upon the formation of a sufficiently thick first layer of aligned fibers, a power strip was used to simultaneously turn off all power supplies, the motor for mandrel rotation, and the syringe pump. A shield was then positioned beneath the spinneret to catch dripping polymer solution and to prevent damage to the electrospun sample.

The nylon tube was then separated from the steel mandrels and a stainless steel mandrel (2.38 mm OD) was inserted through the lumen of the tube. The nylon tube was positioned centrally on the stainless steel mandrel. The stainless steel mandrel was attached to the rotation assembly and to the electrode from the negative polarity high voltage power supply. The electrospinning process was commenced as described above.

The direction and extent of fiber alignment (or lack of alignment) were controlled by adjusting the rotation rate of the mandrel. To form a layer of randomly aligned fibers, the mandrel rotation speed was set to 20 RPM. Polymer fibers were electrospun on the mandrel assembly for 45 minutes to form a thick layer of randomly oriented fibers. Upon removal from the nylon tube, the electrospun polymer fibers formed a scaffold conduit 10 cm long with a wall thickness of 250 microns. The scaffold had a thin luminal layer of longitudinally aligned fibers and a thick layer of unaligned polymer fibers.

Example 20

Production of a Multilayer Scaffold Using Poly (L-lactide-co-caprolactone)

A tubular scaffold composed of polymer fibers was fabricated using the technique of electrospinning. To form the polymer solution, poly(L-lactide-co-caprolactone), having a lactide:caprolactone molar ratio of 70:30, poly(propylene glycol) (MW: 425), and sodium acetate were dissolved in hexafluoroisopropanol at weight/volume concentrations of 15 wt %, 1 wt % and 0.2 wt % respectively. The polymer solution was loaded into a syringe and the syringe was attached to a syringe pump. The polymer solution was delivered to the tip of a stainless steel spinneret via tube. The stainless steel spinneret was positioned a distance of 15 cm from the top of a mandrel assembly. A positive polarity high voltage supply was attached to the stainless steel spinneret.

The mandrel assembly comprised two stainless steel mandrels (2.38 mm OD) aligned end to end and separated by a 9 cm insulating region (see also the "Tube Connector" embodiment described above). A length of nylon flexible tube (10 cm L, 2.38 mm ID, 3.18 mm OD) was used to bridge the gap between the two stainless steel mandrels by inserting one end of each mandrel a distance within the lumen of the nylon tube. The stainless steel mandrels were attached to a rotation assembly and a negative polarity high voltage power supply. The rotation assembly was used to rotate the mandrels and tube around their long axes.

In the fibers that were formed, the direction of alignment and the degree or extent of alignment (or lack of alignment) were controlled by adjusting the rotation rate of the mandrel. To form an initial layer of longitudinally aligned fibers, the mandrel rotation speed was set to 20 RPM. The "RUN" button was pressed to begin rotation of the mandrel. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution.

Electrospinning proceeded for 10 minutes until a first aligned layer of longitudinally aligned polymer fibers was formed on the nylon tube. Upon the formation of a sufficiently thick first layer of aligned fibers, a power strip was used to simultaneously turn off all power supplies, the motor for mandrel rotation, and the syringe pump. A shield was then positioned beneath the spinneret to catch dripping polymer solution and to prevent damage to the electrospun sample.

The nylon tube was then separated from the steel mandrels and a stainless steel mandrel (2.38 mm OD) was inserted through the lumen of the tube. The nylon tube was positioned centrally on the stainless steel mandrel. The stainless steel mandrel was attached to the rotation assembly and to the electrode from the negative polarity high voltage power supply. The electrospinning process was commenced as described above.

The direction and extent of fiber alignment (or lack of alignment) were controlled by adjusting the rotation rate of the mandrel. To produce a layer of randomly aligned fibers, the mandrel rotation speed was set to 20 RPM. Polymer fibers were electrospun on the mandrel assembly for 45 minutes to form a thick layer of randomly oriented fibers.

Upon removal from the nylon tube, the electrospun polymer fibers formed a scaffold conduit 10 cm long with a wall thickness of 200 microns. The scaffold conduit had a thin luminal layer of longitudinally aligned fibers and a thick layer of unaligned polymer fibers.

Example 21

Production of a Multilayer Scaffold Using Poly(L-lactide-co-caprolactone), Poly(L-lactide) and Poly(L-lactide-co-glycolide)

A tubular scaffold composed of a plurality of polymer fibers was fabricated using the technique of electrospinning. To make the first polymer solution, poly(L-lactide-co-caprolactone) having a lactide:caprolactone molar ratio of 70:30, and sodium acetate were dissolved in hexafluoroisopropanol at weight/volume concentrations of 15 wt % and 0.2 wt % respectively. This polymer solution was loaded into a syringe and the syringe was attached to a syringe pump. The polymer solution was delivered to the tip of a stainless steel spinneret via a tube. The stainless steel spinneret was positioned a distance of 15 cm from the top of a mandrel assembly. A positive polarity high voltage supply was attached to the stainless steel spinneret.

The mandrel assembly comprised two stainless steel mandrels (2.38 mm OD) aligned end to end and separated by a 9 cm insulating region (see also the "Tube Connector" embodiment described above). A length of nylon flexible tube (10 cm L, 2.38 mm ID, 3.18 mm OD) was used to bridge the two stainless steel mandrels by inserting one end of each mandrel a distance within the lumen of the nylon tube. The stainless steel mandrels were attached to a rotation assembly and a negative polarity high voltage power supply. The rotation assembly was used to rotate the mandrels and tube around their long axes.

In the fibers that were formed, the direction of alignment and the degree or extent of alignment (or lack of alignment) were controlled by adjusting the rotation rate of the mandrel. To form an initial layer of longitudinally aligned fibers, the mandrel rotation speed was set to 20 RPM. The "RUN" button was pressed to begin rotation of the mandrel. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution.

Electrospinning proceeded for 10 minutes until a first layer of longitudinally aligned poly(L-lactide-co-caprolactone) polymer fibers was formed on the nylon tube. Upon the formation of a sufficiently thick first layer of aligned fibers, a power strip was used to simultaneously turn off all power supplies, the motor for mandrel rotation, and the syringe pump. A shield was then positioned beneath the spinneret to catch dripping polymer solution and to prevent damage to the electrospun sample.

The nylon tube was then separated from the steel mandrels and a stainless steel mandrel (2.38 mm OD) was inserted through the lumen of the tube. The nylon tube was positioned centrally on the stainless steel mandrel. The stainless steel mandrel was attached to the rotation assembly and to the electrode from the negative polarity high voltage power supply.

A second polymer solution was created: poly(L-lactide), poly(L-lactide-co-glycolide) and sodium acetate were dissolved in hexafluoroisopropanol at 15 wt %, 15 wt % and 0.2 wt % concentrations, respectively. This polymer solution was loaded into the syringe pump and the electrospinning process was commenced as described above.

The direction and extent of fiber alignment (or lack of alignment) were controlled by adjusting the rotation rate of the mandrel. To create a second layer of randomly aligned fibers, the mandrel rotation speed was set to 20 RPM. Polymer fibers were electrospun on the mandrel assembly for 10 minutes to form a layer of randomly oriented polymer fibers of poly(L-lactide) and poly(L-lactide-co-glycolide). Upon removal from the nylon tube, the electrospun polymer fibers formed a polymer scaffold conduit with a luminal layer of longitudinally aligned poly(L-lactide-co-caprolactone) fibers and an outer layer of randomly aligned polymer fibers of poly(L-lactide) and poly(L-lactide-co-glycolide).

Example 22

Production of a Scaffold Using Poly(L-lactide)

A tubular scaffold composed of polymer fibers was fabricated using the technique of electrospinning. To form the polymer solution, poly(L-lactide) and sodium acetate were dissolved in hexafluoroisopropanol at weight/volume concentrations of 28 wt % and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 16 cm from the top of a mandrel assembly. An electrode from a positive polarity high voltage supply was attached to the stainless steel spinneret.

The mandrel assembly comprised two stainless steel mandrels (2.38 mm outer diameter (OD)) aligned end to end and separated by a 5 cm insulating region (see also the "Tube Connector" embodiment described above). PVC tube (6 cm L, 2.38 mm inner diameter (ID), 4 mm OD) was used to bridge the gap between the two stainless steel mandrels by inserting one end of each mandrel a distance of 5 mm within the lumen of the nylon tube. The stainless steel mandrels were attached to a rotation assembly and an electrode from a negative polarity high voltage power supply. The rotation assembly was used to rotate the mandrels and tube around their longitudinal axes.

For a layer of longitudinally aligned fibers, the mandrel rotation speed was set to 20 RPM. The negative polarity power supply was turned on and set to the appropriate voltage to charge the outer mandrels. The syringe pump was set to "RUN" to activate flow of the polymer solution. Once a droplet of polymer solution had formed at the tip of the spinneret, the tube region was covered with a shield and the positive power supply was turned on to charge the polymer solution. The voltage of the positive power supply was incrementally increased until a jet of polymer solution had formed and the Taylor cone had stabilized. The shield was removed after the Taylor cone stabilized. The positive and negative voltages were adjusted as necessary to control the jet of polymer solution.

Electrospinning proceeded for 10 minutes until a layer of longitudinally aligned polymer fibers was formed on the PVC tube. Upon the formation of a sufficiently thick first layer of aligned fibers, the electrospinning process was stopped. Upon removal, the electrospun fibers formed a tubular polymer scaffold composed of longitudinally aligned fibers.

Example 23

Production of a Scaffold Using Poly(L-lactide)

A tubular scaffold composed of polymer fibers was fabricated using the technique of electrospinning. To form the polymer solution, poly(L-lactide) (PLLA) and sodium acetate were dissolved in hexafluoroisopropanol at weight/volume concentrations of 28 wt % and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 19 cm from the top of a mandrel assembly. An electrode from a positive polarity high voltage supply was attached to the stainless steel spinneret.

The mandrel assembly comprised a stainless steel mandrel (2.38 mm OD) (see also the "Tube Connector" embodiment described above). PVC tube (6 cm length, 2.38 mm ID, 3.18 mm OD) was used as a sleeve on the steel mandrel. The stainless steel mandrel was attached to a rotation assembly and an electrode from a negative polarity high voltage power supply. The rotation assembly was used to rotate the mandrel and tube around its longitudinal axis.

In the fibers that were formed, the direction of alignment and the degree or extent of alignment (or lack of alignment) were controlled via the insulating PVC tube. The mandrel was rotated at 20 RPM to produce a layer of randomly aligned polymer fibers on the PVC tube. The electrospinning process was commenced as described above. Polymer fibers were electrospun on the mandrel assembly for 10 minutes to form a sufficiently thick layer of randomly oriented polymer fibers. Upon removal, the electrospun fibers formed a tubular polymer scaffold composed of randomly aligned fibers.

Example 24

Production of a Multilayer Scaffold Using Poly(L-lactide-co-caprolactone) with Poly(propylene glycol)

A tubular scaffold composed of polymer fibers is fabricated using the technique of electrospinning. To make the polymer solution, poly(L-lactide-co-caprolactone), having a lactide:caprolactone molar ratio of 70:30, polypropylene glycol) (MW: 425), and sodium acetate are dissolved in hexafluoroisopropanol at weight/volume concentrations of 15 wt %, 1 wt % and 0.2 wt % respectively. The polymer solution is loaded into a syringe and the syringe is attached to a syringe pump. The polymer solution is delivered to the tip of a stainless steel spinneret via PTFE tube. The stainless steel spinneret is positioned a distance of 15 cm from the top of a mandrel assembly. An electrode from a positive polarity high voltage supply is attached to the stainless steel spinneret.

The mandrel assembly comprises two stainless steel mandrels (2 mm OD) aligned end to end and separated by a 10 cm insulating region (see also the "Tube Connector" embodiment described above). PVC tube (11 cm L, 2 mm ID, 4 mm OD) is used to bridge the gap between the two stainless steel mandrels by inserting one end of each mandrel a distance of 5 mm within the lumen of the PVC tube. The stainless steel mandrels are attached to a rotation assembly and an electrode from a negative polarity high voltage power supply. The rotation assembly is used to rotate the mandrels and tube around their long axes.

For an initial layer of longitudinally aligned fibers, the mandrel rotation speed is set to 20 RPM. The negative polarity power supply is turned on and set to the appropriate voltage to charge the outer mandrels. The syringe pump is set to "RUN" to activate flow of the polymer solution. Once a droplet of polymer solution is formed at the tip of the spinneret, the tube region is covered with a shield and the positive power supply is turned on to charge the polymer solution. The voltage of the positive power supply is incrementally increased until a jet of polymer solution forms and the Taylor cone stabilizes. The shield is removed after the Taylor cone stabilizes. The positive and negative voltages are adjusted as necessary to control the jet of polymer solution.

Electrospinning is allowed to proceed for 10 minutes until a first layer of longitudinally aligned polymer fibers is formed on the PVC tube. Upon the formation of a sufficiently thick first layer of aligned fibers, the electrospinning process is stopped.

The PVC tube is then separated from the steel mandrels and a stainless steel mandrel (2 mm OD) is inserted through the lumen of the tube. The PVC tube is positioned centrally on the stainless steel mandrel. The stainless steel mandrel is attached to the rotation assembly and to the electrode from the negative polarity high voltage power supply.

The stainless steel spinneret is attached to a motorized slide assembly to traverse specific lengths along an axis parallel to the longitudinal axis of the steel collector mandrel. The spinneret is traversed back and forth across a distance of 11 cm at a rate of 1 cm/min to ensure even deposition across an 11 cm length of PVC tube. The electrospinning process is commenced as described above. Polymer fibers are electrospun on the mandrel assembly for 22 minutes to form a thick layer of randomly oriented polymer fibers.

The direction and extent of fiber alignment or lack of alignment are controlled by adjusting the rotation speed of the mandrel. In this example, a rotation speed of 20 RPM produces a layer of randomly aligned fibers. Upon removal from the nylon tube, the electrospun polymer fibers form a tubular scaffold with a luminal layer of longitudinally aligned fibers and a layer of unaligned polymer fibers for a total wall thickness of 250 microns.

Example 25

Production of a Multilayer Scaffold Using Poly(L-lactide-co-caprolactone) with Poly(propylene glycol)

A tubular scaffold composed of polymer fibers is fabricated using the technique of electrospinning. To create the polymer solution, poly(L-lactide-co-caprolactone), having a lactide:caprolactone molar ratio of 70:30, poly(propylene glycol) (MW: 425), and sodium acetate are dissolved in hexafluoroisopropanol at weight/volume concentrations of 15 wt %, 1 wt % and 0.2 wt % respectively. The polymer solution is loaded into a syringe and the syringe is attached to a syringe pump. The polymer solution is delivered to the tip of a stainless steel spinneret via PTFE tube. The stainless steel spinneret is positioned a distance of 15 cm from the top of a mandrel assembly. An electrode from a positive polarity high voltage supply is attached to the stainless steel spinneret.

The mandrel assembly comprises two stainless steel mandrels (2 mm OD) aligned end to end and separated by a 10 cm insulating region (see also the "Tube Connector" embodiment described above). PVC tube (11 cm L, 2 mm ID, 4 mm OD) is used to bridge the two stainless steel mandrels by inserting one end of each mandrel a distance of 5 mm within the lumen of the PVC tube. The stainless steel mandrels are attached to a rotation assembly and an electrode from a negative polarity high voltage power supply. The rotation assembly is used to rotate the mandrels and tube around their long axes.

For an initial layer of longitudinally aligned fibers, the mandrel rotation speed is set to 20 RPM. The negative polarity power supply is turned on and set to the appropriate voltage to charge the outer mandrels. The syringe pump is set to "RUN" to activate flow of the polymer solution. Once a droplet of polymer solution is formed at the tip of the spinneret, the tube region is covered with a shield and the positive power supply is turned on to charge the polymer solution. The voltage of the positive power supply is incrementally increased until a jet of polymer solution forms and the Taylor cone stabilizes. The shield is removed after the Taylor cone stabilizes. The positive and negative voltages are adjusted as necessary to control the jet of polymer solution.

Electrospinning is allowed to proceed for an appropriate amount of time until a first aligned layer of a desired thickness forms. The appropriate amount of time is 10 minutes to form a layer of longitudinally aligned polymer fibers on the PVC tube. Upon the formation of a sufficiently thick first layer of aligned fibers, the electrospinning process is stopped.

The PVC tube is then separated from the steel mandrels and a stainless steel mandrel (2 mm OD) is inserted through the lumen of the tube. The PVC tube is positioned centrally on the stainless steel mandrel. The stainless steel mandrel is attached to the rotation assembly and to the electrode from the negative polarity high voltage power supply.

The stainless steel spinneret is attached to a motorized slide assembly to traverse specific lengths along an axis parallel to the longitudinal axis of the steel collector mandrel. The spinneret is traversed back and forth across a distance of 11 cm at a rate of 1 cm/min to ensure even deposition across an 11 cm length of PVC tube. The electrospinning process is commenced as described above.

The direction and extent of fiber alignment or lack of alignment are controlled by adjusting the rotation speed of the mandrel. In this example, a rotation speed of 2000 RPM produces a layer of circumferentially aligned fibers. Upon removal from the nylon tube, the electrospun polymer fibers form a tubular scaffold with a luminal layer of longitudinally aligned fibers and an outer layer of circumferentially aligned fibers.

Example 26

Production of a Multilayer Scaffold Using Poly(L-lactide-co-caprolactone)

A tubular scaffold composed of polymer fibers was fabricated using the technique of electrospinning. To form the polymer solution, poly(L-lactide-co-caprolactone), having a lactide:caprolactone molar ratio of 70:30, and sodium acetate were dissolved in hexafluoroisopropanol at weight/volume concentrations of 15 wt %, and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 15 cm from the top of a mandrel assembly. An electrode from a positive polarity high voltage supply was attached to the stainless steel spinneret.

The mandrel assembly consisted of two stainless steel outer mandrels (OD: 2.38 mm, L: 20 cm) aligned end to end with an aluminum inner mandrel (OD: 2.38 mm, L: 12 cm) in between (see also the "Three Mandrel" embodiment described above). Two nylon tube pieces (ID: 2.38 mm, OD: 3.18 mm, L: 1.5 cm) were used to connect the ends of the steel and aluminum mandrels in the insulating region such that each end of the steel outer mandrels and each end of the aluminum inner mandrel was inserted 2 mm into the lumen of the nylon tube. The resultant mandrel assembly comprised two steel outer mandrels at each end attached to an aluminum inner mandrel via nylon tube.

The steel outer mandrels were attached to a rotation assembly that was used to rotate the entire mandrel assembly along its longitudinal axis. The mandrel assembly was rotated at 20 RPM. Both steel outer mandrels were also attached to electrodes from a negative polarity high voltage power supply. Polymer fibers were electrospun onto the mandrel assembly, allowing longitudinally aligned polymer fibers to deposit onto the nylon tube and the aluminum mandrel.

After a layer of longitudinally aligned polymer fibers had deposited on the aluminum mandrel, a second layer randomly oriented fibers was deposited. After a total electrospinning time of 40 minutes, full evaporation of residual hexafluoroisopropanol, and removal from the aluminum mandrel, the electrospun fibers formed a tubular scaffold composed of a luminal layer of longitudinally aligned fibers and an outer layer of unaligned fibers. The tubular scaffold had a total wall thickness of 200 microns.

Example 27

Production of a Multilayer Scaffold Using Poly(L-lactide-co-caprolactone) with Poly(propylene glycol)

A tubular scaffold composed of polymer fibers was fabricated using the technique of electrospinning. To form the polymer solution, poly(L-lactide-co-caprolactone), having a lactide:caprolactone molar ratio of 70:30, polypropylene glycol (MW 425), and sodium acetate were dissolved in hexafluoroisopropanol at weight/volume concentrations of 15 wt %, 1 wt % and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 15 cm from the top of a mandrel assembly. An electrode from a positive polarity high voltage supply was attached to the stainless steel spinneret.

The mandrel assembly included two stainless steel outer mandrels (long, OD: 1.6 mm, L: 18 cm) aligned end to end with a stainless steel inner mandrel (short, OD: 1.6 mm, L: 10 cm) in between (see also the "Three Mandrel" embodiment described above). Two PVC tube pieces (ID: 1.6 mm, OD: 3 mm, L: 1.5 cm) were used to connect the ends of the outer mandrels and inner mandrel such that each mandrel was inserted 2 mm into the lumen of the PVC tube located in each of the two insulating region located between the mandrels. The resultant assembly had two 10 cm L steel mandrels at each end attached to a centrally located 10 cm L steel mandrel via two 1.5 cm L PVC tube sections.

The steel outer mandrels were attached to a rotation assembly that was used to rotate the entire mandrel assembly along its longitudinal axis. The mandrel assembly was rotated at 20 RPM. Both long steel mandrels were also attached to electrodes from a negative polarity high voltage power supply. Polymer fibers were electrospun onto the mandrel assembly. Longitudinally aligned polymer fibers deposited on the steel inner mandrel and the PVC tube sections.

After a layer of longitudinally aligned polymer fibers had deposited on the steel inner mandrel, subsequently deposited polymer fibers were randomly oriented. After a total electrospinning time of 40 minutes, full evaporation of residual hexafluoroisopropanol, and removal from the stainless steel mandrel, the electrospun fibers formed a tubular scaffold composed of a luminal layer of longitudinally aligned fibers and an outer layer of unaligned fibers. The tubular scaffold had a total wall thickness of 200 microns.

Example 28

Production of a Multilayer Scaffold Using Poly(L-lactide-co-caprolactone) with Poly(propylene glycol)

A tubular scaffold composed of polymer fibers was fabricated using the technique of electrospinning. To form the polymer solution, poly(L-lactide-co-caprolactone), having a lactide:caprolactone molar ratio of 70:30, polypropylene glycol (MW 425), and sodium acetate were dissolved in hexafluoroisopropanol at weight/volume concentrations of 15 wt %, 1 wt % and 0.2 wt % respectively. The polymer solution was loaded into a syringe and the syringe was attached to a syringe pump. The polymer solution was delivered to the tip of a stainless steel spinneret via PTFE tube. The stainless steel spinneret was positioned a distance of 15 cm from the top of a mandrel assembly. An electrode from a positive polarity high voltage supply was attached to the stainless steel spinneret.

The mandrel assembly consisted of two stainless steel mandrels (long, OD: 1.6 mm, L: 18 cm) aligned end to end with a stainless steel mandrel (short, OD: 1.6 mm, L: 10 cm) in between (see also the "Three Mandrel" embodiment described above). Two PVC tube pieces (ID: 1.6 mm, OD: 3 mm, L: 1.5 cm) were used to connect the ends of the long and steel inner mandrels such that the appropriate end of the long steel mandrel and each end of the steel inner mandrel were inserted 2 mm into the lumen of the PVC tube. The resultant assembly comprised two 10 cm L steel mandrels at each end attached to a centrally located 10 cm L steel mandrel via two 1.5 cm L PVC tube sections.

The outer steel mandrels were attached to a rotation assembly that was used to rotate the entire mandrel assembly along its longitudinal axis. The mandrel assembly was rotated at 20 RPM. Both long steel mandrels were also attached to electrodes from a negative polarity high voltage power supply.

The stainless steel spinneret was attached to a motorized slide assembly to traverse specific lengths along parallel to the longitudinal axis of the steel inner mandrel. Polymer fibers were electrospun onto the mandrel assembly. Longitudinally aligned polymer fibers deposited on the steel inner mandrel and the PVC tube sections.

After a layer of longitudinally aligned polymer fibers had deposited on the steel inner mandrel, as second layer of randomly oriented polymer fibers was deposited. During random fiber deposition, the stainless steel spinneret was traversed back and forth across a distance of 12 cm at a rate of 1 cm/min to ensure even deposition across the 10 cm length of steel inner mandrel. After a total electrospinning time of 24 minutes and removal from the steel mandrel, the electrospun fibers formed a tubular scaffold composed of a luminal layer of longitudinally aligned fibers and an outer layer of unaligned fibers. The tubular scaffold had a total wall thickness of 170 microns.

Example 29

Production of a Multilayer Scaffold Using Poly(L-lactide-co-caprolactone) with Poly(propylene glycol)

A tubular scaffold composed of polymer fibers is fabricated using the technique of electrospinning. To form the polymer solution, poly(L-lactide-co-caprolactone), having a lactide:caprolactone molar ratio of 70:30, polypropylene glycol (MW 425), and sodium acetate are dissolved in hexafluoroisopropanol at weight/volume concentrations of 15 wt %, 1 wt % and 0.2 wt % respectively. The polymer solution is loaded into a syringe and the syringe is attached to a syringe pump. The polymer solution is delivered to the tip of a stainless steel spinneret via PTFE tube. The stainless steel spinneret is positioned a distance of 15 cm from the top of a mandrel assembly. An electrode from a positive polarity high voltage supply is attached to the stainless steel spinneret.

The mandrel assembly consists of two stainless steel mandrels (long, OD: 1.6 mm, L: 18 cm) aligned end to end with a stainless steel mandrel (short, OD: 1.6 mm, L: 10 cm) in between (see also the "Three Mandrel" embodiment described above). Two PVC tube pieces (ID: 1.6 mm, OD: 3 mm, L: 1.5 cm) are used to connect the ends of the long and steel inner mandrels such that the appropriate end of the long steel mandrel and each end of the steel inner mandrel are inserted 2 mm into the lumen of the PVC tube. The resultant assembly comprises two 10 cm L steel mandrels at each end attached to a centrally located 10 cm L steel mandrel via two 1.5 cm L PVC tube sections.

The outer steel mandrels are attached to a rotation assembly that is used to rotate the entire mandrel assembly along its longitudinal axis. The mandrel assembly is rotated at 20 RPM. Both long steel mandrels are also attached to electrodes from a negative polarity high voltage power supply.

The stainless steel spinneret is attached to a motorized slide assembly to traverse specific lengths along an axis parallel to the longitudinal axis of the steel collector mandrel. Polymer fibers are electrospun onto the mandrel assembly. Longitudinally aligned polymer fibers deposit on the steel inner mandrel and the PVC tube sections.

After a sufficiently thick layer of longitudinally aligned polymer fibers deposits on the steel inner mandrel, subsequently depositing fibers are not longitudinally aligned. At this point, the mandrel rotation is adjusted to 2,000 RPM and the spinneret assembly is traversed back and forth across a distance of 12 cm at a rate of 1 cm/min to ensure circumferential fiber alignment and even deposition across the 10 cm length of steel inner mandrel, respectively. After a sufficiently thick layer of circumferentially aligned fibers is deposited the electrospinning process is stopped. After removal from the steel mandrel, the electrospun fibers form a tubular scaffold composed of a luminal layer of longitudinally aligned fibers and an outer layer of circumferentially aligned fibers.

Example 30

Production of a Multilayer Scaffold Using Poly(L-lactide) with Triethyl Citrate

A tubular scaffold composed of randomly aligned polymer fibers is fabricated using the technique of electrospinning. To form the polymer solution, poly(L-lactide), triethyl citrate (TEC) and sodium acetate are dissolved in hexafluoroisopropanol at weight/volume concentrations of 25 wt %, 6 wt % and 0.2 wt % respectively. The polymer solution is loaded into a syringe and the syringe is attached to a syringe pump. The polymer solution is delivered to the tip of a stainless steel spinneret via PTFE tube. The stainless steel spinneret is positioned a distance of 15 cm from the top of a mandrel assembly. An electrode from a positive polarity high voltage supply is attached to the stainless steel spinneret.

The mandrel assembly consists of a stainless steel mandrel attached to a rotation assembly on both ends. An electrode from a negative polarity high voltage power supply is attached to the stainless steel mandrel. The mandrel is rotated around its longitudinal axis at 100 RPM.

The stainless steel spinneret is attached to a motorized slide assembly to traverse specific lengths along an axis parallel to the longitudinal axis of the steel collector mandrel. The spinneret is traversed back and forth across a distance of 12 cm at a rate of 1 cm/min to ensure even deposition across 12 cm length of stainless steel mandrel. Randomly oriented polymer fibers are deposited across the stainless steel mandrel. After a total electrospinning time of 24 minutes, full evaporation of residual hexafluoroisopropanol, and removal from the steel mandrel, the electrospun fibers form a tubular scaffold composed of a layer of randomly aligned (or unaligned) fibers.

Example 31

Production of an Aligned Scaffold Membrane Using Positively Charged Conductive Arms to Direct Fiber Alignment To determine if additional charged elements could be used to alter the overall electric field within the electrospinning area and thereby guide nanofiber movement and alignment, an electrospinning setup was used as depicted in FIGS. 7A and 7B. Two rectangular, stainless steel conducting arms (0.5 cm×7 cm) were attached to a rectangular aluminum spinneret-holder plate (0.9 c,×10.3 cm). The arms and plate were oriented to direct fiber movement predominantly along the longitudinal axis of the collector (see also the "Conductive Arms" embodiment described above). A 25 gauge syringe spinneret, one inch in length, (McMaster-Carr, Elmhurst, Ill.) was attached to a syringe containing a polymer solution consisting of: 15% w/v poly (L-lactide-co-caprolactone) having a molar weight ratio of 70:30 lactide:caprolactone (PURAC Biomaterials, Lincolnshire, Ill.), 0.2% w/v sodium acetate (Sigma-Aldrich, St. Louis, Mo.), and 1% w/v poly(propylene glycol) (Sigma-Aldrich, St. Louis, Mo.) dissolved in hexafluoroisopropanol. The collector was a stainless steel drum (10 cm in diameter, 10 cm long) which was negatively charged (−6.0 kV) during the run. The spinneret-holder plate, conductive arms, and syringe spinneret were all positively charged and kept between 18.5 and 20.0 kV during electrospinning. The polymer solution flow rate was governed by a computer-controlled syringe pump and kept between 1.0 and 3.0 mL/h. The general electrospinning process proceeded as described previously (Rosen et al., *Ann. Plast. Surg.*, 25:375-87 (1990)). Electrospinning lasted for 35 minutes.

Figure 9:
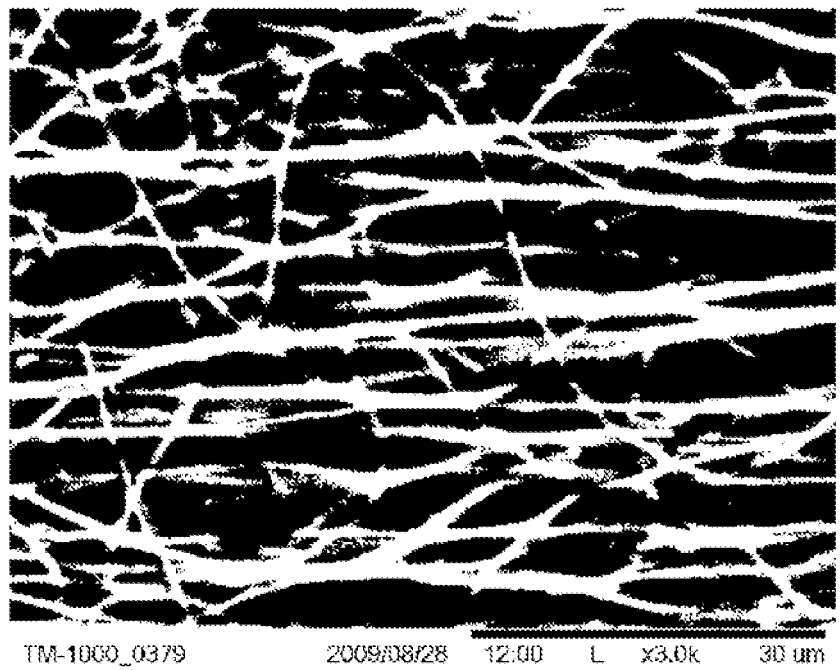
FIG. 9 is a scanning electron micrograph of the single fiber scaffold membrane sheet produced in Example 31. Longitudinal axis is left-right in image.

Electrospinning proceeded normally as observed by the formation of a stable, electrically-charged polymer jet extending from the spinneret tip as a Taylor cone. Based on macroscopic observation of initial fiber deposition, it could be seen that the fiber movement and deposition were directed predominantly along the longitudinal axis of the collector; the fiber could be seen depositing from end to end across the longitudinal axis of the collector. Scanning electron microscopy analysis of the resulting nanofibrous scaffold revealed that the polymer fibers are aligned along the longitudinal axis of the sample, as expected (FIG. 9). Therefore, fiber movement and deposition, and thus the resulting fiber alignment within the resulting scaffold, can be controlled using additional conductive elements (conductive arms) placed deliberately within the electrospinning area to specifically alter the electric field in order to guide the charged fiber onto the collector.

Example 32

Comparison of Spinneret Height Effects on Fiber Alignment When Using Positively Charged Conductive Arms in Conjunction with Multi-Section Drum Collector The distance between the spinneret tip and the top surface of the collector can have a large effect on the resulting deposition of polymer fibers onto a collector. To determine the effect of changes in spinneret height, the following polymer solution was used: 15% w/v poly (L-lactide-co-caprolactone) having a molar weight ratio of 70:30 lactide:caprolactone (PURAC Biomaterials, Lincolnshire, Ill.), 0.2% w/v sodium acetate (Sigma-Aldrich, St. Louis, Mo.), and 1% w/v poly (propylene glycol) (Sigma-Aldrich, St. Louis, Mo.) dissolved in hexafluoroisopropanol. Two rectangular stainless steel arms (2.5 cm×7 cm) were attached to a rectangular aluminum spinneret-holder plate (~3 cm×10 cm) (see also the "Conductive Arms" embodiment described above). The collector used was a multi-section drum as described previously (see also the "Three Component Rotational Assembly" embodiment described above). For the first approximately 7 minutes of electrospinning, the polymer solution flow rate was kept 1 mL/h (positive voltage ~25.0 kV) to allow a halo of highly-aligned arching fibers to form along the longitudinal axis of the multi-section drum. After the halo disappeared, the flow rate was increased to 3 mL/h (positive voltage ~25.0 kV) to hasten the remainder of the scaffold formation. Total run time was approximately 1 hour. This electrospinning run was performed twice, at two different spinneret heights (12 cm and 15 cm above the collector, respectively), to compare alignment differences due to spinneret height.

Figure 10:
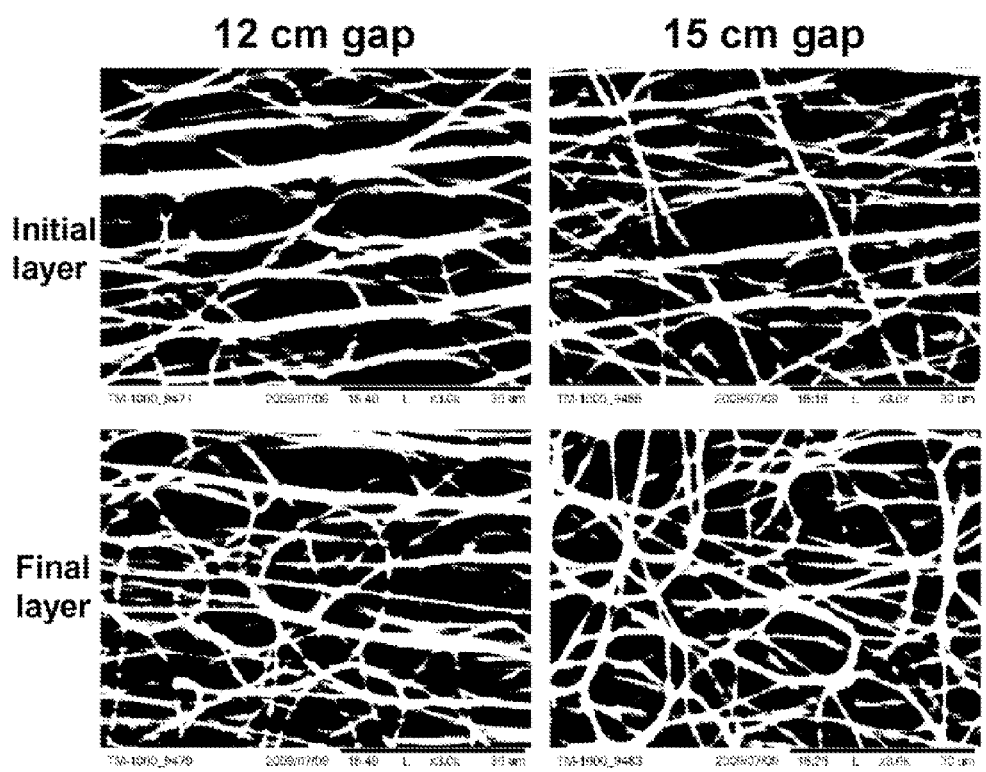
FIG. 10 depicts scanning electron micrograph analysis of the polymer scaffolds produced in Example 32. The first column depicts both the first and second layers of a scaffold produced from a spinneret height of 12 cm. The second column depicts both the first and second layers of a scaffold produced from a spinneret height of 15 cm. Longitudinal axis is left-right in image.

Electrospinning proceeded normally when the spinneret height was 15 cm and a clear halo of arching fibers was seen forming the initial fiber layer. When a 12 cm spinneret height was used no halo was seen, but an electrospinning polymer fiber was still clearly visible. Scanning electron microscopy analysis of the resulting fibrous polymer scaffolds (FIG. 10) shows that alignment in both cases is similar, despite the lack of arching fibers during the initial stage of electrospinning when the 12 cm spinneret gap was employed. This suggests that the conductive arms can help make up for a lack of arching fibers in terms of overall alignment. Additionally, the alignment in the final side of the graft generated with a 12 cm spinneret gap appears to be slightly better than with a 15 cm spinneret gap, suggesting that the conductive arms work best when they can contain the moving fiber for a larger fraction of its travel from the spinneret tip to the collector. Therefore, differences in spinneret height can be used to help control the degree of nanofiber alignment when the conductive arm mechanisms are employed.

Example 33

Comparison of Conductive Arm Width when Electrospinning onto a Multi-Section Drum Collector The conductive arms alter the overall electric field in the electrospinning area to manipulate fiber movement and deposition. However, differences in the electric field also cause differences in the minimum required voltage to achieve an electrospinning fiber. To determine the effect of changes in conductive arm width, conductive arms of varying dimensions were used: (1) 1.5 cm×7 cm, (2) 0.5 cm×7 cm (see also the "Conductive Arms" embodiment described above). For electrospinning, the following polymer solution was used: 15% w/v poly (L-lactide-co-caprolactone) having a molar weight ratio of 70:30 lactide:caprolactone (PURAC Biomaterials, Lincolnshire, Ill.), 0.2% w/v sodium acetate (Sigma-Aldrich, St. Louis, Mo.), and 1% w/v poly(propylene glycol) (Sigma-Aldrich, St. Louis, Mo.) dissolved in hexafluoroisopropanol. Two separate electrospinning runs were performed, one with two conductive arms having the dimensions of (1) shown above, the second with two conductive arms having the dimensions of (2) shown above. In each case, the conductive arms were stainless steel and were attached to a rectangular aluminum spinneret-holder plate (1.9 cm×10.3 cm). The collector used was a multi-section drum as described previously (see also the "Three Component Rotational Assembly" embodiment described above). For the first 5-6 minutes of each electrospinning run, the polymer solution flow rate was kept 1 mL/h to allow a halo of highly-aligned arching fibers to form along the longitudinal axis of the multi-section drum. After the halo disappeared, the flow rate was increased to 3 mL/h for the remainder of the run.

Figure 11:
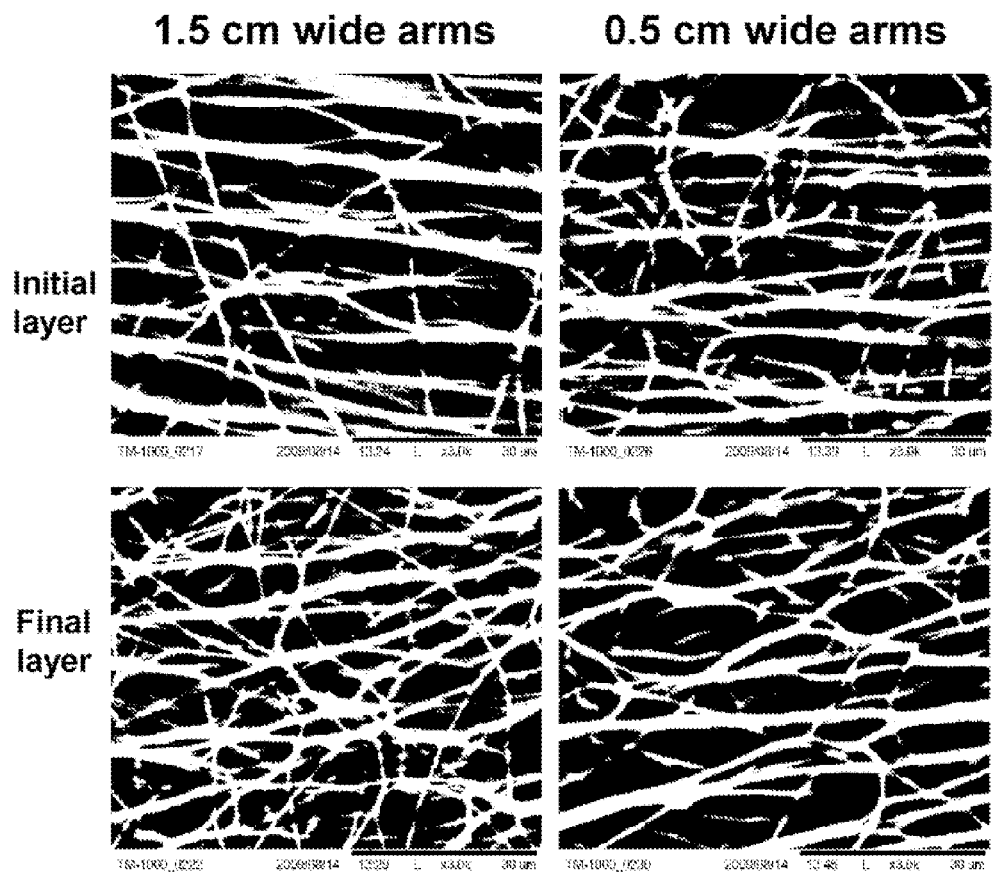
FIG. 11 depicts scanning electron micrograph analysis of the polymer scaffolds produced in Example 33. The first column depicts both the first and second layers of a scaffold produced using conductive arms having a width of 1.5 cm. The second column depicts both the first and second layers of a scaffold produced using conductive arms having a width of 0.5 cm. Longitudinal axis is left-right in image.

In both instances, electrospinning proceeded normally, but the required voltage to induce an electrospinning polymer fiber was different. When using the conductive arms of 1.5 cm width, the positive voltage was 21 kV when the flow rate was 1 mL/hr and 24 kV when the flow rate was 3 mL/hr. When using the conductive arms of 0.5 cm width, the positive voltage was 18.5 kV when the flow rate was 1 mL/hr and 22 kV when the flow rate was 3 mL/hr. Scanning electron microscopy analysis of the resulting scaffolds (FIG. 11) show that the generated fiber alignment under these circumstances was approximately equivalent, demonstrating that fiber alignment is not noticeably compromised by the width of the conductive arms, but the voltage required for electrospinning can be drastically reduced by using narrower conductive arms. Therefore, the electrospinning process and required voltages can be specifically controlled by varying the size and geometry of the conductive arms, and thus, manipulating the induced electric field.

Example 34

Altering Fiber Alignment by Changing the Orientation of the Conductive Arms With Respect to the Longitudinal Axis of a Multi-Section Drum Collector Examples 31-33 demonstrate how the conductive arms can aid and increase nanofiber alignment on drum collectors when the arms are oriented parallel to the longitudinal axis of the rotating drum collector (as depicted in FIG. 7B). To determine the effect of changes in conductive arm orientation, the same conditions were used as in Example 32, but the spinneret-holder plate and attached conductive arms (2.5 cm×7.5 cm) were rotated 90° with respect to the longitudinal axis of the collector, such that the conductive arms were perpendicular to the longitudinal axis of the collector and acted to repel the fiber from spinning in the longitudinal direction.

Figure 12:
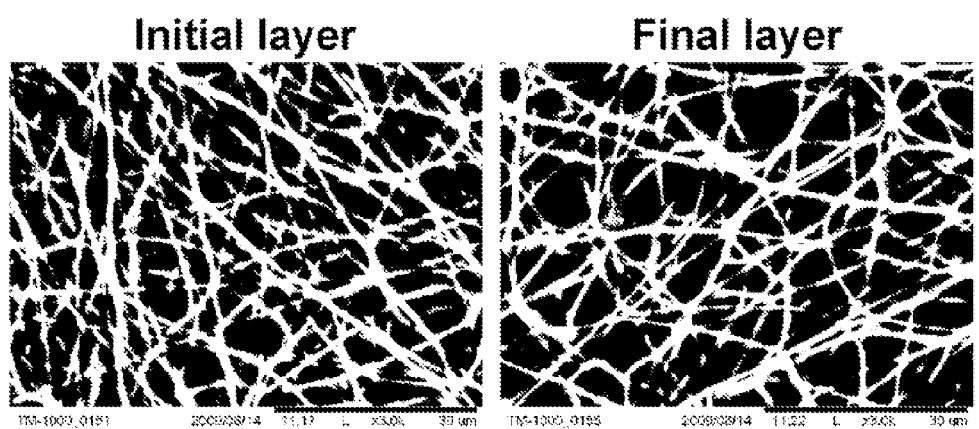
FIG. 12 depicts scanning electron micrograph analysis of the polymer scaffold produced in Example 34. Longitudinal axis is left-right in image.

During electrospinning, no arching fibers were seen, even through this run was performed using the multi-section drum collector. Scanning electron microscopy analysis of the resulting scaffold (FIG. 12) show that there is no obvious primary axis of fiber alignment on either side of the nanofibrous sheet. These results suggest that the orientation of the conductive arms can be used to manipulate the direction of fiber movement and the overall fiber alignment within the resulting nanofibrous structure. Depending on the orientation of the conductive arms with respect to the geometry of the collector, fiber alignment along a particular axis can be either increased or reduced.

Example 35

Altering Fiber Alignment Within Specific Layers of a Nanofibrous Tube by Changing the Orientation of the Conductive Arms With Respect to the Longitudinal Axis of a Multi-Mandrel Collector Example 34 demonstrated how the orientation of the conductive arms can be used to specifically direct nanofiber movement and orientation on a multi-section drum collector. To determine if the conductive arm orientation could be changed during the course of an electrospinning run to create varying layers of nanofiber orientation, a multi-mandrel collector (1.65 mm diameter, center mandrel) was used as the collector (see also the "Three Component Rotational Assembly" embodiment described above). The following polymer solution was used for electrospinning: 15% w/v poly (L-lactide-co-caprolactone) having a molar weight ratio of 70:30 lactide:caprolactone (PURAC Biomaterials, Lincolnshire, Ill.), 0.2% w/v sodium acetate (Sigma-Aldrich, St. Louis, Mo.), and 1% w/v poly(propylene glycol) (Sigma-Aldrich, St. Louis, Mo.) dissolved in hexafluoroisopropanol. Two rectangular stainless steel conductive arms (0.5 cm×7 cm) were attached to a rectangular aluminum spinneret-holder plate (0.9 cm×10.3 cm).

Two separate electrospinning runs were performed. In both runs, a highly aligned nanofiber layer was formed by running the polymer solution at a flow rate of 1 mL/hr and 18.5-20.0 kV for ~3.5 minutes with the conductive arms aligned parallel to the longitudinal axis of the collector. After the initial layer was formed, a second layer was generated at a faster polymer flow rate (3 mL/hr) and higher positive voltage (20.0-21.0 kV) to hasten the electrospinning process. In the first run, the conductive arm orientation was kept parallel to the longitudinal axis of the collector during the generation of the second nanofibrous layer. In the second run, the conductive arms were rotated 90° during the deposition of the second layer, such that the arms were oriented perpendicular to the longitudinal axis of the collector.

Figure 13:
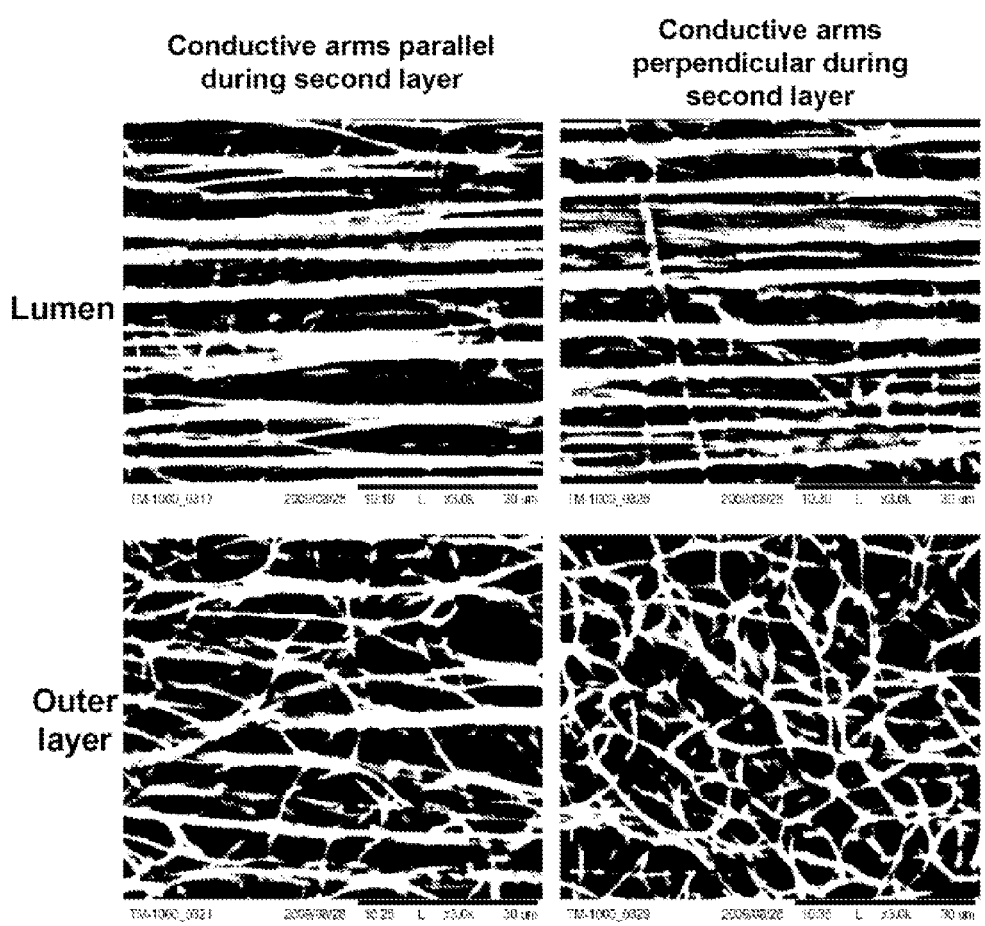
FIG. 13 depicts scanning electron micrograph analysis of both layers of the polymer scaffolds produced in Example 35. Longitudinal axis is left-right in the images.

During electrospinning of the initial layer, arching fibers were seen in both runs, as expected based on the parallel alignment of the conductive arms. During the electrospinning of the second layer, the moving fiber was still seen in both cases, regardless of conductive arm orientation. However, scanning electron micrographs of the resulting scaffolds (FIG. 13) show that the fiber alignment in the final layer is dependent on the orientation of the conductive arms. When the arms remained oriented parallel to the longitudinal axis of the collector during the final layer, the fibers in the final layer were also aligned in the longitudinal axis, but when the arms were oriented perpendicular to the longitudinal axis of the collector, the fiber alignment in the final layer was more random. Therefore, the conductive arms can be used to manipulate fiber movement and alignment not only on a drum collector, but also on a mandrel collector, suggesting that the conductive arms are a versatile tool for fiber control under many circumstances. Additionally, fiber alignment can be specifically tailored within the various layers of a nanofibrous graft by altering the orientation of the conductive arms for each layer accordingly.

Example 36

Generating Nanofibrous Sheets with Highly Aligned Fibers by Utilizing a Multi-Section Conveyor Belt Collector Fiber alignment depends at least in part on the size and geometry of the collector used because the electrospinning nanofibers deposit predominantly onto the available area of the collector. As disclosed herein, longitudinal fiber alignment tends to be greatest when using collectors with a large longitudinal/radial axis ratio (such as small-diameter mandrels) compared to those with a smaller such ratio (such as large-diameter drums). However, while small-diameter mandrels create excellent longitudinal fiber alignment, they have small overall surface area and cannot be used to generate larger sheet-like membranes. In this example, a multi-section conveyor belt (FIGS. 8A & 8B) is used, which has a large longitudinal/radial axis ratio at its curved edges, but also has a larger overall surface area for generating large sheets.

A multi-section conveyor belt as depicted in FIG. 8A (0.125" radius of curvature at edges, ~0.5 ft×4.0 ft overall dimensions) was used as the collector (see also the "Conveyor-Belt" embodiment described above). The conveyor belt was constructed from polyvinyldifluoride (PVDF) as the electrically insulative material and aluminum tape was used to create the conductive regions as depicted in FIG. 8A. The following polymer solution was used for electrospinning: 15% w/v poly (L-lactide-co-caprolactone) having a molar weight ratio of 70:30 lactide:caprolactone (PURAC Biomaterials, Lincolnshire, Ill.), 0.2% w/v sodium acetate (Sigma-Aldrich, St. Louis, Mo.), and 1% w/v poly(propylene glycol) (Sigma-Aldrich, St. Louis, Mo.) dissolved in hexafluoroisopropanol. During electrospinning, the spinneret was aimed at the top rounded edge of the conveyor belt, as shown in FIG. 8B, to help encourage fiber deposition and alignment along the longitudinal axis of the collector, as opposed to the radial axis. Two separate electrospinning runs were tested: (1) electrospinning with conductive arms (0.25 cm×7.0 cm) attached to the spinneret-holder plate and oriented parallel to the longitudinal axis of the collector, (2) electrospinning with no conductive arms.

Figure 14:
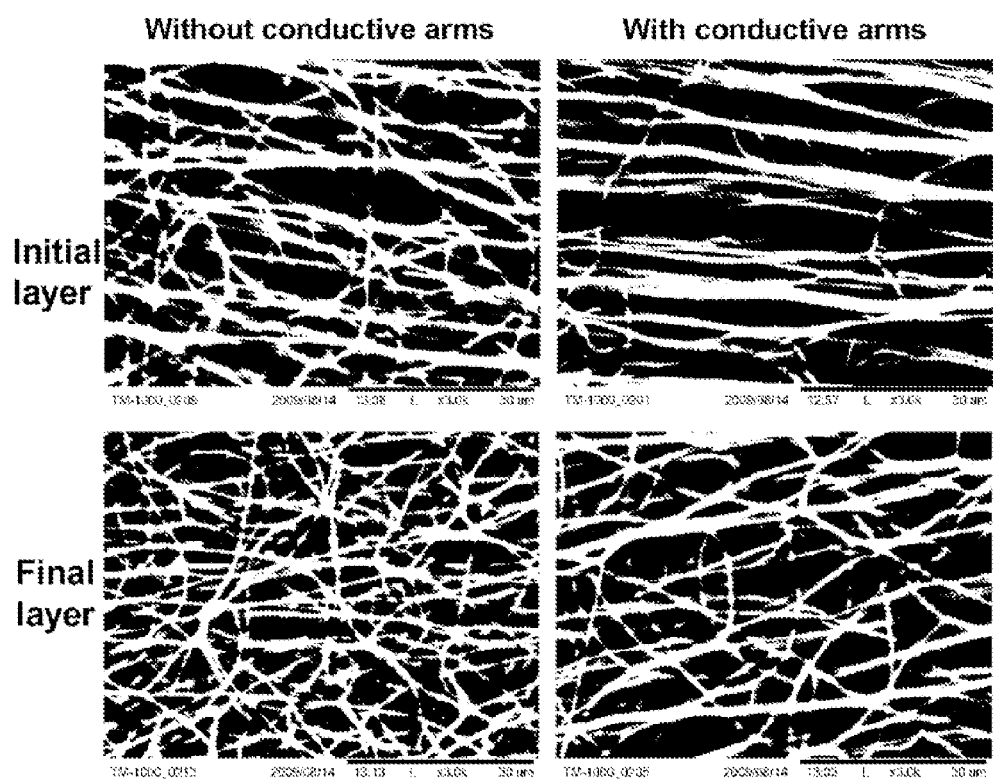
FIG. 14 depicts scanning electron micrograph analysis of both layers of the polymer scaffolds produced in Example 36. The first column depicts both the first and second layers of a scaffold produced without the use of conductive arms. The second column depicts both the first and second layers of a scaffold produced using conductive arms. Longitudinal axis is left-right in the images.

During both runs of electrospinning, an initial halo of highly-aligned arching fibers was formed between the two conductive edges of the multi-section conveyor belt, analogous to the arching fibers seen when using either the a multi-mandrel collector or a multi-section drum collector (see also the "Three Component Rotational Assembly" embodiment described above). After the initial fiber layer was deposited on the conveyor belt, the halo disappeared and the nanofibers continued to deposit onto the collector. Scanning electron micrographs of the resulting scaffolds (FIG. 14) show that the fibers in the initial layer of the nanofibrous membranes have a high degree of longitudinal alignment, while the final layer has a lesser, but still obvious, alignment. Use of the conductive arms generated better alignment in both the initial and final layers of the nanofibrous membranes than without the arms. Therefore, the multi-section conveyor belt collector can be used to make fibrous polymer scaffold membranes having both large surface area and a high degree of fiber alignment. Additionally, conductive arms can be incorporated into the electrospinning procedure to further enhance fiber alignment in the resulting membranes.

From the above description of the disclosure, those skilled in the art will perceive improvements, changes and modifications. Such improvements, changes and modifications within the skill of the art are regarded as covered by the appended claims directly or as equivalents.

What is claimed is:

1. A fibrous polymer scaffold, comprising:
   a first layer of aligned polymer fibers, the fibers comprising poly(L-lactide-co-caprolactone) and poly(propylene glycol); and
   a second layer of unaligned polymer fibers, the fibers comprising poly(L-lactide-co-caprolactone) and poly(propylene glycol);
   wherein poly(propylene glycol) is present in an amount of 0.1%-10% of the total weight of the polymer fibers.

2. The fibrous polymer scaffold of claim 1,
   wherein at least one polymer fiber in the first layer and at least one polymer fiber in the second layer is the same polymer fiber that is continuous between the layers.

3. The fibrous polymer scaffold of claim 1, wherein the scaffold is a shape selected from a membrane and a conduit.

4. The fibrous polymer scaffold of claim 1, wherein the polymer fibers of the first layer are aligned parallel to a first axis of the scaffold, the first axis being parallel to a longitudinal axis of a collector used to create the scaffold.

5. The fibrous polymer scaffold of claim 1, wherein the polymer fibers of the first layer are longitudinally aligned.

6. The fibrous polymer scaffold of claim 1, wherein the polymer fibers of the second layer are randomly oriented.

7. The fibrous polymer scaffold of claim 1, wherein the polymer fibers of the second layer are aligned parallel to a second axis of the scaffold.

8. The fibrous polymer scaffold of claim 1, wherein the polymer fibers of the second layer are circumferentially aligned.

9. The fibrous polymer scaffold of claim 1, wherein the polymer fibers of the first layer and the polymer fibers of the second layer comprise a material selected from an aliphatic polyester, a poly(alkylene) oxide, poly(L-lactic acid), 70/30 L-lactide/e-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, poly(ethylene-co-vinyl) alcohol, poly(vinyl) alcohol, poly(ethylene) glycol, poly(propylene) glycol, poly-L-lactide-co-glycolide-co-c-ε-caprolactone, poly(tetrafluoroethylene), poly(dioxanone), polyglactin 910 and combinations thereof;
   wherein the aliphatic polyester is selected from D-lactide, L- lactide, poly(lactic acid), poly(lactide) glycolic acid, poly(glycolic acid), poly(glycolide), glycolide, poly(lactide-co-glycolide), poly(lactic acid-co-glycolic acid), epsilon-caprolactone, poly(epsilon-caprolactone), poly(lactide-co-caprolactone) and poly(glycolide-co-caprolactone) and combinations thereof; and
   wherein the poly(alkylene) oxide is selected from poly(ethylene) oxide and poly(propylene) oxide.

10. The fibrous polymer scaffold of claim 1, comprising an additive selected from poly(ethylene oxide), triethyl citrate, glycerol, poly(ethylene glycol), and combinations thereof.

11. The fibrous polymer scaffold of claim 1, comprising a salt selected from NaCl, $KH_2PO_4$, $K_2HPO_4$, $KIO_3$, KCl, $MgSO_4$, $MgCl_2$, $NaHCO_3$, $CaCl_2$ sodium acetate, salt of acetic acid, salt of ascorbic acid, salt of citric acid, salt of lactic acid, salt of glycolic acid, and combinations thereof.

12. The fibrous polymer scaffold of claim 1, wherein the at least one continuous polymer fiber comprises sodium acetate.

13. A method of implanting a fibrous polymer scaffold, comprising: contacting a defect in a tissue of a subject with a first layer of a fibrous polymer scaffold according to claim 1, so that the scaffold at least partially replaces the defect; and
securing the scaffold in place at the defect.

14. A kit for the repair of wounds, surgical incisions or biopsies comprising:
  (i) a fibrous polymer scaffold according to claim 1; and
  (ii) instructions for using the scaffold to repair wounds, surgical incisions or biopsies by promoting the regeneration of at least one anatomical biological component selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, and tendons.

* * * * *